(12) United States Patent
Weiner et al.

(10) Patent No.: US 7,534,772 B2
(45) Date of Patent: May 19, 2009

(54) METHODS FOR ENHANCING ANTIBODY-INDUCED CELL LYSIS AND TREATING CANCER

(75) Inventors: George Weiner, Iowa City, IA (US); Gunther Hartmann, Alfter (DE)

(73) Assignees: University of Iowa Research Foundation, Iowa City, IA (US); Coley Pharmaceutical GmbH, Dusseldorf (DE)

(*) Notice: Subject to any disclaimer, the term of this patent is extended or adjusted under 35 U.S.C. 154(b) by 0 days.

(21) Appl. No.: 09/888,326

(22) Filed: Jun. 22, 2001

(65) Prior Publication Data

US 2003/0026801 A1    Feb. 6, 2003

Related U.S. Application Data

(60) Provisional application No. 60/213,346, filed on Jun. 22, 2000.

(51) Int. Cl.
*A61K 48/00*     (2006.01)
*A61K 39/395*    (2006.01)

(52) U.S. Cl. .................................. 514/44; 424/130.1
(58) Field of Classification Search .................. 514/44; 536/24.5, 24.3, 23.1; 424/130.1, 1.11
See application file for complete search history.

(56) References Cited

U.S. PATENT DOCUMENTS

| | | | |
|---|---|---|---|
| 3,854,480 A | 12/1974 | Zaffaroni | |
| 3,906,092 A | 9/1975 | Hilleman et al. | |
| 4,452,775 A | 6/1984 | Kent | |
| 4,469,863 A | 9/1984 | Ts'o et al. | |
| 4,675,189 A | 6/1987 | Kent et al. | |
| 5,023,243 A | 6/1991 | Tullis | |
| 5,075,109 A | 12/1991 | Tice et al. | |
| 5,133,974 A | 7/1992 | Paradissis et al. | |
| 5,208,146 A * | 5/1993 | Irie | 435/7.23 |
| 5,212,295 A | 5/1993 | Cook | |
| 5,248,670 A | 9/1993 | Draper et al. | |
| 5,359,052 A | 10/1994 | Stec et al. | |
| 5,407,686 A | 4/1995 | Patel et al. | |
| 5,506,212 A | 4/1996 | Hoke et al. | |
| 5,512,668 A | 4/1996 | Stec et al. | |
| 5,521,302 A | 5/1996 | Cook | |
| 5,565,354 A | 10/1996 | Ostberg | |
| 5,567,610 A | 10/1996 | Borrebaeck et al. | |
| 5,569,825 A | 10/1996 | Lonberg et al. | |
| 5,571,893 A | 11/1996 | Baker et al. | |
| 5,585,479 A | 12/1996 | Hoke et al. | |
| 5,599,797 A | 2/1997 | Cook et al. | |
| 5,663,153 A | 9/1997 | Hutcherson et al. | |
| 5,679,647 A | 10/1997 | Carson et al. | |
| 5,723,335 A | 3/1998 | Hutcherson et al. | |
| 5,736,152 A | 4/1998 | Dunn | |
| 5,780,448 A | 7/1998 | Davis | |
| 5,786,189 A | 7/1998 | Locht et al. | |
| 5,837,856 A | 11/1998 | Arnold, Jr. et al. | |
| 5,849,719 A | 12/1998 | Carson et al. | |
| 5,856,465 A | 1/1999 | Stec et al. | |
| 5,883,237 A | 3/1999 | Stec et al. | |
| 5,969,135 A * | 10/1999 | Ramasamy et al. | 544/264 |
| 6,015,886 A | 1/2000 | Dale et al. | |
| 6,194,388 B1 | 2/2001 | Krieg et al. | |
| 6,207,646 B1 | 3/2001 | Krieg et al. | |
| 6,214,804 B1 | 4/2001 | Felgner et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,306,393 B1 * | 10/2001 | Goldenberg | 424/141.1 |
| 2002/0091097 A1 | 7/2002 | Bratzler et al. | |
| 2002/0164341 A1 | 11/2002 | Davis et al. | |
| 2003/0050263 A1 | 3/2003 | Krieg et al. | |
| 2003/0050268 A1 | 3/2003 | Krieg et al. | |
| 2003/0055014 A1 | 3/2003 | Bratzler | |
| 2003/0091599 A1 | 5/2003 | Davis et al. | |
| 2003/0100527 A1 | 5/2003 | Krieg et al. | |
| 2003/0104523 A1 | 6/2003 | Bauer et al. | |
| 2003/0139364 A1 | 7/2003 | Krieg et al. | |
| 2003/0148316 A1 | 8/2003 | Lipford et al. | |
| 2003/0148976 A1 | 8/2003 | Krieg et al. | |
| 2003/0166001 A1 | 9/2003 | Lipford | |
| 2003/0181406 A1 | 9/2003 | Schetter et al. | |
| 2003/0191079 A1 | 10/2003 | Krieg et al. | |
| 2003/0232074 A1 | 12/2003 | Lipford et al. | |
| 2003/0232856 A1 | 12/2003 | MacFarlane | |

(Continued)

FOREIGN PATENT DOCUMENTS

EP    0 092 574 B1    11/1983

(Continued)

OTHER PUBLICATIONS

Crystal R.G. Transfer of genes to humans: early lessons and obstacles to success (Science, 1995; 270:404-409).*
Walther W. et al. Viral vectors for gene transfer. (Drugs, 2000; 60:249-271).*
Greco O. et al. Cancer gene therapy: delivery, delivery, delivery (Front. Biosci., 2002; 7:d1516-d1524; 2002).*
Agrawal S. et al. Medicinal chemistry and therapeutic potential of CpG DNA (Trends in Mol. Med., 2002; 8:114-121).*
Hartmann G. et al. Delineation of a CpG phosphorothioate oligodeoxynucleotide for activating primate immune responses in vitro and in vivo. (Journ. Immunology, 2000; 164:1617-1624).*
Krieg A. The CpG motif: implications for clinical immunology. (BioDrugs, 1998; 5:341-346).*

(Continued)

*Primary Examiner*—J. E Angell
(74) *Attorney, Agent, or Firm*—Wolf, Greenfield & Sacks, P.C.; Gregg C. Benson

(57) ABSTRACT

The invention relates to methods and products for treating cancer. In particular the invention relates to combinations of nucleic acids and antibodies for the treatment and prevention of cancer. The invention also relates to diagnostic methods for screening cancer cells.

4 Claims, 6 Drawing Sheets

U.S. PATENT DOCUMENTS

| | | |
|---|---|---|
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |

FOREIGN PATENT DOCUMENTS

| | | |
|---|---|---|
| EP | 0 239 490 B1 | 9/1987 |
| EP | 0 301 758 B1 | 2/1989 |
| EP | 0 468 520 A2 | 1/1992 |
| WO | WO91/12811 A1 | 9/1991 |
| WO | WO92/03456 A1 | 3/1992 |
| WO | WO92/04381 A1 | 3/1992 |
| WO | WO92/18522 A1 | 10/1992 |
| WO | WO92/21353 A1 | 12/1992 |
| WO | WO94/19945 A1 | 9/1994 |
| WO | WO95/05853 A1 | 3/1995 |
| WO | WO95/26204 A1 | 10/1995 |
| WO | WO96/02555 A1 | 2/1996 |
| WO | WO96/02560 A1 | 2/1996 |
| WO | WO96/35782 A1 | 11/1996 |
| WO | WO97/28259 A1 | 8/1997 |
| WO | WO98/14210 A1 | 4/1998 |
| WO | WO98/16247 A1 | 4/1998 |
| WO | WO98/18810 A1 | 5/1998 |
| WO | WO98/32462 A1 | 7/1998 |
| WO | WO98/37919 A1 | 9/1998 |
| WO | WO98/40100 A1 | 9/1998 |
| WO | WO 9840100 A1 * | 9/1998 |
| WO | WO 98/42378 * | 10/1998 |
| WO | WO98/52581 A1 | 11/1998 |
| WO | WO98/55495 A2 | 12/1998 |
| WO | WO99/51259 A2 | 10/1999 |
| WO | WO99/56755 A1 | 11/1999 |
| WO | WO99/58118 A2 | 11/1999 |
| WO | WO99/61056 A2 | 12/1999 |
| WO | WO00/06588 A1 | 2/2000 |
| WO | WO00/14217 A3 | 3/2000 |
| WO | WO 00/27428 A1 | 5/2000 |
| WO | WO00/67023 A1 | 11/2000 |
| WO | WO 00/67795 A1 | 11/2000 |
| WO | WO 00/75348 A1 | 12/2000 |

| | | |
|---|---|---|
| WO | WO 01/22972 A2 | 4/2001 |
| WO | WO 01/95935 A1 | 12/2001 |
| WO | WO 02/069369 A2 | 9/2002 |
| WO | WO 2004/007743 A2 | 1/2004 |
| WO | WO 2004/026888 A2 | 4/2004 |
| WO | WO 2004/094671 A2 | 11/2004 |
| WO | WO 2006/080946 A2 | 8/2006 |
| WO | WO 2007/031877 A2 | 3/2007 |
| WO | WO 2007/038720 A2 | 4/2007 |

OTHER PUBLICATIONS

Wooldridge J. et al. Immunostimulatory oligonucleotides containing CpG motifs enhance the efficacy of monoclonal antibody therapy of lymphocytes. (Blood, 1997; 89:2994-2998).*
Winkler et al. (Blood, 1999; vol. 94(7), pp. 2217-2224).*
Pawade et al. (Histopathology, 1995; vol. 27(2), pp. 129-137).*
Taji et al. (Japanese Juornal of Cancer Research, 1998; vol. 89(7), pp 748-759).*
Micouin, A. et al. (Leukemia, 1997; vol. 1, pp. 552-560).*
Azad RF et al., Antiviral activity of a phosphorothioate oligonucleotide complementary to RNA of the human cytomegalovirus major immediate-early region. *Antimicrob Agents Chemother*. Sep. 1993;37(9):1945-54.
Azuma I, Biochemical and immunological studies on cellular components of tubercle bacilli. *Kekkaku* 1992;67(9):45-55.
Ballas ZK et al., Induction of NK activity in murine and human cells by CpG motifs in oligodeoxynucleotides and bacterial DNA. *J Immunol*. Sep. 1, 1996;157(5):1840-5.
Bayever E et al., Systemic administration of a Phosphorothioate oligonucleotide with a sequence complementary to p53 for acute myelogenous leukemia and myelodysplastic syndrome: initial results of a phase I trial. *Antisense Res Dev*. 1993 Winter;3(4):383-90.
Beaucage SL et al., Deoxynucleoside phosphoramidites—a new class of key intermediates for deoxypolynucleotide synthesis. *Tetrahedron Lett* 22:1859, 1981.
Bennett RM et al., DNA binding to human leukocytes. Evidence for a receptor -mediated association, internalization, and degradation of DNA. *J Clin Invest*. Dec. 1985; 76(6):2182-90.
Blaxter ML et al., Genes expressed in *Brugia malayi* infective third stage larvae. *Mol Biochem Parasitol*. Apr. 1996;77(1);77-93.
Boggs RT et al., Characterization and modulation of immune stimulation by modified oligonucleotides. *Antisense Nucleic Acid Drug Dev*. Oct. 1997;7(5);461-71.
Branda RF et al., Amplification of antibody production by phosphorothioate oligodeoxynucleotides. *J Lab Clin Med*. Sep. 1996;128(3):329-38.
Branda RF et al., Immune stimulation by an antisense oligomer complementary to the rev gene of HIV-1. *Biochem Pharmacol*. May 25, 1993;45(10):2037-43.
Chace JH et al., Regulation of differentiation in CD5+ and conventional B cells. Sensitivity to LPS-induced differentiation and interferon-gamma-mediated inhibition of differentiation. *Clin Immunol Immunopathol*. Sep. 1993;68(3):327-32.
Chang YN et al., The palindromic series I repeats in the simian cytomegalovirus major immediate-early promoter behave as both strong basal enhancers and cyclic AMP response elements. *J Virol*. Jan. 1990; 64(1):264-77.
Chu RS et al., CpG oligodeoxynucleotides act as adjuvants that switch on T helper 1 (Th1) immunity. *J Exp Med*. Nov. 17, 1997;186(10);1623-31.
Coiffier B et al., Rituximab (anti-CD20 monoclonal antibody) for the treatment of patients with relapsing or refractory aggressive lymphoma: a multicenter phase II study. *Blood*. Sep. 15, 1998;92(6):1927-32.
Cowdery JS et al., Bacterial DNA induces NK cells to produce IFN-gamma in vivo and increases to toxicity of lipopolysaccharides. *J Immunol*. Jun. 15, 1996;156(12):4570-5.
Crystal RG, Transfer of genes to humans: early lessons and obstacles to success. *Science*. Oct. 20, 1995;270(5235):404-10.
Davis HL et al., CpG DNA is a potent enhancer of specific immunity in mice immunized with recombinant hepatitis B surface antigen. *J Immunol*. Jan. 15, 1998;160(2):870-6.

Decker T et al., Immunostimulatory CpG-oligonucleotides cause proliferation, cytokine production, and an immunogenic phenotype in chronic lymphocytic leukemia B cells. *Blood*. Feb. 1, 2000;95(3):999-1006.
Englisch U et al., Chemically modified oligonucleotides as probes and inhibitors. *Angew Chemie Int Ed Engl*. Jun. 1991;30(6);613-29.
Erb KJ et al., Infection of mice with *Mycobacterium bovis*-Bacillus Calmette-Guerin (BCG) suppresses allergen-induced airway eosinophilia. *J Exp Med*. Feb. 16, 1998;187(4):561-9.
Etlinger HM, Carrier sequence selection—one key to successful vaccines. *Immunol Today*. Feb. 1992;13(2);52-5.
Froehler BC et al., Synthesis of DNA via deoxynucleoside H-phosphonate intermediates. *Nucleic Acids Res*. Jul. 11, 1986;14(13);5399-407.
Gaffney BL et al., Large-scale oligonucleotide synthesis by the H-phosphonate method. *Tetrahedron Lett* 29:2619-22 (1988).
Garegg PJ et al., Nucleoside H-phosphonates. III. Chemical synthesis of oligodeoxyribonucleotides by the hydrogenphosphonate approach. *Tetrahedron Lett* 27:4051-4 (1986).
Garegg PJ et al., Nucleoside H-phosphonates. IV. Automated solid phase synthesis of oligoribonucleotides by the hydrogenphosphonate approach. *Tetrahedron Lett* 27:4055-8 (1986).
Goodchild J, Conjugates of oligonucleotides and modified oligonucleotides: a review of their synthesis and properties. *Bioconjugate Chem* 1:165-87 (1990).
Gura T, Antisense has growing pains. *Science*. Oct. 27, 1995;270(5236):575-7.
Hadden JW et al., Immunopharmacology. Immunomodulation and immunotherapy. *JAMA*. Nov. 25, 1992;268(20);2964-9.
Hadden JW, Immunostimulants. *Trends Pharmacol Sci*. May 1993;14(5):169-74.
Halpern MD et al., Bacterial DNA induces murine interferon-gamma production by stimulation of interleukin-12 and tumor necrosis factor-alpha. *Cell Immunol*. Jan. 10, 1996;167(1);72-8.
Hartmann G et al., Mechanism and function of a newly identified CpG DNA motif in human primary B cells. *J Immunol*. Jan. 15, 2000;164(2):944-53.
Hartmann G et al., Spontaneous and cationic lipid-mediated uptake of antisense oligonucleotides in human monocytes and lymphocytes. *J Pharmacol Exp Ther*. May 1998; 285(2):920-8.
Hatzfeld J et al., Release of early human hematopoietic progenitors from quiescence by antisense transforming growth factor beta 1 or Rb oligonucleotides. *J Exp Med*. Oct. 1,1991;174(4):925-9.
Hazenbos WLW et al., Murine IgG1 complexes trigger immune effector functions predominantly via Fc gamma RIII (CD16). *J Immunol*. Sep. 15, 1998;161(6):3026-32.
Highfield PE, Sepsis: the more, the murkier. *Biotechnology (NY)*. Aug. 1994;12(8):828.
Hoeffler JP et al., Identification of multiple nuclear factors that interact with cyclic adenosine 3'5'-monophosphate response element-binding protein and activating transcription factor-2 by protein-protein interactions. *Mol Endocrinol*. Feb. 1991;5(2):256-66.
Iguchi-Ariga SM et al., CpG methylation of the cAMP-responsive enhancer/promoter sequence TGACGTCA abolishes specific factor binding as well as transcriptional activation. *Genes Dev*. May 1989;3(5):612-9.
Ishikawa R et al., IFN induction and associated changes in splenic leukocyte distribution. *J Immunol*. May 1, 1993;150(9):3713-27.
Iversen PL et al., Pharmacokinetics of an antisense phosphorothioate oligodeoxynucleotide against rev from human immunodeficiency virus type 1 in adult male rat following single injections and continuous infusion. *Antisense Res Dev*. 1994 Spring;4(1);43-52.
Jakobovits A et al., Analysis of homozygous mutant chimeric mice: deletion of the immunoglobulin heavy-chain joining region blocks B-cell development and antibody production. *Proc Natl Acad Sci USA*. Mar. 15, 1993;90(6):2551-5.
Jakway JP et al., Growth regulation of the B lymphoma cell line WEHI-231 by anti-immunoglobulin, lipopolysaccharide, and other bacterial products. *J Immunol*. Oct. 1, 1986;137(7);2225-31.
Jaroszewski JW et al., Cellular uptake of antisense oligodeoxynucleotides. *Adv Drug Del Rev* 1991; 6(3):235-50.

Kataoka T et al., Antitumor activity of synthetic oligonucleotides with sequences from cDNA encoding proteins of *Mycobacterium bovis* BCG. *Jpn J Cancer Res.* Mar. 1992;83(3):244-7.

Kataoka T et al., Immunotherapeutic potential in guinea-pig tumor model of deoxyribonucleic acid from *Mycobacterium bovis* BCG complexed with poly-L-lysine and carboxymethycellulose. *Jpn J Med Sci Biol.* Oct. 1990;43(5):171-82.

Kimura Y et al., Binding of oligoguanylate to scavenger receptors is required for oligonucleotides to augment NK cell activity and induce IFN. *J Biochem* (Tokyo). Nov. 1994;116(5):991-4.

Klinman DM et al., Contribution of CpG motifs to the immunogenicity of DNA vaccines. *J Immunol.* Apr. 15, 1997;158(8):3635-9.

Klinman DM et al., Immune recognition of foreign DNA: a cure for bioterrorism? *Immunity.* Aug. 1999;11(2):123-9.

Krieg AM et al., A role for endogenous retroviral sequences in the regulation of lymphocyte activation. *J Immunol.* Oct. 15, 1989;143(8):2448-51.

Krieg AM et al., CpG motifs in bacterial DNA trigger direct B-cell activation. *Nature.* Apr. 6, 1995;374(6522):546-9.

Krieg AM et al., Leukocyte stimulation by oligodeoxynucleotides. In: *Applied Antisense Oligonucleotide Technology,* Stein CA and Krieg AM, eds., New York: Wiley-Liss, 1998; pp. 431-438.

Krieg AM et al., Mechanism of action of CpG DNA. *Curr Top Microbiol Immunol.* 2000;247:1-21.

Krieg AM et al., Mechanisms and therapeutic applications of immune stimulatory CpG DNA. *Pharmacol Ther.* Nov. 1999;84(2):113-20.

Krieg Am et al., Modification of antisense phosphodiester oligodeoxynucleotides by a 5' cholesteryl moiety increases cellular association and improves efficacy. *Proc Natl Acad Sci U S A.* Feb. 1, 1993; 90(3);1048-52.

Krieg Am et al., Oligodeoxynucleotide modifications determine the magnitude of B cell stimulation by CpG motifs. *Antisense Nucleic Acid Drug Dev.* 1996 Summer;6(2):133-9.

Krieg AM et al., Phosphorothioate oligodeoxynucleotides: antisense or anti-protein? *Antisense Res Dev.* 1995 Winter;5(4);241.

Krieg AM et al., The role of CpG dinucleotides in DNA vaccines. *Trends Microbiol.* Jan. 1998;6(1):23-7.

Krieg AM et al., Uptake of oligodeoxyribonucleotides by lymphoid cells is heterogeneous and inducible. *Antisense Res Dev.* 1991 Summer;1(2):161-71.

Krieg AM, An innate immune defense mechanism based on the recognition of CpG motifs in microbial DNA. *J Lab Clin Med.* Aug. 1996;128(2):128-33.

Krieg AM, CpG DNA: a pathogenic factor in systemic lupus erythematosus? *J Clin Immunol.* Nov. 1995;15(6):284-92.

Krieger M et al., Structures and functions of multiligand lipoprotein receptors: macrophage scavenger receptors and LDL receptor-related protein (LRP). *Annu Rev Biochem.* 1994;63:601-37.

Kuramoto E et al., Oligonucleotide sequences required for natural killer cell activation. *Jpn J Cancer Res.* Nov. 1992;83(11):1128-31.

Lagneaux L et al., Chronic lymphocytic leukemic B cells but not normal B cells are rescued from apoptosis by contact with normal bone marrow stromal cells. *Blood.* Apr. 1, 1998; 91(7);2387-96.

Lipford GB et al., Bacterial DNA as immune cell activator. *Trends Microbiol.* Dec. 1998;6(12);496-500.

Lipford GB et al., CpG-containing synthetic oligonucleotides promote B and cytotoxic T cell responses to protein antigen: a new class of vaccine adjuvants. *Eur J Immunol.* Sep. 1997;27(9):2340-4.

Lipford GB et al., Immunostimulatory DNA: sequence-dependent production of potentially harmful or useful cytokines. *Eur J Immunol.* Dec. 1997;27(12);3420-6.

Lyons AB et al., Determination of lymphocytic division by flow cytometry. *J Immunol Methods.* May 2 1994;171(1):131-7.

Macaya RF et al., Thrombin-binding DNA aptamer forms a unimolecular quadruplex structure in solution. *Proc Natl Acad Sci USA.* Apr. 15, 1993;90(8):3745-9.

Macfarlane DE et al., Antagonism of immunostimulatory CpG-oligodeoxynucleotides by quinacrine, chloroquine, and structurally related compounds. *J Immunol.* Feb. 1, 1988; 160(3):1122-31.

Manzel L et al., CpG-oligodeoxynucleotide-resistant variant of WEHI 231 cells. *J Leukoc Biol.* Nov. 1999;66(5):817-21.

Mastrangelo MJ et al., Gene therapy for human cancer: an essay for clinicians. *Semin Oncol.* Feb. 1996;23(1):4-21.

Matson S et al., Nonspecific suppression of [3H]thymidine incorporation by "control" oligonucleotides. *Antisense Res Dev.* 1992 Winter;2(4);325-30.

McIntyre KW et al., A sense phosphorothioate oligonucleotide directed to the initiation codon of transcription factor NF-kappa B p65 causes sequence-specific immune stimulation. *Antisense Res Dev.* 1993 Winter;3(4):309-22.

Messina JP et al., Stimulation of in vitro murine lymphocyte proliferation by bacterial DNA. *J Immunol.* Sep. 15, 1991;147(6):1759-64.

Messina JP et al., The influence of DNA structure on the in vitro stimulation of murine lymphocytes by natural and synthetic polynucleotide antigens. *Cell Immunol.* Mar. 1993;147(1):148-57.

Mojcik CF et al., Administration of a phosphorothioate oligonucleotide antisense to murine endogenous retroviral MCF env causes immune effects in vivo in a sequence-specific manner. *Clin Immunol Immunopathol.* May 1993;67(2):130-6.

Moldoveanu Z et al., CpG DNA, a novel immune enhancer for systemic and mucosal immunization with influenza virus. *Vaccine.* Jul. 1998; 16(11-12):1216-24.

Mottram JC et al., A novel CDC2-related protein kinase from *Leishmania mexicana,* LmmCRK1, is post-translationally regulated during the life cycle. *J Biol Chem.* Oct. 5, 1993;268(28):21044-52.

NYCE JW et al., DNA antisense therapy for asthma in an animal model. *Nature.* Feb. 20, 1997;385(6618):721-5.

Paca-Uccaralertkun S et al., In vitro selection of DNA elements highly responsive to the human T-cell lymphotropic virus type I transcriptional activator, Tax. *Mol Cell Biol.* Jan. 1994;14(1):456-62.

Pisetsky DS et al., Stimulation of in vitro proliferation of murine lymphocytes by synthetic oligodeoxynucleotides. *Mol Biol Rep.* Oct. 1993;18(3);217-21.

Pisetsky DS et al., Stimulation of murine lymphocyte proliferation by a phosphorothioate oligonucleotide with antisense activity for herpes simplex virus. *Life Sci.* 1994;54(2):101-7.

Pisetsky DS et al., The influence of base sequence on the immunological properties of defined oligonucleotides. *Immunopharmacology.* Nov. 1998,40(3):199-208.

Pisetsky DS, Immunologic consequences of nucleic acid therapy. *Antisense Res Dev.* 1995 Fall;5(3):219-25.

Pisetsky DS, The immunologic properties of DNA. *J Immunol.* Jan. 15, 1996;156(2):421-3.

Raz E et al., Preferential induction of a Th1 immune response and inhibition of specific IgE antibody formation by plasmid DNA immunization. *Proc Natl Acad Sci USA.* May 14, 1996;93(10):5141-5.

Roman M et al., Immunostimulatory DNA sequences function as T helper-1-promoting adjuvants. *Nat Med.* Aug. 1997;3:849-54.

Sato Y et al., Immunostimulatory DNA sequences necessary for effective intradermal gene immunization. *Science.* Jul. 19, 1996;273(5273):352-4.

Schnell N et al., Identification and characterization of a *Saccharomyces cerevisiae* gene (PAR1) conferring resistance to iron chelators. *Eur J Biochem.* Sep. 1, 1991;200(2):487-93.

Shan D et al., Apoptosis of malignant human B cells by ligation of CD20 with monoclonal antibodies. *Blood.* Mar. 1, 1998;91(5):1644-52.

Shirakawa T et al., The inverse association between tuberculin responses and atopic disorder. *Science.* Jan. 3, 1997;275(5296):77-9.

Sparwasser T et al., Bacterial DNA and immunostimulatory CpG oligonucleotides trigger maturation and activation of murine dendritic cells. *Eur J Immunol.* Jun. 1998;28(6):2045-54.

Sparwasser T et al., Macrophages sense pathogens via DNA motifs: induction of tumor necrosis factor-alpha-mediated shock. *Eur J Immunol.* Jul 1997;27(7):1671-9.

Stec WJ et al., Diastereomers of nucleoside 3'-O-(2-thio-1,3,2-oxa(selena)phospholanes): building blocks for stereocontrolled synthesis of oligo(nucleoside phosphorothioate)s. *J Am Chem Soc.* Dec. 13, 1995;117(49):12019-29.

Stein CA et al., Oligodeoxynucleotides as inhibitors of gene expression: a review. *Cancer Res.* May 15, 1988, 48(10);2659-68.

Stull RA et al., Antigene, ribozyme and aptamer nucleic acid drugs: progress and prospects. *Pharm Res.* Apr. 1995;12(4):465-83.

Subramanian PS et al., Theoretical considerations on the "spine of hydration" in the minor groove of d(CGCGAATTCGCG). d(GCGCTTAAGCGC): Monte Carlo computer simulation. *Proc Natl Acad Sci U S A*. Mar. 1988;85(6):1836-40.

Sun S et al., Mitogenicity of DNA from different organisms for murine B cells. *J Immunol*. Oct. 1, 1997;159(7):3119-25.

Tanaka T et al., An antisense oligonucleotide complementary to a sequence in I gamma 2b increases gamma 2b germline transcripts, stimulates B cell DNA synthesis, and inhibits immunoglobulin secretion. *J Exp Med*. Feb. 1, 1992;175(2):597-607.

Threadgill DS et al., Mitogenic synthetic polynucleotides suppress the antibody response to a bacterial polysaccharide. *Vaccine*. Jan. 1998;16(1):76-82.

Tsukada J et al., Transcription factors NF-IL6 and CREB recognize a common essential site in the human prointerleukin 1 beta gene. *Mol Cell Biol*. Nov. 1994;14(11);7285-97.

Tutt AL et al., Monoclonal antibody therapy of B cell lymphoma: signaling activity on tumor cells appears more important than recruitment of effectors. *J Immunol*. Sep. 15, 1998;161(6):3176-85.

Uhlmann E et al., Antisense oligonucleotides: a new therapeutic principle. *Chem Rev*. Jun. 1990; 90(4):543-84.

Wagner RW, Gene inhibition using antisense oligodeoxynucleotides. *Nature*. Nov. 24, 1994;372(6504):333-5.

Wallace RB et al., Oligonucleotide probes for the screening of recombinant DNA libraries. *Methods Enzymol*. 1987;152:432-42.

Weiner GJ et al., Immunostimulatory oligodeoxynucleotides containing the CpG motif are effective as immune adjuvants in tumor antigen immunization. *Proc Natl Acad Sci USA*. Sep. 30, 1997;94(20):10833-7.

Wooldridge JE et al., Immunostimulatory oligodeoxynucleotides containing CpG motifs enhance the efficacy of monoclonal antibody therapy of lymphoma. *Blood*. Apr. 15, 1997;89(8):2994-8.

Wu GY et al., Receptor-mediated gene delivery and expression in vivo. *J Biol Chem*. Oct. 15, 1988;263(29):14621-4.

Wu-Pong S, Oligonucleotides: opportunities for drug therapy and research. *Pharm Technol*. Oct. 1994;18:102-14.

Wyatt JR et al., Combinatorially selected guanosine-quartet structure is a potent inhibitor of human immunodeficiency virus envelope-mediated cell fusion. *Proc Natl Acad Sci USA*. Feb. 15, 1994;91(4):1356-60.

Yamamoto S et al., Mode of action of oligonucleotide fraction extracted from *Mycobacterium bovis* BCG. *Kekkaku* 1994;69(9):29-32.

Yamamoto T et al., Lipofection of synthetic oligodeoxyribonucleotide having a palindromic sequence of AACGTT to murine splenocytes enhances interferon production and natural killer activity. *Microbiol Immunol*. 1994;38(10):831-6.

Yamamoto T et al., Synthetic oligonucleotides with certain palindromes stimulate interferon production of human peripheral blood lymphocytes in vitro. *Jpn J Cancer Res*. Aug. 1994;85(8):775-9.

Yi AK et al., IFN-gamma promotes IL-6 and IgM secretion in response to CpG motifs in bacterial DNA and oligodeoxynucleotides. *J Immunol*. Jan. 15, 1996;156(2):558-64.

Zhao Q et al., Comparison of cellular binding and uptake of antisense phosphodiester, phosphorothioate, and mixed phosphorothioate and methylphosphonate oligonucleotides. *Antisense Res Dev*. 1993 Spring;3(1):53-66.

Zhao Q et al., Stage-specific oligonucleotide uptake in murine bone marrow B-cell precursors. *Blood*. Dec. 1, 1994;84(11):3660-6.

Tokunaga T et al., Synthetic oligonucleotides with particular base sequences from the cDNA encoding proteins of *Mycobacterium bovis* BCG induce interferons and activate natural killer cells. *Microbiol Immunol*. 1992;36(1):55-66.

Tokunaga T et al., A synthetic single-stranded DNA, poly(dG,dC), induces interferon-alpha/beta and -gamma, augments natural killer activity, and suppresses tumor growth, *Jpn J Cancer Res*. Jun. 1988;79(6):682-6.

Yamamoto T et al., Ability of oligonucleotides with certain palindromes to induce interferon production and augment natural killer cell activity is associated with their base length. *Antisense Res Dev*. 1994 Summer;4(2):119-22.

Yamamoto S et al., DNA from bacteria, but not from vertebrates, induces interferons, activates natural killer cells and inhibits tumor growth. *Microbiol Immunol*. 1992;36(9):983-97.

Yamamoto S et al., In vitro augmentation of natural killer cell activity and production of interferon-alpha/beta and -gamma with deoxyribonucleic acid fraction from *Mycobacterium bovis* BCG. *Jpn J Cancer Res*. Jul. 1988;79(7):866-73.

Yamamoto S et al., Unique palindromic sequences in synthetic oligonucleotides are required to induce IFN and augment IFN-mediated natural killer activity. *J Immunol*. Jun.15, 1992;148(12):4072-6.

Jahrsdorfer B et al., CpG DNA increases primary malignant B cell expression of costimulatory molecules and target antigens. *J Leukoc Biol*. Jan. 2001;69(1):81-8.

Krieg AM et al., Applications of immune stimulatory CpG DNA for antigen-specific immunotherapy. *Eur J Cancer* 1999; 35 Supp 5:S10.

Warren TL et al., CpG oligodeoxynucleotides enhance monoclonal antibody therapy of a murine lymphoma. *Clin Lymphoma*. Jun. 2000;1(1):57-61.

Boerner P et al., Production of antigen-specific human monoclonal antibodies from in vitro-primed human splenocytes. *J Immunol*. Jul. 1, 1991;147(1):86-95.

Chaperot L et al., Functional expression of CD80 and CD86 allows immunogenicity of malignant B cells from non-Hodgkin's lymphomas. *Exp Hematol*. Mar. 1999;27(3):479-88.

Davis TA et al., Single-agent monoclonal antibody efficacy in bulky non-Hodgkin's lymphoma: results of a phase II trial of rituximab. *J Clin Oncol*. Jun. 1999;17(6):1851-7.

Davis TA et al., Therapy of B-cell lymphoma with anti-CD20 antibodies can result in the loss of CD20 antigen expression. *Clin Cancer Res*. Mar. 1999;5(3):611-5.

Elsasser D et al., HLA class II as potential target antigen on malignant B cells for therapy with bispecific antibodies in combination with granulocyte colony-stimulating factor. *Blood*. May 1, 1996;87(9):3803-12.

Foran JM et al., European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma. *J Clin Oncol*. Jan. 2000;18(2):317-24.

Funakoshi S et al., Inhibition of human B-cell lymphoma growth by CD40 stimulation. *Blood*. May 15, 1994;83(10):2787-94.

Ginaldi L et al., Levels of expression of CD19 and CD20 in chronic B cell leukaemias. *J Clin Pathol*. May 1998;51(5):364-9.

Gordon J et al., Regulation of survival in normal and neoplastic B lymphocytes. *Leukemia*. Aug. 1993;7 Suppl 2:S5-9.

Gordon J et al., Signals for survival and apoptosis in normal and neoplastic B lymphocytes. *Adv Exp Med Biol*. 1996;406:139-44.

Grillo-Lopez AJ et al, Overview of the clinical development of rituximab: first monoclonal antibody approved for the treatment of lymphoma. *Semin Oncol*. Oct. 1999;26(5 Suppl 14):66-73.

Higaki Y et al., Mechanisms involved in the inhibition of growth of a human B lymphoma cell line, B104, by anti-MHC class II antibodies. *Immunol Cell Biol*. Jun. 1994;72(3):205-14.

Jakobovits A et al., Germ-line transmission and expression of a human-derived yeast artificial chromosome. *Nature*. Mar. 18, 1993;362(6417):255-8.

Kinoshita T et al., CD20-negative relapse in B-cell lymphoma after treatment with Rituximab. *J Clin Oncol*. Dec. 1998;16(12)3916.

Kozbor D et al., A human hybrid myeloma for production of human monoclonal antibodies. *J Immunol*. Dec. 1984;133(6):3001-5.

Langer R, New methods of drug delivery. *Science*. Sep. 28, 1990;249(4976):1527-33.

Li X et al., Detection of apoptosis and DNA replication by differential labeling of DNA strand breaks with fluorochromes of different color. *Exp Cell Res*. Jan. 10, 1996;222(1):28-37.

Link BK et al., Anti-CD3-based bispecific antibody designed for therapy of human B-cell malignancy can induce T-cell activation by antigen-dependent and antigen-independent mechanisms. *Int J Cancer*. Jul. 17, 1998;77(2):251-6.

Link BK et al., Production and characterization of a bispecific IgG capable of inducing T-cell-mediated lysis of malignant B cells. *Blood*. Jun. 15, 1993;81(12):3343-9.

Maloney DG, Preclinical and phase I and II trials of rituximab. *Semin Oncol*. Oct. 1999;26(5 Suppl 14):74-8.

Martin-Orozco E et al., Enhancement of antigen-presenting cell surface molecules involved in cognate interactions by immunostimulatory DNA sequences. *Int Immunol*. Jul. 1999;11(7):1111-8.

Mayumi M et al., Negative signaling in B cells by surface immunoglobulins. *J Allergy Clin Immunol* Dec. 1996;98(6 Pt 2):S238-47.

McLaughlin P et al., Clinical status and optimal use of rituximab for B-cell lymphomas. *Oncology* (*Huntingt*). Dec. 1998;12(12):1763-9.

McLaughlin P et al., Rituximab in indolent lymphoma: the single-agent pivotal trial. *Semin Oncol*. Oct. 1999;26(5 Suppl 14):79-87.

Schultze JL et al., T cell mediated immunotherapy for B cell lymphoma. *J Mol Med*. Mar. 1999;77(3):322-31.

Wagner H, Bacterial CpG DNA activates immune cells to signal infectious danger. *Adv Immunol*. 1999;73:329-68.

Wagner RW et al., Potent and selective inhibition of gene expression by an antisense heptanucleotide. *Nat Biotechnol*. Jul. 1996;14(7):840-4.

Wahl RL et al., Improved radioimaging and tumor localization with monoclonal F(ab')2.*J Nucl Med*. Apr. 1983;24(4):316-25.

Wiseman GA et al., Radioimmunotherapy of relapsed non-Hodgkin's lymphoma with zevalin, a 90Y-labeled anti-CD20 monoclonal antibody. *Clin Cancer Res*. Oct. 1999;5(10 Suppl):3281s-3286s.

Witzig TE et al., Phase I/II trial of IDEC-Y2B8 radioimmunotherapy for treatment of relapsed or refractory CD20(+) B-cell non-Hodgkin's lymphoma. *J Clin Oncol*. Dec. 1999;17(12):3793-803.

Wooldridge JE et al., Select unmethylated CpG oligodeoxynucleotides improve antibody-dependent cellular cytotoxicity in vitro and in vivo. Abstract #3253. *Proc Am Assn Cancer Res* Mar. 1996;37:477.

Wooldridge JE et al., Select unmethylated CpG oligodeoxynucleotides improve antibody dependent cellular cytotoxicity in vitro of both murine and human B cell lymphomas. Abstract #2877. *Blood* Dec. 1995;86:722A.

Bauer M et al., DNA activates human immune cells through a CpG sequence-dependent manner. *Immunology*. Aug. 1999;97(4):699-705.

Hartmann G et al., CpG DNA: a potent signal for growth, activation, and maturation of human dendritic cells. *Proc Natl Acad Sci U S A*. Aug. 3, 1999;96(16):9305-10.

Macfarlane DE et al., Immunostimulatory CpG-oligodeoxynucleotides induce a factor that inhibits macrophage adhesion. *J Lab Clin Med*. Nov. 1999;134(5):501-9.

Sun S et al, Type I interferon-mediated stimulation of T cells by CpG DNA. *J Exp Med*. Dec. 21, 1998;188(12):2335-42.

\* cited by examiner

METHODS FOR ENHANCING ANTIBODY-INDUCED CELL LYSIS AND TREATING CANCER

PRIORITY

This application claims the benefit of U.S. Provisional Application No. 60/213,346, filed Jun. 22, 2000.

FIELD OF THE INVENTION

The invention relates to the treatment and prevention of cancer using immunostimulatory nucleic acids and antibodies.

BACKGROUND OF THE INVENTION

Cancer is the second leading cause of death, resulting in one out of every four deaths in the United States. In 1997, the estimated total number of new diagnoses for lung, breast, prostate, colorectal and ovarian cancer was approximately two million. Due to the ever increasing aging population in the United States, it is reasonable to expect that rates of cancer incidence will continue to grow.

Cancer is a disease which involves the uncontrolled growth (i.e., division) of cells. Some of the known mechanisms which contribute to the uncontrolled proliferation of cancer cells include growth factor independence, failure to detect genomic mutation, and inappropriate cell signaling. The ability of cancer cells to ignore normal growth controls may result in an increased rate of proliferation. Although the causes of cancer have not been firmly established, there are some factors known to contribute, or at least predispose a subject, to cancer. Such factors include particular genetic mutations (e.g., BRCA gene mutation for breast cancer, APC for colon cancer), exposure to suspected cancer-causing agents, or carcinogens (e.g., asbestos, UV radiation) and familial disposition for particular cancers such as breast cancer.

Cancer is currently treated using a variety of modalities including surgery, radiation therapy and chemotherapy. The choice of treatment modality will depend upon the type, location and dissemination of the cancer. For example, surgery and radiation therapy may be more appropriate in the case of solid well-defined tumor masses and less practical in the case of non-solid tumor cancers such as leukemia and lymphoma. One of the advantages of surgery and radiation therapy is the ability to control to some extent the impact of the therapy, and thus to limit the toxicity to normal tissues in the body. However, surgery and radiation therapy are often followed by chemotherapy to guard against any remaining or radio-resistant cancer cells. Chemotherapy is also the most appropriate treatment for disseminated cancers such as leukemia and lymphoma as well as metastases.

More recently, the use of CpG containing nucleic acids has been proposed for the treatment and prevention of cancer. We have found that unmethylated CG-dinucleotides within certain sequence contexts (CpG DNA) are recognized by the vertebrate immune system as foreign DNA (bacterial or viral). CpG DNA activates a coordinated set of immune responses that include innate immunity (macrophages, dendritic cells, and natural killer cells), humoral immunity, and cellular immunity. Krieg A M et al., *Pharmacol Ther* 84:113-20 (1999); Krieg A M et al., *Curr Top Microbiol Immunol* 247:1-21 (2000); Wagner H, *Adv Immunol* 73:329-68 (1999). As a vaccine adjuvant, CpG DNA is at least as effective as the gold standard complete Freund's adjuvant (CFA), but induces higher Th1 activity and demonstrates less toxicity. Chu R S et al., *J Exp Med* 186:1623-31 (1997); Weiner G J et al., *Proc Natl Acad Sci USA* 94:10833-7 (1997); Roman M et al., *Nat Med* 3:849-54 (1997); Lipford G B et al., *Eur J Immunol* 27:2340-4 (1997); Davis H L et al., *J Immunol* 160:870-6 (1998). Recently, we identified a human CpG motif which triggers proliferation and activation of primary human B cells. Hartmann G et al., *J Immunol* 164:944-53 (2000).

SUMMARY OF THE INVENTION

The invention relates in some aspects to methods for treating and preventing cancer using immunostimulatory nucleic acids and antibodies. Thus in one aspect the invention is a method for treating or preventing cancer. The method involves administering to a subject having or at risk of developing cancer an effective amount to upregulate CD20 expression of a nucleic acid, and an anti-CD20 antibody. The cancer, in some embodiments, is B-cell lymphoma associated with low levels of CD20 expression. The B-cell lymphoma in other embodiments is B-cell chronic lymphocytic leukemia (B-CLL) or a marginal zone lymphoma. In some embodiments the CD20 antibody is C2B8 or Rituximab.

The invention in other aspects relates to a method for diagnosing lymphoma by isolating a B cell from a subject and identifying a change in cell surface markers when the B cell is contacted with an immunostimulatory nucleic acid, wherein the cell surface marker induced on the B cell is indicative of the type of lymphoma. In some embodiments the subject has a type of lymphoma. In some embodiments the subject is suspected of having a type of lymphoma. The method may optionally include a method for treating cancer by administering to the subject an immunostimulatory nucleic acid and an antibody specific for the cell surface antigens induced on the B cell in order to treat the cancer.

In another aspect the invention is a method for treating or preventing cancer by administering to a subject having or at risk of developing cancer an effective amount to induce expression of a surface antigen on a cancer cell surface, of a nucleic acid, and administering to the subject an antibody selected from the group consisting of an anti-CD22 antibody and an anti-CD19 antibody.

According to another aspect of the invention, a method for treating lymphoma is provided. The method includes the steps of isolating a B cell from a subject having lymphoma, identifying a surface antigen which is not expressed or which is expressed on the surface of the B cell in an amount lower than that of a control B cell, administering to the subject an antibody specific for the identified surface antigen and an immunostimulatory nucleic acid in order to treat the lymphoma, wherein the nucleic acid is administered in an effective amount to upregulate expression of the surface antigen on the lymphoma cell surface.

A method for treating a lymphoma resistant to antibody therapy is provided according to another aspect of the invention. The method includes administering to a subject having a lymphoma resistant to therapy with an antibody specific for a surface antigen, an antibody specific for the surface antigen to which the lymphoma is resistant and a nucleic acid in order to treat the lymphoma, wherein the nucleic acid is administered in an effective amount to upregulate expression of the surface antigen on the lymphoma cell surface.

The surface antigen may be any type of surface antigen which is capable of being expressed on the surface of a cancer cell and which is induced by stimulation with immunostimulatory nucleic acids. In some embodiments the surface antigen is CD20, CD40, CD22, or CD19. In other embodiments the lymphoma is B-CLL or marginal zone lymphoma. In some embodiments the antibody is an anti-CD20 antibody. In some embodiments the anti-CD20 antibody is C2B8. In another embodiment the anti-CD20 antibody is Rituximab.

In some preferred embodiments the antibody is a human IgG1 antibody. In some preferred embodiments the antibody is a murine IgG2a antibody.

In some embodiments the methods also include administering an anti-cancer therapy to the subject.

The invention also includes a method for treating cancer in a human by administering to a human an immunostimulatory nucleic acid and an antibody of IgG1 isotype (an IgG1 isotype antibody as used herein refers to a human or humanized IgG1 unless otherwise specified), which binds to a cell surface antigen of a cancer cell and wherein the nucleic acid and the antibody are administered in an effective amount for killing the cancer cell.

Optionally the nucleic acid and the antibody are administered together. Alternatively the nucleic acid and the antibody may be administered separately.

In some embodiments the method includes the step of administering a cancer therapy. As used herein the term "a cancer therapy" is meant to embrace a single medicament, a plurality of medicaments of a particular class and a plurality of medicaments of different classes, and includes but is not limited to chemotherapeutic agents, cancer vaccines, biological response modifiers, and hormone therapies.

A chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as Melphalan, Cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP 16-213), Floxuridine, Fluorouracil (5-FU), Flutamide, Hydroxyurea (hydroxycarbamide), Ifosfamide, Interferon Alfa-2a, Interferon Alfa-2b, Leuprolide acetate (LHRH-releasing factor analogue), Lomustine (CCNU), Mechlorethamine HCl (nitrogen mustard), Mercaptopurine, Mesna, Mitotane (o,p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erythropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In some preferred embodiments the chemotherapeutic agent may be selected from the group consisting of methotrexate, vincristine, adriamycin, cisplatin, mitomycin C, bleomycin, doxorubicin, dacarbazine, taxol, valrubicin, Novantrone/Mitroxantrone, Evacet/liposomal doxorubicin, Yewtaxan/Paclitaxel, Taxol/Paclitaxel, SPU-077/Cisplatin, HMR 1275/Flavopiridol, BMS-182751/oral platinum, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, Caetyx/liposomal doxorubicin, Gemzar/Gemcitabine, Ifes/Mesnex/Ifosamide, Vumon/Teniposide, Paraplatin/Carboplatin, Plantinol/cisplatin, Vepeside/Etoposide, Taxotere/Docetaxel, prodrug of guanine arabinoside, nitrosoureas, alkylating agents such as melphalan and cyclophosphamide, Asparaginase, Busulfan, Carboplatin, Chlorombucil, Cytarabine HCl, Daunorubicin HCl, Etoposide (VP16-213), Hydroxyurea (hydroxycarbamide), Ifosfamide, Interferon Alfa-2a, Interferon Alfa-2b, Lomustine (CCNU), Mechlorethamine HCl (nitrogen mustard), Mercaptopurine, Mitoxantrone HCl, Procarbazine HCl, Thioguanine, Thiotepa, Vinblastine sulfate, Azacitidine, Interleukin 2, Pentostatin (2'deoxycoformycin), Teniposide (VM-26), GM-CSF, and Vindesine sulfate.

A cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys. Biological response modifiers include interferon, and lymphokines such as IL-2. Hormone replacement therapy includes tamoxifen alone or in combination with progesterone. In a further embodiment, the cancer therapy is interferon-α (e.g., INTRON® A, Schering).

The cancer may be selected from the group consisting of basal cell carcinoma, bladder cancer, bone cancer, brain and central nervous system (CNS) cancer, breast cancer, cervical cancer, colon and rectum cancer, connective tissue cancer, esophageal cancer, eye cancer, kidney cancer, larynx cancer, leukemia, liver cancer, lung cancer, Hodgkin's lymphoma, non-Hodgkin's lymphoma, melanoma, myeloma, oral cavity cancer (e.g., lip, tongue, mouth, and pharynx), ovarian cancer, pancreatic cancer, prostate cancer, rhabdomyosarcoma, skin cancer, stomach cancer, testicular cancer, and uterine cancer. In preferred embodiments, the cancer to be treated may be selected from the group consisting of bone cancer, brain and CNS cancer, connective tissue cancer, esophageal cancer, eye cancer, Hodgkin's lymphoma, larynx cancer, oral cavity cancer (e.g., lip, tongue, mouth, and pharynx), skin cancer, and testicular cancer.

In another aspect the invention encompasses a kit. The kit includes a package including at least two containers, the first container housing an immunostimulatory nucleic acid, the second container housing an antibody specific for a cell surface antigen, and instructions for screening a cell to determine whether the immunostimulatory nucleic acid upregulates expression of the cell surface antigen. In one embodiment the antibody is selected from the group consisting of an anti-CD20 antibody, an anti-CD19 antibody, and an anti-CD22 antibody.

The nucleic acids useful according to the invention are immunostimulatory nucleic acids and in some embodiments are immunostimulatory CpG nucleic acids having an unmethylated CpG motif, immunostimulatory T-rich nucleic acids, immunostimulatory poly-G nucleic acids, bacterial DNA, yeast DNA, or eukaryotic DNA.

In some embodiments the nucleic acid does not hybridize with genomic DNA or RNA under stringent conditions. In other embodiments the nucleic acid does hybridize with genomic DNA or RNA under stringent conditions.

The nucleic acid may have natural linkages or may include at least one modified backbone internucleotide linkage. In some embodiments the modified backbone is a phosphate backbone modification. In other embodiments the modified backbone is a peptide modified oligonucleotide backbone. The nucleic acid may also include native bases or modified bases. The nucleotide backbone may be chimeric, or the nucleotide backbone is entirely modified.

The immunostimulatory nucleic acid can have any length greater than 6 nucleotides, but in some embodiments is between 8 and 100 nucleotide residues in length. In other embodiments the nucleic acid comprises at least 20 nucleotides, at least 24 nucleotides, at least 27, nucleotides, or at least 30 nucleotides. The nucleic acid may be single-stranded or double-stranded. In some embodiments the nucleic acid is isolated and in other embodiments the nucleic acid may be a synthetic nucleic acid.

The CpG nucleic acid in one embodiment contains at least one unmethylated CpG dinucleotide having a sequence including at least the following formula: 5' $X_1X_2CGX_3X_4$ 3' wherein C is unmethylated, wherein $X_1$, $X_2$, $X_3$, and $X_4$ are nucleotides. In one embodiment the 5' $X_1X_2CGX_3X_4$ 3' sequence of the CpG nucleic acid is a non-palindromic sequence, and in other embodiments it is a palindromic sequence.

In some embodiments $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA. In other embodiments $X_1X_2$ are GpA or GpT and $X_3X_4$ are TpT. In yet other embodiments $X_1$ or $X_2$ or both are purines and $X_3$ or $X_4$ or both are pyrimidines or $X_1X_2$ are GpA and $X_3$ or $X_4$ or both are pyrimidines. In one embodiment $X_2$ is a T and $X_3$ is a pyrimidine.

In other embodiments the CpG nucleic acid has a sequence selected from the group consisting of SEQ ID NOs: 19, 35-37, 39-42, 91, 92, 101, 108, 111, 135, 141, 151, 274, 277, 280, 286, 319, 350, 363, 368, 375, 495-498, 517, 518, 524, 529, 545, 548, 549, 555, 557, 560-563, 566, 585, 590, 591, 595, 599, 603, 605, 611, 614-616, 650, 676, 679, 682, 684, 702, 703, 707-710, 717-720, 729-732, 752, 755, 770, and 801-803.

In some embodiments the T-rich immunostimulatory nucleic acid is a poly-T nucleic acid comprising 5' TTTT 3'. In yet other embodiments the poly-T nucleic acid comprises 5' $X_1X_2TTTTX_3X_4$ 3' wherein $X_1$, $X_2$, $X_3$, and $X_4$ are nucleotides. In some embodiments $X_1X_2$ is TT and/or $X_3X_4$ is TT. In other embodiments $X_1X_2$ is selected from the group consisting of TA, TG, TC, AT, AA, AG, AC, CT, CC, CA, CG, GT, GG, GA, and GC; and/or $X_3X_4$ is selected from the group consisting of TA, TG, TC, AT, AA, AG, AC, CT, CC, CA, CG, GT, GG, GA, and GC.

The T-rich immunostimulatory nucleic acid may have only a single poly-T motif or it may have a plurality of poly-T nucleic acid motifs. In some embodiments the T-rich immunostimulatory nucleic acid comprises at least 2, at least 3, at least 4, at least 5, at least 6, at least 7, or at least 8 T motifs. In other embodiments it comprises at least 2, at least 3, at least 4, at least 5, at least 6, at least 7, or at least 8 CpG motifs. In some embodiments the plurality of CpG motifs and poly-T motifs are interspersed.

In yet other embodiments at least one of the plurality of poly-T motifs comprises at least 3, at least 4, at least 5, at least 6, at least 7, at least 8, or at least 9 contiguous T nucleotide residues. In other embodiments the plurality of poly-T motifs is at least 3 motifs and wherein at least 3 motifs each comprises at least 3 contiguous T nucleotide residues or the plurality of poly-T motifs is at least 4 motifs and wherein the at least 4 motifs each comprises at least 3 contiguous T nucleotide residues.

The T-rich immunostimulatory nucleic acid may include one or more CpG motifs. In other embodiments the T-rich immunostimulatory nucleic acid is free of one or more CpG dinucleotides.

In other embodiments the T-rich immunostimulatory nucleic acid has poly A, poly-G, and/or poly C motifs. In other embodiments the T-rich immunostimulatory nucleic acid is free of two poly C sequences of at least 3 contiguous C nucleotide residues. Preferably the T-rich immunostimulatory nucleic acid is free of two poly A sequences of at least 3 contiguous A nucleotide residues. In other embodiments the T-rich immunostimulatory nucleic acid comprises a nucleotide composition of greater than 25% C or greater than 25% A. In yet other embodiments the T-rich immunostimulatory nucleic acid is free of poly-C sequences, poly-G sequences or poly-A sequences.

In some cases the T-rich immunostimulatory nucleic acid may be free of poly-T motifs, but rather, comprises a nucleotide composition of greater than 25% T. In other embodiments the T-rich immunostimulatory nucleic acid may have poly-T motifs and also comprise a nucleotide composition of greater than 25% T. In some embodiments the T-rich immunostimulatory nucleic acid comprises a nucleotide composition of greater than 25% T, greater than 30% T, greater than 40% T, greater than 50% T, greater than 60% T, greater than 80% T, or greater than 90% T nucleotide residues.

In some embodiments the poly-G nucleic acid comprises: 5' $X_1X_2GGGX_3X_4$ 3' wherein $X_1$, $X_2$, $X_3$, and $X_4$ are nucleotides. In embodiments at least one of $X_3$ and $X_4$ are a G or both of $X_3$ and $X_4$ are a G. In other embodiments the poly-G nucleic acid comprises the following formula: 5' GGGNGGG 3' wherein N represents between 0 and 20 nucleotides. In yet other embodiments the poly-G nucleic acid comprises the following formula: 5' GGGNGGGNGGG 3' (SEQ ID NO:849) wherein N represents between 0 and 20 nucleotides.

The poly-G immunostimulatory nucleic acid may include one or more CpG motifs or T-rich motifs. In other embodiments the poly-G nucleic acid is free of one or more CpG dinucleotides or poly-T motifs.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Figure 1A:
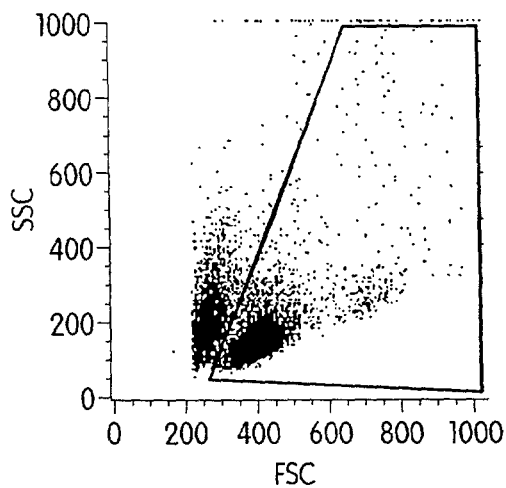
FIG. 1 depicts data from flow cytometry which demonstrates the induction of a morphologic change in marginal zone lymphoma cells upon CpG oligonucleotide stimulation. Malignant B cells from a patient with marginal zone lymphoma were stimulated with no oligonucleotide (A and D), control oligonucleotide (ODN 2017, SEQ ID NO: 168, B and E) or CpG oligonucleotide (ODN 2006, SEQ ID NO: 729, C and F) and analyzed by flow cytometry. A, B, and C illustrate forward scatter (FSC; x-axis) vs. side scatter (SSC; y-axis). D, E and F illustrate CD19 expression (x-axis) against FSC (y-axis).
Figure 1D:
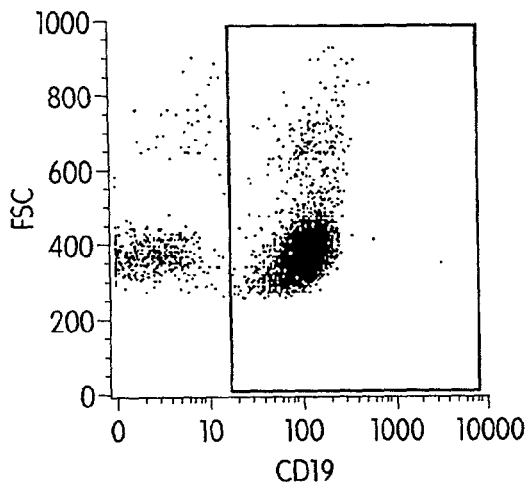
Figure 1B:
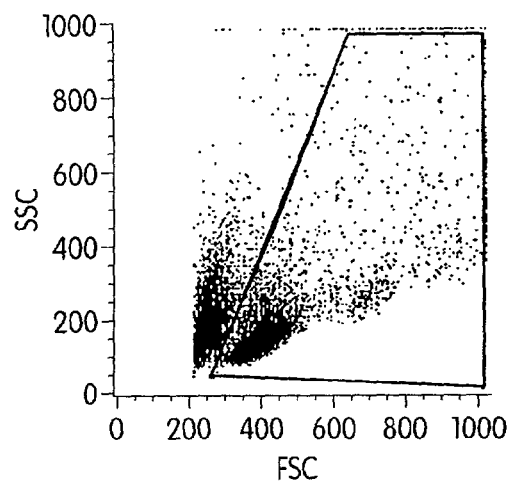
Figure 1E:
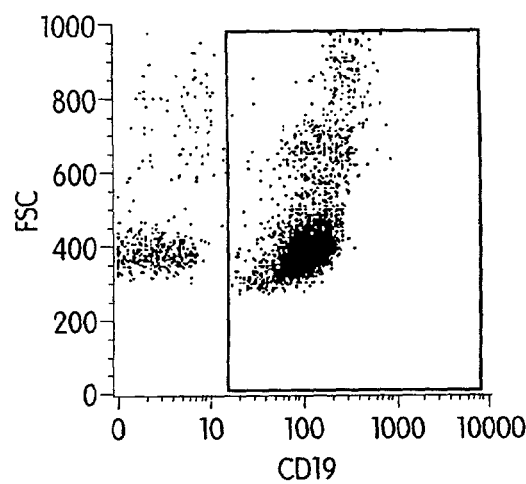
Figure 1C:
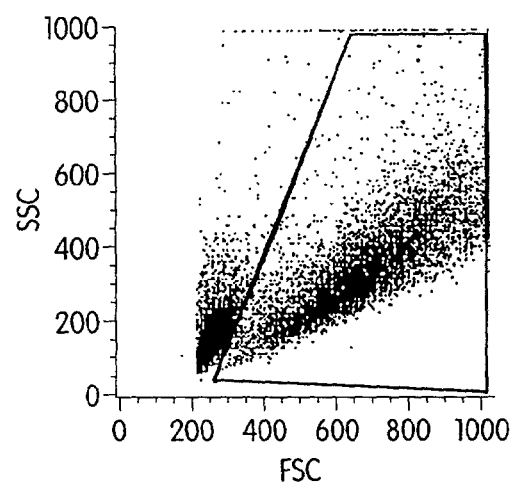
Figure 1F:
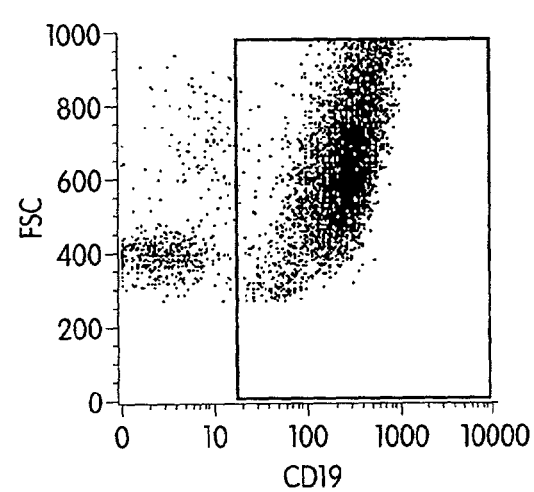

Present cancer treatments are often ineffective as well as being associated with a high degree of patient morbidity. The invention provides methods and products for the more effective treatment of cancer using a combination of immunostimulatory nucleic acids, antibodies, and optionally cancer therapies.

The invention is based, in part, on the surprising discovery that administration to a subject of immunostimulatory nucleic acids induces the expression of cell surface antigens including CD20, CD19, and CD22 on the surface of a cancer cell and that the induction of these antigens leads to enhanced antibody-dependent cellular cytotoxicity (ADCC). It was previously believed that CpG oligonucleotides enhanced ADCC by influencing the effector cell (e.g., by activating natural killer (NK) cells). Now it has been discovered according to the invention that immunostimulatory nucleic acids actually cause the induction of specific antigens CD20, CD19, and CD22, each of which can be targeted by specific antibody therapies. The discovery that immunostimulatory nucleic acids are capable of upregulating expression of certain target antigens on the surface of cancer cells, supports the development of therapies using immunostimulatory nucleic acids in combination with specific antibodies which interact with these cell surface antigens. Thus, in one aspect, the invention provides a method for treating or preventing cancer which involves the administration to a subject of a combination of an immunostimulatory nucleic acid and an antibody which specifically interacts with CD20, CD19, and CD22 in an effective amount to prevent or treat the cancer.

Additionally, it was discovered that the increased expression of these and other cell surface antigens varies widely depending upon the histological state of the tumor cell studied. The effect of immunostimulatory nucleic acids on different types of primary malignant B cells and reactive follicular hyperplasia was extensively examined. All B-cell lymphoma cells tested increased in size and granularity, upregulated activation markers (CD80, CD86, CD40, CD54, CD69), and upregulated antigen presentation molecules (class I major histocompatibility complex (MHC I), class II major histocompatibilty complex (MHC II)) in response to immunostimulatory nucleic acids. A control poly-C oligodeoxynucleotide (ODN) showed only minor effects. The extent of phenotypic change induced by immunostimulatory nucleic acids differed from sample to sample. Immunostimulatory nucleic acids, but not control nucleic acids, increased the expression of co-stimulatory molecules (e.g., CD40, CD80, CD86, CD54) on malignant B cells without altering the phenotype of B cells derived from reactive follicular hyperplasia. Immunostimulatory nucleic acids also enhanced expression of both class I and class II MHC in most samples. CD20 expression was increased in response to immunostimulatory nucleic acids, most notably in B-CLL and marginal zone lymphoma.

Furthermore, an inverse correlation was found between baseline expression of specific cell surface antigens and their expression after exposure to immunostimulatory nucleic acids. Thus the most significant increase in expression of these molecules was found in those samples that had the lowest (or no) baseline levels. These data indicate that immunostimulatory nucleic acids may reverse low expression of co-stimulatory molecules on malignant B cells that correspond to a low level of activation, while their effects on cells that are already in an activated state are less profound.

Thus, the invention relates to methods for identifying an appropriate therapy for a lymphoma patient, and for treating the patient using that therapy. The method can be accomplished by isolating a B cell from a lymphoma patient and comparing the surface antigens expressed on the malignant B cell with those expressed on normal B cells. The antigens which are expressed in low levels or not at all on the malignant B cell can be identified. The subject can then be treated using a combination of an immunostimulating nucleic acid and an antibody which specifically recognizes the antigen(s) which are expressed in low levels or not at all on the malignant B cell.

The invention is also useful for treating cancers which are resistant to monoclonal antibody therapy. It has been discovered according to the invention, that immunostimulatory nucleic acids can reverse the resistance of tumor cells and render tumor cells which were previously non-responsive or only weakly responsive, sensitive to therapy. In particular it has been discovered that immunostimulatory nucleic acids can cause a phenotypic change to a resistant tumor cell that renders it sensitive to monoclonal antibody therapy. For instance, the monoclonal anti-CD20 antibody Rituximab has been shown to be effective clinically in several trials and has recently been approved for the therapy of follicular B cell lymphoma. Maloney D G, *Semin Oncol* 26:74-8 (1999); Foran J M et al., *J Clin Oncol* 18:317-24 (2000); Witzig T E et al., *J Clin Oncol* 17:3793-803 (1999); Davis T A et al., *J Clin Oncol* 17:1851-7 (1999); Wiseman G A et al., *Clin Cancer Res* 5:3281s-3286s (1999); Grillo-Lopez A J et al, *Semin Oncol* 26:66-73 (1999). There are reports that with lymphomas a small minority of tumors that re-emerge following Rituximab therapy can lack CD20 expression. Davis T A et al., *Clin Cancer Res* 5:611-5 (1999); Kinoshita T et al., *J Clin Oncol* 16:3916 (1998). The immunostimulatory nucleic acids of the invention are useful for treating this set of resistant tumors. Additionally, Rituximab has not been useful for the treatment of all types of B cell malignancies. Expression of CD20 is relatively low on B-CLL cells, which provides an explanation for why Rituximab is less effective for CLL than for some other B-cell malignancies. Grinaldi L et al., *J Clin Pathol* 51:364-9 (1998). The immunostimulatory nucleic acids of the invention are also useful for treating these tumors.

The humanized monoclonal antibody 1D10 recognizes an HLA-DR variant antigen. Link B K et al., *Blood* 81:3343-9 (1993). This antibody is currently being tested in a phase I clinical trial in patients with lymphoma. One limitation to the use of this antibody is that the target antigen is only expressed by approximately 50% of B-cell lymphomas. Interestingly, its expression was upregulated by immunostimulatory nucleic acids in all lymphoma samples tested. It was discovered according to the invention that immunostimulatory nucleic acids may enhance the efficacy of therapy with these and other antibodies by increasing expression of target antigen. Thus in another aspect the invention includes methods for treating lymphoma by administering to a subject an immunostimulatory nucleic acid and antibodies specific for HLA-DR. One useful antibody is the humanized monoclonal antibody 1D10. It is particularly useful for treating resistant tumors.

The invention also relates to the discovery of a specific subclass, or isotype, of antibody which when combined with immunostimulatory nucleic acids produces a synergistic immune response. Another subclass, or isotype, does not even provide an additive response when combined with immunostimulatory nucleic acids. It was discovered according to the invention that the combination of immunostimulatory nucleic acids and human antibodies of the IgG1 isotype results in an increased (synergistic) survival rate. When immunostimulatory nucleic acids are combined with human antibodies of the IgG2 isotype, no increase in survival rate is observed over the use of the IgG2 antibody alone. The IgG2 isotype (which correlates with the murine IgG1 isotype) is believed to be recognized by the Fc receptor designated CD16 that is expressed largely by NK cells. Immunostimulatory nucleic acids are known to activate NK cells, and thus, it is surprising that immunostimulatory nucleic acids do not enhance the therapeutic effect of human IgG2 or murine IgG1 antibodies. Since NK cells are believed to be involved in ADCC and are activated by immunostimulatory nucleic acids, it was surprising that antibodies of the human IgG2 (or murine IgG1) isotype do not produce a synergistic or even additive response when administered with immunostimulatory nucleic acids.

A cancer cell is a cell that divides and reproduces abnormally due to a loss of normal growth control. Cancer cells almost always arise from at least one genetic mutation. In some instances, it is possible to distinguish cancer cells from their normal counterparts based on profiles of expressed genes and proteins, as well as to the level of their expression. Genes commonly affected in cancer cells include oncogenes, such as ras, neu/HER2/erbB, myb, myc and abl, as well as tumor suppressor genes such as p53, Rb, DCC, RET and WT. Cancer-related mutations in some of these genes leads to a decrease in their expression or a complete deletion. In others, mutations cause an increase in expression or the expression of an activated variant of the normal counterpart.

The term "tumor" is usually equated with neoplasm, which literally means "new growth" and is used interchangeably with "cancer." A "neoplastic disorder" is any disorder associated with cell proliferation, specifically with a neoplasm. A "neoplasm" is an abnormal mass of tissue that persists and proliferates after withdrawal of the carcinogenic factor that initiated its appearance. There are two types of neoplasms, benign and malignant. Nearly all benign tumors are encapsulated and are noninvasive; in contrast, malignant tumors are almost never encapsulated but invade adjacent tissue by infiltrative destructive growth. This infiltrative growth can be followed by tumor cells implanting at sites discontinuous with the original tumor. The method of the invention can be used to treat neoplastic disorders in humans, including but not limited to: sarcoma, carcinoma, fibroma, glioma, leukemia, lymphoma, melanoma, myeloma, neuroblastoma, retinoblastoma, and rhabdomyosarcoma, as well as each of the other tumors described herein.

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia), ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma; biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

The immunostimulatory nucleic acids and antibodies are useful for treating or preventing cancer in a subject. A "subject" unless otherwise specified shall mean a human or vertebrate mammal including but not limited to a dog, cat, horse, cow, pig, sheep, goat, or primate, e.g., monkey. Thus the invention can be used to treat cancer and tumors in human and non human subjects. Cancer is one of the leading causes of death in companion animals (i.e., cats and dogs). Cancer usually strikes older animals which, in the case of house pets, have become integrated into the family. Forty-five percent of dogs older than 10 years of age are likely to succumb to the disease. The most common treatment options include surgery, chemotherapy and radiation therapy. Other treatment modalities which have been used with some success are laser therapy, cryotherapy, hyperthermia and immunotherapy. The choice of treatment depends on the type of cancer and degree of dissemination. Unless the malignant growth is confined to a discrete area in the body, it is difficult to remove only malignant tissue without also affecting normal cells.

Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilms' tumor, Burkitt's lymphoma, microglioma, neuroblastoma, osteoclastoma, oral neoplasia, fibrosarcoma, osteosarcoma and rhabdomyosarcoma. Other neoplasias in dogs include genital squamous cell carcinoma, transmissable venereal tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an evermore popular house pet, is known to develop insulinoma, lymphoma, sarcoma, neuroma, pancreatic islet cell tumor, gastric MALT lymphoma and gastric adenocarcinoma.

Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticuloendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lymphadenitis (CLA): chronic, infectious, contagious disease of sheep and goats caused by the bacterium Corynebacterium pseudotuberculosis, and contagious lung tumor of sheep caused by jaagsiekte.

In one aspect, a method for treating cancer is provided which involves administering the compositions of the invention to a subject having cancer. A "subject having cancer" is a subject that has been diagnosed with a cancer. In some embodiments, the subject has a cancer type characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual inspection or palpation methods, or by irregularity in shape, texture or weight of the tissue.

However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

With respect to the prophylactic treatment methods, the invention is aimed at administering the compositions of the invention to a subject at risk of developing cancer. A subject at risk of developing a cancer is one who has a high probability of developing cancer. These subjects include, for instance, subjects having a genetic abnormality, the presence of which has been demonstrated to have a correlative relation to a higher likelihood of developing a cancer. Subjects exposed to cancer-causing agents such as tobacco, asbestos, or other chemical toxins are also subjects at risk of developing cancers used herein. When a subject at risk of developing a cancer is treated with an immunostimulatory nucleic acid, an antibody and optionally a cancer therapy, on a regular basis, such as monthly, the cancer growth will be prevented from initiating. This aspect of the invention is particularly advantageous when the subjects employed in certain trades which are exposed to cancer-causing agents on an ongoing basis. For example, many airborne, or inhaled, carcinogens such as tobacco smoke and asbestos have been associated with lung cancer.

A carcinogen is an agent capable of initiating development of malignant cancers. Exposure to carcinogens generally increases the risk of neoplasms in subjects, usually by affecting DNA directly. Carcinogens may take one of several forms such as chemical, electromagnetic radiation, or may be an inert solid body.

Substances for which there is sufficient evidence to establish a causal relationship in cancer in humans are referred to as confirmed human carcinogens. Included in this category are the following substances: Aflatoxins, Alcoholic beverages, Aluminium production, 4-aminobiphenyl, Arsenic and arsenic compounds, Asbestos, Manufacture of auramine, Azathioprine, Benzene, Benzidine, Beryllium and beryllium compounds, Betel quid with tobacco, Bis(chloromethyl)ether and chloromethyl methyl ether (technical grade), Boot and shoe manufacture and repair (occupational exposure), 1,4 Butanediol dimethanesulphonate (Myleran), Cadmium and cadmium compounds, Chlorambucil, Chlornaphazine, 1-(2-Chloroethyl)-3-(4-methylcyclohexyl)-1 nitrosourea, Chloromethyl methyl ether (technical), Chromium compounds (hexavalent), Coal gasification, Coal tar pitches, Coal tars, Coke production, Cyclophosphamide, Cyclosporin, Erionite, Ethylene oxide, Furniture and cabinet making, Underground haematite mining with exposure to radon, Iron and steel founding, Isopropyl alcohol manufacture (strong acid process), Manufacture of magenta, Melphalan, 8-Methoxypsoralen (Methoxsalen) plus ultraviolet radiation, Mineral oils-untreated and mildly-treated oils, MOPP and other combined chemotherapy for cancer, Mustard gas (sulphur mustard), 2-Naphthylamine, Nickel and nickel compounds (essentially sulphate and sulphide), Nonsteroidal estrogens (not necessarily all in group) includes diethylstilbestrol, Estrogen replacement therapy, and Combined oral contraceptives and sequential oral contraceptives, Steroidal estrogens (not all in group), Painter (occupational exposure as a painter), Phenacetin (analgesic mixtures containing), Rubber industry, Salted fish (Chinese style), Solar radiation, Shale oils, Soots, Sulphuric acid (occupational exposures to strong-inorganic-acid mists of sulphuric acid), Talc containing asbestiform fibres, Thiotepa, Tobacco products (smokeless), Tobacco smoke, Treosulphan, and Vinyl chloride.

Substances for which there is a lesser degree of evidence in humans but sufficient evidence in animal studies, or degrees of evidence considered unequivocal of mutagenicity in mammalian cells, are referred to as probable human carcinogens. This category of substances includes: Acrylamide, Acrylonitrile, Adriamycin, Anabolic steroids, Azacitidine, Benzanthracene, Benzidine-based dyes (technical grade), Direct Black 38, Direct Blue 6, Direct Brown 95, Benzopyrenel,3-Butadiene, Captafol, Bischloroethyl nitrosourea (BCNU), 1-(2-Chloroethyl)-3-cyclohexyl-1-nitrosourea (CCNU), Chloramphenicolpara-Chloro-ortho-toluidine and its strong acid salts, Chlorozotocin, Cisplatin, Creosotes, Dibenzanthracene, Diesel engine exhaust, Diethyl sulphate, Dimethylcarbamoyl chloride, Dimethyl sulphate, Epichlorohydrin, Ethylene dibromide, N-ethyl-N-nitrosourea, Formaldehyde, Glass manufacturing industry (occupational exposures), Art glass (glass containers and pressed ware), Hairdresser or barber (occupational exposure, probably dyes), Insecticide use (occupational), IQ (2-Amino-3-methylimidazo[4,5-f]quinoline), Mate drinking (hot), 5-Methoxypsoralen, 4,4'-Methylenebis(2-chloroaniline) (MOCA), N-Methyl-N-nitro-N-nitrosoguanidine (MNNG), N-Methyl-N-nitrosourea, Nitrogen mustard, N-Nitrosodiethylamine, N-Nitrosodimethylamine, Petroleum refining (occupational refining exposures), Phenacetin, Polychlorinated biphenyls, Procarbazine hydrochloride, Silica (crystalline), Styrene-7,8-oxide, Tris(1-azaridinyl)phosphine sulphide (Thiotepa), Tris(2,3-dibromopropyl) phosphate, Ultraviolet radiation: A, B and C including sunlamps and sunbeds, and Vinyl bromide.

Substances for which there is sufficient evidence in animal tests are referred to as possible human carcinogens. This category of substances includes: A-C(2-Amino-9H-pyrido[2,3-b]indole), Acetaldehyde, Acetamide, AF-2[2-(2-Furyl)-3-(5-nitro-2-furyl)acrylamide, para-Aminoazobenzene, ortho-Aminoazobenzene, 2-Amino-5-(5-nitro-2-furyl)-1,3,4-thiadiazole, Amitrole, ortho-Anisidine, Antimony trioxide, Aramite, Atrazine, Attapulgite, Azaserine, Benzo[b]fluoranthene, Benzo[j]fluoranthene, Benzo[k]fluoranthene, Benzyl violet, Bitumens (extracts of steam-refined and air-refined bitumens), Bleomycins, Bracken ferns, Bromodichloromethane, Butylated hydroxyanisole (BHA), á-Butyrolactone, Caffeic acid, Carbon black extract, Carbon tetrachloride, Carrageenan (degraded), Ceramic fibres, Chloramphenicol, Chlordane, Chlordecone, Chlorendic acid, Chlorinated paraffins of average carbon-chain length C12 and average degree of chlorination approx 60%, alpha-Chlorinated toluenes (not necessarily all in group), Benzotrichloride, para-Chloroaniline, Chloroform, Chlorophenols, Pentachlorophenol, 2,4,6-Trichlorophenol, Chlorophenoxy herbicides (not necessarily all in group), 4-Chloro-ortho-phenylenediamine, CI Acid Red 114, CI Basic Red 9, CI Direct Blue 15, Citrus Red No. 2, Cobalt and cobalt compounds, Coffee (bladder), para-Cresidine, Cycasin, Dacarbazine, Dantron (1,8-dihydroxyanthraquinone), Daunomycin, DDT, N,N'-Diacetylbenzidine, 4,4'-Diaminodiphenyl ether, 2,4-Diaminotoluene, Dibenz[a,h]acridine, Dibenz[a,j]acridine, 7H-Dibenzo[c,g]carbazole, Dibenzo[a,e]pyrene, Dibenzo[a,h]pyrene, Dibenzo[a,i]pyrene, Dibenzo[a,l]pyrene, 1,2-Dibromo-3-chloropropane, para-Dichlorobenzene, 3,3'-Dichlorobenzene, 3,3'-Dichloro-4,4'-diaminodiphenyl ether, 1,2-Dichloroethane, Dichloromethane, 1,3-Dichloropropene (technical grade), Dichlorvos, Diepoxybutane, Diesel fuel (marine), Di(2-ethylhexyl)phthalate, 1,2-Diethylhydrazine, Diglycidyl resorcinol ether, Dihydrosafrole, Diisopropyl sulfate, 3,3'-Dimethoxybenzidine, para-Dimethylaminoazobenzene, trans-2-[(Dimethylamino)methylimino]-5-[2-(5-nitro-2-furyl[vinyl]-1,3,4-oxidiazole, 2,6-Dimethylaniline (2,6-Xylidene), 3,3'-Dimethylbenzidine (ortho-tolidine), Dimethylformamide, 1,1-Dimethylhydrazine, 1,2-Dimethylhydrazine, 1,6-Dinitropyrene, 1,8-Dinitropyrene, 1,4-Dioxane, Disperse Blue, 1Ethyl acrylate, Ethylene thiourea, Ethyl methanesulphonate, 2-(2-Formylhydrazino)-4-(5-nitro-2-furyl)thiazole, Fuel oils (residual, heavy), Fusarium moniliforme (toxins derived from), Fumonisin B1; Fumonisin B2; Fusarin C, Gasoline, Gasoline engine exhausts, Glasswool, Glu-P-1 (2-Amino-6-methyldipyrido[1,2-a:3'2'-d]imidazole), Glu-P-2(-Aminodipyrido[1,2-a:3'2'-d]imidazole),Glycidaldehyde, Griseofulvin, HC Blue No 1, Heptachlor, Hexachlorobenzene, Hexachlorocyclohexanes Technical grades alpha isomer gamma isomer (lindane), Hexamethylphosphoramide, Hydrazine, Indeno[1,2,3-cd]pyrene, Iron-dextran complex, Isoprene, Lasiocarpine, Lead and lead compounds (inorganic), Magenta (containing CI Basic Red 9), Man-made mineral fibres (see glasswool, rockwool, slagwool, and ceramic fibres), MeA-a-C (2-Amino-3-methyl-9H-pyrido[2,3-b]indole), MeIQ (2-Amino-3,4-dimethylimidazo[4,5-f]-quinolone), MeIQx (2-Amino-3,8-dimethylamidazo[4,5-f]quinoxaline), Methylmercury compounds (methylmercuric chloride), Melphalan, 2-Methylaziridine, Methylazoxymethanol and its acetate, 5-Methylchrysene, 4,4'-Methylenebis(2-methylaniline), 4,4'-Methylenedianiline, Methylmethanesulphonate, 2-methyl-1-nitroanthraquinone (uncertain purity), N-methyl-N-nitrosourethane, Methylthiouracil, Metronidazole, Mirex, Mitomycin, Monocrotaline 5-(Morpholinomethyl)-3-[(5-nitrofurfurylidene)amino]-2-oxazolidinone, Nafenopin, Niridazole, 5-Nitroacenaphthene, 6-Nitrochrysene, Nitrofen (technical grade), 2-Nitrofluorenel-[(5-Nitrofurfurylidene)amino]-2-imidazolidinone, N-[4-(5-Nitro-2-furyl)-2-thiazolyl]acetamide, Nitrogen mustard, N-oxide, Nitrolotriacetic acid and its salts, 2-Nitropropanel-Nitropyrene, 4-Nitropyrene, N-Nitrosodi-n-butylamine, N-Nitrosodiethanolamine, N-Nitrosodi-n-propylamine, 3-(N-Nitrosomethylamino)propionitrile, 4-(N-Nitrosomethylamino)-1-(3-pyridyl)-1-butanone (NNK), N-Nitrosomethylethylamine, N-Nitrosomethylvinylamine, N-Nitrosomorpholine, N-Nitrosonomicotine, N-Nitrosopiperidene, N-Nitrosopyrrolidine, N-Nitrososarcosine, Ochratoxin A, Oil Orange, Panfuran S (containing dihydroxymethylfuratzine), Phenazopyridine hydrochloride, Phenobarbital, Phenoxybenzamine hydrochloride, Phenyl glycidyl ether, PhenytoinPhIP (2-Amino-1-methyl-6-phenylimidazo[4,5-b]pyridine, Pickled vegetables, traditional Asian, Polybrominated biphenyls, Ponceau MXPonceau 3R, Potassium bromate, 1,3-Propane sultone, Propylene oxide, Progestins, Medroxyprogesterone acetate, á-Propiolactone, Propylthiouracil, Rockwool, Saccharin, Safrole, Slagwool, Sodium ortho-phenylphenate, Sterigmatocystin, Streptozotocin, Styrene, Sulfallate, 2,3,7,8-Tetrachlorodibenzo-para-dioxin (TCDD), Tetrachloroethylene, Textile manufacturing (occupational exposures), Thiocetamide, 4,4'-Thiodianiline, Thiourea, Toluene, diisocyanatesortho-Toluidine, Toxaphene (polychlorinated camphenes), Trichlormethine (trimustine hydrochloride), Trp-P-1 (3-Amino-1,4-dimethyl-5-H-pyrido[4,3-b]indole), Trp-P-2 (3-Amino-1-methyl-5H-pyrido[4,3-b]indole), Trypan blue, Uracil mustard, Urethane, 4-Vinylcyclohexene, 4-Vinylcyclohexene diepoxide, Welding fumes, Wood industries and Carpentry and joinery.

Subjects at risk of developing cancer also include those who have a genetic predisposition to cancer. In many cases, genetic predisposition to cancer can be identified by studying the occurrence of cancer in family members. Examples of genetic predisposition to common forms of cancer include, but are not limited to, mutation of BRCA1 and BRCA2 in familial breast cancer, mutation of APC in familial colony cancer (familial polyposis coli), mutation of MSH2 and MLH1 in hereditary nonpolyposis colon cancer (HNPCC), mutation of p53 in Li-Fraumeni syndrome, mutation of Rb1 in retinoblastoma, mutation of RET in multiple endocrine neoplasia type 2 (MEN2), mutation of VHL in renal cancer and mutation of WT1 in Wilms' tumor. Other cancers for which a familial predisposition has been identified include ovarian, prostate, melanoma and lung cancer.

It has been estimated that almost half of all currently diagnosed cancers will be treated with some form of cancer medicament. However, many forms of cancer, including melanoma, colorectal, prostate, endometrial, cervical and bladder cancer, do not respond well to treatment with cancer medicaments. In fact, only about 5-10 percent of cancers can be cured using cancer medicaments alone. These include some forms of leukemias and lymphomas, testicular cancer, choriocarcinoma, Wilms' tumor, Ewing's sarcoma, neuroblastoma, small-cell lung cancer and ovarian cancer. Treatment of still other cancers, including breast cancer, requires a combination therapy of surgery or radiotherapy in conjunction with a cancer medicament.

The immunostimulatory nucleic acids are administered in combination with antibodies which specifically bind to cancer cell surface antigens. These antibodies include but are not limited to anti-CD20 antibodies, anti-CD40 antibodies, anti-CD19 antibodies, anti-CD22 antibodies, anti-HLA-DR antibodies, anti-CD80 antibodies, anti-CD86 antibodies, anti-CD54 antibodies, and anti-CD69 antibodies. These antibodies are available from commercial sources or may be synthesized de novo.

Commercially available anti-CD20 antibodies include but are not limited to those presented in Table 1 below.

| Commercially Available Anti-CD20 Antibodies. | |
|---|---|
| Product/Supplier | Catalog # |
| Monoclonal Antibody to CD20, Human, Purified, 100 µg Alexis Corp. | ANC-169-020 |
| CD20, B-Cell Bab Mouse: anti-Human Clone: L26 Isotype: IgG2a, Kappa; Concentrated Biomeda Corporation | V6021 |
| CD20, B-Cell Mab Mouse: anti-Human Clone: L26 Isotype: IgG2a, Kappa; Concentrated Biomeda Corporation | V1018 |
| CD20, B-Cell MAb Mouse: anti-Human Clone: L26 Isotype: IgG2a, Kappa; Dehydrated Biomeda Corporation | K026 |
| CD20, B-Cell Mab Mouse: anti-Human Clone: L26 Isotype: IgG2a, Kappa; Prediluted Biomeda Corporation | 058D |
| Mouse anti-Human CD20 BioSource International | AHS2022 |
| Mouse anti-Human CD20 BioSource International | AHS2001 |
| Mouse anti-Human CD20 BioSource International | AHS2028 |
| Mouse anti-Human CD20 BioSource International | AHS2002 |

-continued

| Commercially Available Anti-CD20 Antibodies. | |
|---|---|
| Product/Supplier | Catalog # |
| Mouse anti-Human CD20 BioSource International | AHS2021 |
| Mouse Anti-CD20, B-Cell, Human IgG2a Antibody, Kappa, Supernatant, Clone L26, 1 mL BIOTREND Chemikalien GmbH | MOB004 |
| AnTesti-CD20, Human, Mouse, 100 µg Calbiochem | 217670 |
| Mouse Monoclonal Anti-(Human CD20) IgG3 Antibody, Clone H147, 0.5 mL Caltag Laboratories | MHCD2000 |
| Mouse Monoclonal Anti-(Human CD20) IgG3 Antibody, Clone B-ly 1, 1 mL Caltag Laboratories | MHCD2000-4 |
| Mouse Monoclonal Anti-(Human CD20), Mature B-cell) IgG1 Antibody, Clone MEM-97, 1 mL Caltag Laboratories | MON1111 |
| CD20, B-cell, Mouse Anti-Human, Clone: L26, Isotype: IgG2a, kappa, Ready-to-Use, LSAB2, EnVision & EnVision Doublestain, Monoclonal Antibody, 12 mL DAKO Corp. | N150230 |
| CD20, B-cell, Mouse Anti-Human, Clone: L26, Isotype: IgG2a, kappa, Ready-to-Use, LSAB2, EnVision & EnVision Doublestain, Monoclonal Antibody, Packaged for DAKO Autostainer, 33 mL\ DAKO Corp. | N150289 |
| CD20, L26 B-cell Marker, Mouse Anti-Human, Human, Monoclonal Antibody, 1 mL DAKO Corp. | M075501 |
| CD20, L26 B-cell Marker, Mouse Anti-Human Monoclonal Antibody, 1 mL DAKO Corp. | M077401 |
| MxH B cell, CD20 RTU, 12 mL DAKO Corp. | L185030 |
| Monoclonal Anti-B-Cell, CD20 IgG2a Antibody, Clone L26, concentrated, 1 mL Diagnostic BioSystems | Mob 004 |
| Monoclonal Anti-CD20, B-Cell IgG1 Antibody, Clone 7D1, concentrated, 1 mL Diagnostic BioSystems | Mob 241 |
| Monoclonal Anti-CD20, B-Cell IgG2a Antibody, Clone L26, Concentrated, 1 mL Diagnostic BioSystems | Mob 004-01 |
| Rabbit Polyclonal Anti-CD20, B-cell Antibody, Concentrated, 1 mL Diagnostic Biosystems | RP 041 |
| Coulter* Antibodies to Human CDs::CD20 Fisher Scientific Co. | COIM 1455 |
| Coulter* Antibodies to Human CDs::CD20 Fisher Scientific Co. | C06603858 |
| Coulter* Antibodies to Human CDs::CD20 Fisher Scientific Co. | COIM 1342 |
| Coulter* Antibodies to Human CDs::CD20 Fisher Scientific Co. | COIM 1565 |
| Coulter* Antibodies to Human CDs::CD20 Fisher Scientific Co. | COIM 1454 |
| Coulter* Antibodies to Human CDs::CD20 Fisher Scientific Co. | CO6604106 |
| Coulter* Antibodies to Human CDs::CD20 Fisher Scientific Co. | CO6603446 |
| Coulter* Antibodies to Human CDs::CD20 Fisher Scientific Co. | COIM 1456 |
| Coulter* Antibodies to Human CDs::CD20 Fisher Scientific Co. | COIM 1451 |
| Coulter* Antibodies to Human CDs::CD20 Fisher Scientific Co. | CO6602381 |
| Coulter* Antibodies to Human CDs::CD20 Fisher Scientific Co. | COIM1925 |
| Coulter* Antibodies to Human CDs::CD20 Fisher Scientific Co. | CO6602140 |
| CD20, Pan B-cell marker, Mouse Anti-Human, Monoclonal Antibody, 1 mL DAKO Corp. | M077401 |

-continued

Commercially Available Anti-CD20 Antibodies.

| Product/Supplier | Catalog # |
|---|---|
| MxH B Cell, CD20 RTU, 12 mL<br>DAKO Corp. | L185030 |
| Monoclonal Anti-B-Cell, CD20 IgG2a Antibody, Clone L26, Concentrated, 1 mL<br>Diagnostic BioSystems | Mob 004 |
| Monoclonal Anti-CD20, B-Cell IgG1 Antibody, Clone 7D1, Concentrated, 1 mL<br>Diagnostic BioSystems | Mob 241 |
| Monoclonal Anti-CD20, B-Cell IgG2a Antibody, Clone L26, Concentrated, 1 mL<br>Diagnostic BioSystems | Mob 004-01 |
| Rabbit Polyclonal Anti-CD20, B-cell Antibody, Concentrated, 1 mL<br>Diagnostic BioSystems | RP 041 |
| Coulter* Antibodies to Human CDs::CD20<br>Fisher Scientific Co. | COIM 1455 |
| Coulter* Antibodies to Human CDs::CD20<br>Fisher Scientific Co. | CO6603858 |
| Coulter* Antibodies to Human CDs::CD20<br>Fisher Scientific Co. | COIM 1342 |
| Coulter* Antibodies to Human CDs::CD20<br>Fisher Scientific Co. | COIM 1565 |
| Coulter* Antibodies to Human CDs::CD20<br>Fisher Scientific Co. | COIM 1454 |
| Coulter* Antibodies to Human CDs::CD20<br>Fisher Scientific Co. | CO6604106 |
| Coulter* Antibodies to Human CDs::CD20<br>Fisher Scientific Co. | CO6603446 |
| Coulter* Antibodies to Human CDs::CD20<br>Fisher Scientific Co. | COIM 1456 |
| Coulter* Antibodies to Human CDs::CD20<br>Fisher Scientific Co. | COIM 1451 |
| Coulter* Antibodies to Human CDs::CD20<br>Fisher Scientific Co. | CO6602381 |
| Coulter* Antibodies to Human CDs::CD20<br>Fisher Scientific Co. | COIM 1925 |
| Coulter* Antibodies to Human CDs::CD20<br>Fisher Scientific Co. | CO6602140 |
| Coulter* Antibodies to Human CDs::CD20<br>Fisher Scientific Co. | CO6602471 |
| CD20 (B Cell)<br>InnoGenex | AM-1165-11 |
| Coulter* Antibodies to Human CDs::CD20<br>Fisher Scientific Co. | CO6602471 |
| CD20 (B Cell)<br>InnoGenex | AM-1165-11 |
| CD20 (B Cell), Unpurified (0.1 mg/0.1 mL), Clone: B1, Isotype:<br>InnoGenex | AM-1165-11 |
| Mouse Monoclonal Anti-CD20 Ab-1 (B-Cell Marker) $IgG_{2a}/\kappa$ Antibody, Clone: L26, Workshop, 0.1 mL<br>Lab Vision Corp. | MS-340-SO |
| Mouse Monoclonal Anti-CD20 Ab-1 (B-Cell Marker) $IgG_{2a}/\kappa$ Antibody, Clone: L26, Workshop, 0.5 mL<br>Lab Vision Corp. | MS-340-S1 |
| Mouse Monoclonal Anti-CD20 Ab-1 (B-Cell Marker) $IgG_{2a}/\kappa$ Antibody, Clone: L26, Workshop, 1.0 mL<br>Lab Vision Corp. | MS-340-S |
| Mouse Monoclonal Anti-CD20 Ab-1 (B-Cell Marker) $IgG_{2a}/\kappa$ Antibody, Clone: L26, Workshop, 7.0 mL<br>Lab Vision Corp. | MS-340-R7 |
| Mouse Monoclonal Anti-CD20 Ab-1 (B-Cell Marker) $IgG_{2a}/\kappa$ Antibody, Clone: B9E9, Workshop V; 100 µg<br>Lab Vision Corp. | MS-431-P1 |
| Mouse Monoclonal Anti-CD20 Ab-1 (B-Cell Marker) $IgG_{2a}/\kappa$ Antibody, Clone: B9E9, Workshop V; 200 µg<br>Lab Vision Corp. | MS-431-P |
| Mouse Monoclonal Anti-CD20 (Ab-1 (B-Cell Marker) $IgG_{2a}/\kappa$ Antibody, Clone: B9E9, Workshop V; 20 µg<br>Lab Vision Corp. | MS-431-PO |
| Mouse Monoclonal Anti-CD20 Ab-1 (B-Cell Marker) $IgG_1/\kappa$ Antibody, Clone: 93-1B3, Workshop V; Code: CD20.4, 200 µg<br>Lab Vision Corp. | MS-758-P1 |
| Mouse Monoclonal Anti-CD20 Ab-3 (B-Cell Marker) $IgG_1/\kappa$ Antibody, Clone: 93-1B3, Workshop V; Code: CD20.4, 200 µg<br>Lab Vision Corp. | MS-758-P |
| Mouse Monoclonal Anti-CD20 Ab-3 (B-Cell Marker) $IgG_1/$ Antibody, Clone: 93-1B3, Workshop V; Code: CD20.4<br>Lab Vision Corp. | MS-758-PO |
| Human CD20, B Cell, 6 mL<br>Maxim Biotech Inc. | MAB-0020 |
| Mouse Monoclonal Anti-B Cell, CD20 $IgG_{2a}$, κ Antibody, Concentrate, 1 mL<br>Scytek | A9004C |
| Mouse Monoclonal Anti-B Cell, CD20 $IgG_{2a}$, κ Antibody, Ready-to-Use, 1 mL<br>Scytek | A20003 |
| Mouse Monoclonal Anti-CD20, B Cell $IgG_{2a}$, κ Antibody, Concentrate, 1 mL<br>Scytek | A9001C (Clone: L26) |
| Mouse Monoclonal Anti-CD20, B Cell $IgG_{2a}$, κ Antibody, Ready-to-Use, 6 mL<br>Scytek | A00003 |
| Mouse Monoclonal Anti-(Human CD20 IgG1 Antibody, Clone 7D1, 1 mL<br>Serotec, Inc. | MCA 1807 |
| Mouse Monoclonal Anti-(Human CD20 IgG1 Antibody, Clone AT80, 0.2 mg<br>Serotec, Inc. | MCA 1822 |
| Mouse Monoclonal Anti-(Human CD20 IgG2b Antibody, Clone 2H7, 0.2 mg<br>Serotec, Inc. | MCA 1710 |
| Antibody Panels, Hematopoietic Markers, Lymphocyre Related Antigens, CD20, B Cell, Clone L26, Concentrated, 1 mL, Ab Source Mouse, Ab# 324<br>Signet Pathology Systems, Inc. | 324-01 |
| Antibody Panels, Hematopoietic Markers, Lymphocyte Related Antigens, CD20, B Cell, Clone L26, Level 1, 3 mL, Ab 324<br>Signet Pathology Systems, Inc. | 324-13 |
| Antibody Panels, Hematopoietic Markers, Lymphocyte Related Antigens, CD20, B Cell, Clone L26, level 1, 6 mL, Ab Source Mouse, Ab# 324<br>Signet Pathology Systems, Inc. | 324-16 |
| Antibody Panels, Hematopoietic Markers, Lymphocyte Related Antigens, CD20, B Cell, Clone L26, Level 2, 6 mL, Ab Source Mouse, Ab# 324<br>Signet Pathology Systems, Inc. | 324-26 |
| Monoclonal Mouse anti-CD20, B9E9, Epitope-Affinity Purified-Unconjugated, $IgG_{2a}$-κ, 200 µg<br>Zymed Laboratories, Inc. | 07-2003 |

Antibodies are well known to those of ordinary skill in the science of immunology. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody. Wahl R L et al., *J Nucl Med* 24:316-25 (1983). Antibody fragments which are particularly useful according to the methods of the invention are those which are bispecific and constructed to enhance FcR binding, e.g., include an Fc portion. These include, but are not limited to Medarex antibodies (MDX-210, 220, 22, 447, and 260). Other non-Fc containing fragments which interact with the antigens induced on the cell surface are also useful. These are particularly useful in combination with immunotoxins and/or radioactivity. The fragments can be delivered separately from the immunotoxins or radioactivity or conjugated thereto (e.g., radiolabed antibodies or antibody fragments).

Within the antigen-binding portion of an antibody, as is well-known in the art, there are complementarity-determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity-determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies. A "humanized monoclonal antibody" as used herein is a human monoclonal antibody or functionally active fragment thereof having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double-stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Human monoclonal antibodies may be made by any of the methods known in the art, such as those disclosed in U.S. Pat. No. 5,567,610, issued to Borrebaeck et al., U.S. Pat. No. 5,565,354, issued to Ostberg, U.S. Pat. No. 5,571,893, issued to Baker et al, Kozbor D et al., *J Immunol* 133:3001-5 (1984), Brodeur et al., Monoclonal Antibody Production Techniques and Applications, pp. 51-63 (Marcel Dekker, Inc, New York, 1987), and Boerner P et al., *J Immunol* 147:86-95 (1991). In addition to the conventional methods for preparing human monoclonal antibodies, such antibodies may also be prepared by immunizing transgenic animals that are capable of producing human antibodies (e.g., Jakobovits A et al., *Proc Natl Acad Sci USA* 90:2551-5 (1993); Jakobovits A et al., *Nature* 362:255-8 (1993); Bruggermann et al., Year in Immunology 7:33 (1993); and U.S. Pat. No. 5,569,825 issued to Lonberg).

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Other antibodies useful according to the invention are antibodies of the IgG1 isotype. As mentioned above, anti-IgG1 isotype antibody as used herein refers to a human or humanized anti-IgG1 unless otherwise specified. IgG1 isotype antibodies are well known in the art and include at least the antibodies listed in Table 2 below.

TABLE 2

Cancer Immunotherapies In Development Or On The Market.

| Marketer | Brand Name (Generic Name) | Indication |
|---|---|---|
| IDEC/Genentech, Inc./Hoffmann-LaRoche (first monoclonal antibody licensed for the treatment of cancer in the U.S.) | Rituxan ™ (rituximab, Mabthera) (IDEC-C2B8, chimene murine/human anti-CD20 MAb) | non-Hodgkin's lymphoma |
| Genentech/Hoffmann-La Roche | Herceptin, anti-Her2 hMAb | Breast/ovarian |
| Cytogen Corp. | Quadramet (CYT-424) radiotherapeutic agent | Bone metastases |
| Centocor/Glaxo/Ajinomoto | Panorex ® (17-1A) (murine monoclonal antibody) | Adjuvant therapy for colorectal (Dukes-C) |
| Centocor/Ajinomoto | Panorex ® (17-1A) (chimeric murine monoclonal antibody) | Pancreatic, lung, breast, ovary |
| IDEC | IDEC-Y2B8 (murine, anti-CD20 MAb labeled with Yttrium-90) | non-Hodgkin's lymphoma |
| ImClone Systems | BEC2 (anti-idiotypic MAb, mimics the $GD_3$ epitope) (with BCG) | Small cell lung |
| ImClone Systems | C225 (chimeric monoclonal antibody to epidermal growth factor receptor (EGFr)) | Renal cell |
| Techniclone International/Alpha Therapeutics | Oncolym (Lym-1 monoclonal antibody linked to 131 iodine) | non-Hodgkin's lymphoma |
| Protein Design Labs | SMART M195 Ab, humanized | Acute myeloid leukemia |
| Techniclone Corporation/Cambridge Antibody Technology | $^{131}$I LYM-1 (Oncolym ™) | non-Hodgkin's lymphoma |
| Aronex Pharmaceuticals, Inc. | ATRAGEN ® | Acute promyelocytic leukemia |
| ImClone Systems | C225 (chimeric anti-EGFr monoclonal antibody) + cisplatin or radiation | Head & neck, non-small cell lung cancer |
| Altarex, Canada | Ovarex (B43.13, anti-idiotypic CA125, mouse MAb) | Ovarian |
| Coulter Pharma (Clinical results have been positive, but the drug has been associated with significant bone marrow toxicity) | Bexxar (anti-CD20 Mab labeled with $^{131}$I) | non-Hodgkin's lymphoma |
| Aronex Pharmaceuticals, Inc. | ATRAGEN ® | Kaposi's sarcoma |
| IDEC Pharmaceuticals Corp./Genentech | Rituxan ™ (MAb against CD20) pan-B Ab in combo, with chemotherapy | B cell lymphoma |
| LeukoSite/Ilex Oncology | LDP-03, huMAb to the leukocyte antigen CAMPATH | Chronic lymphocytic leukemia (CLL) |
| Center of Molecular Immunology | ior t6 (anti CD6, murine MAb) CTCL | Cancer |
| Medarex/Novartis | MDX-210 (humanized anti-HER-2 bispecific antibody) | Breast, ovarian |
| Medarex/Novartis | MDX-210 (humanized anti-HER-2 bispecific antibody) | Prostate, non-small cell lung, pancreatic, breast |
| Medarex | MDX-11 (complement activating receptor (CAR) monoclonal antibody) | Acute myelogenous leukemia (AML) |
| Medarex/Novartis | MDX-210 (humanized anti-HER-2 bispecific antibody) | Renal and colon |
| Medarex | MDX-11 (complement activating receptor (CAR) monoclonal antibody) | Ex vivo bone marrow purging in acute myelogenous leukemia (AML) |
| Medarex | MDX-22 (humanized bispecific antibody, MAb-conjugates) (complement cascade activators) | Acute myeloid leukemia |
| Cytogen | OV103 (Yttrium-90 labelled antibody) | Ovarian |
| Cytogen | OV103 (Yttrium-90 labelled antibody) | Prostate |
| Aronex Pharmaceuticals, Inc. | ATRAGEN ® | non-Hodgkin's lymphoma |
| Glaxo Wellcome plc | 3622W94 MAb that binds to EGP40 (17-1A) pancarcinoma antigen on adenocarcinomas | non-small cell lung, prostate (adjuvant) |
| Genentech | Anti-VEGF, RhuMAb (inhibits angiogenesis) | Lung, breast, prostate, colorectal |
| Protein Design Labs | Zenapax (SMART Anti-Tac (IL-2 receptor) Ab, humanized) | Leukemia, lymphoma |
| Protein Design Labs | SMART M195 Ab, humanized | Acute promyelocytic leukemia |
| ImClone Systems | C225 (chimeric anti-EGFr monoclonal antibody) + taxol | Breast |
| ImClone Systems (licensed from RPR) | C225 (chimeric anti-EGFr monoclonal antibody) + doxorubicin | prostate |

TABLE 2-continued

Cancer Immunotherapies In Development Or On The Market.

| Marketer | Brand Name (Generic Name) | Indication |
| --- | --- | --- |
| ImClone Systems | C225 (chimeric anti-EGFr monoclonal antibody) + adriamycin | prostate |
| ImClone Systems | BEC2 (anti-idiotypic MAb, mimics the $GD_3$ epitope) | Melanoma |
| Medarex | MDX-210 (humanized anti-HER-2 bispecific antibody) | Cancer |
| Medarex | MDX-220 (bispecific for tumors that express TAG-72) | Lung, colon, prostate, ovarian, endometrial, pancreatic and gastric |
| Medarex/Novartis | MDX-210 (humanized anti-HER-2 bispecific antibody) | Prostate |
| Medarex/Merck KgaA | MDX-447 (humanized anti-EGF receptor bispecific antibody) | EGF receptor cancers (head & neck, prostate, lung, bladder, cervical, ovarian) |
| Medarex/Novartis | MDX-210 (humanized anti-HER-2 bispecific antibody) | Comb. Therapy with G-CSF for various cancers, esp. breast |
| IDEC | MELIMMUNE-2 (murine monoclonal antibody therapeutic vaccine) | Melanoma |
| IDEC | MELIMMUNE-1 (murine monoclonal antibody therapeutic vaccine) | Melanoma |
| Immunomedics, Inc. | CEACIDE ® (I-131) | Colorectal and other |
| NeoRx | Pretarget ® radioactive antibodies | non-Hodgkin's B cell lymphoma |
| Novopharm Biotech, Inc. | NovoMAb-G2 (pancarcinoma specific Ab) | Cancer |
| Techniclone Corporation/Cambridge Antibody Technology | TNT (chimeric MAb to histone antigens) | Brain |
| Techniclone International/Cambridge Antibody Technology | TNT (chimeric MAb to histone antigens) | Brain |
| Novopharm | Gliomab-H (Monoclonals - Humanized Abs) | Brain, melanomas, neuroblastomas |
| Genetics Institute/AHP | GNI-250 Mab | Colorectal |
| Merck KgaA | EMD-72000 (chimeric-EGF antagonist) | Cancer |
| Immunomedics | LymphoCide (humanized LL2 antibody) | non-Hodgkin's B-cell lymphoma |
| Immunex/AHP | CMA 676 (monoclonal antibody conjugate) | Acute myelogenous leukemia |
| Novopharm Biotech, Inc. | Monopharm-C | Colon, lung, pancreatic |
| Novopharm Biotech, Inc. | 4B5 anti-idiotype Ab | Melanoma, small-cell lung |
| Center of Molecular Immunology | ior egf/r3 (anti EGF-R humanzied Ab) | Radioimmunotherapy |
| Center of Molecular Immunology | ior c5 (murine MAb colorectal) for radioimmunotherapy | Colorectal |
| Creative BioMolecules/Chiron | BABS (biosynthetic antibody binding site) Proteins | Breast cancer |
| ImClone Systems/Chugai | FLK-2 (monoclonal antibody to fetal liver kinase-2 (FLK-2)) | Tumor-associated angiogenesis |
| ImmunoGen, Inc. | Humanized MAb/small-drug conjugate | Small-cell lung |
| Medarex, Inc. | MDX-260 bispecific, targets GD-2 | Melanoma, glioma, neuroblastoma |
| Procyon Biopharma, Inc. | ANA Ab | Cancer |
| Protein Design Labs | SMART 1D10 Ab | B-cell lymphoma |
| Protein Design Labs/Novartis | SMART ABL 364 Ab | Breast, lung, colon |
| Immunomedics, Inc. | ImmuRAIT-CEA | Colorectal |

In some embodiments the nucleic acid and antibody are administered in combination with a cancer therapy. As used herein, a "cancer therapy" refers to an agent which prevents growth of a cancer cell by decreasing or slowing the rate of growth, by inhibiting growth altogether, or by killing or inducing apoptosis of the cancer cell. Thus, as used herein, "treating cancer" includes preventing the development of a cancer, reducing the symptoms of cancer, and/or inhibiting the growth of an established cancer. In other aspects, the cancer therapy is administered to a subject at risk of developing a cancer for the purpose of reducing the risk of developing the cancer. Various types of medicaments for the treatment of cancer are described herein. For the purpose of this specification, cancer therapies are classified as chemotherapeutic agents, cancer vaccines, hormone therapy, biological response modifiers, surgical procedures, and radiotherapy aimed at treating cancer. Additionally, the methods of the invention are intended to embrace the use of more than one cancer therapy along with the immunostimulatory nucleic acids and antibody. As an example, where appropriate, the immunostimulatory nucleic acids may be administered with a both a chemotherapeutic agent and a radiotherapy.

Cancer therapies function in a variety of ways. Some cancer therapies work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer therapies can alternately target signal transduction pathways and molecular mechanisms which are altered in cancer cells.

Other cancer therapies target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exit the primary tumor site and seed a distal tissue, thereby forming a secondary tumor), medicaments that impede this metastasis are also useful in the treatment of cancer. Angiogenic mediators include basic FGF, VEGF, angiopoietins, angiostatin, endostatin, TNF-$\alpha$, TNP-470, thrombospondin-1, platelet factor 4, CAI, and certain members of the integrin family of proteins. One category of this type of medicament is a metalloproteinase inhibitor, which inhibits the enzymes used by the cancer cells to exit the primary tumor site and extravasate into another tissue.

As used herein, chemotherapeutic agents encompass both chemical and biological agents. These agents function to inhibit a cellular activity which the cancer cell is dependent upon for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. Chemotherapeutic agents which are currently in development or in use in a clinical setting are shown in Table 3 below.

TABLE 3

Cancer Drugs In Development Or On The Market.

| Marketer | Brand Name | Generic Name | Indication |
|---|---|---|---|
| Abbott | TNP 470/AGM 1470 | Fragyline | Anti-Angiogenesis in Cancer |
| Takeda | TNP 470/AGM 1470 | Fragyline | Anti-Angiogenesis in Cancer |
| Scotia | Meglamine GLA | Meglamine GLA | Bladder Cancer |
| Medeva | Valstar | Valrubicin | Bladder Cancer - Refractory in situ carcinoma |
| Medeva | Valstar | Valrubicin | Bladder Cancer - Papillary Cancer |
| Rhone Poulenc | Gliadel Wafer | Carmustine + Polifepr Osan | Brain Tumor |
| Warner Lambert | Undisclosed Cancer (b) | Undisclosed Cancer (b) | Cancer |
| Bristol-Myers Squibb | RAS Farnesyl Transferase Inhibitor | RAS FarnesylTransferase Inhibitor | Cancer |
| Novartis | MMI 270 | MMI 270 | Cancer |
| Bayer | BAY 12-9566 | BAY 12-9566 | Cancer |
| Merck | Farnesyl Transferase Inhibitor | Farnesyl Transferase Inhibitor | Cancer (Solid tumors - pancreas, colon, lung, breast) |
| Pfizer | PFE | MMP | Cancer, angiogenesis |
| Pfizer | PFE | Tyrosine Kinase | Cancer, angiogenesis |
| Lilly | MTA/LY 231514 | MTA/LY 231514 | Cancer Solid Tumors |
| Lilly | LY 264618/Lometexol | Lometexol | Cancer Solid Tumors |
| Scotia | Glamolec | LiGLA (lithium-gamma linolenate) | Cancer, pancreatic, breast, colon |
| Warner Lambert | CI-994 | CI-994 | Cancer, Solid Tumors/ Leukemia |
| Schering AG | Angiogenesis inhibitor | Angiogenesis Inhibitor | Cancer/Cardio |
| Takeda | TNP-470 | n/k | Malignant Tumor |
| Smithkline Beecham | Hycamtin | Topotecan | Metastatic Ovarian Cancer |
| Novartis | PKC 412 | PKC 412 | Multi-Drug Resistant Cancer |
| Novartis | Valspodar | PSC 833 | Myeloid Leukemia/Ovarian Cancer |
| Immunex | Novantrone | Mitoxantrone | Pain related to hormone refractory prostate cancer. |
| Warner Lambert | Metaret | Suramin | Prostate |
| Genentech | Anti-VEGF | Anti-VEGF | Prostate/Breast/Colorectal/ NSCL Cancer |
| British Biotech | Batimastat | Batimastat (BB94) | Pterygium |
| Eisai | E 7070 | E 7070 | Solid Tumors |
| Biochem Pharma | BCH-4556 | BCH-4556 | Solid Tumors |
| Sankyo | CS-682 | CS-682 | Solid Tumors |
| Agouron | AG2037 | AG2037 | Solid Tumors |
| IDEC Pharma | 9-AC | 9-AC | Solid Tumors |
| Agouron | VEGF/b-FGF Inhibitors | VEGF/b-FGF Inhibitors | Solid Tumors |
| Agouron | AG3340 | AG3340 | Solid Tumors/Macular Degeneration |
| Vertex | Incel | VX-710 | Solid Tumors - IV |
| Vertex | VX-853 | VX-853 | Solid Tumors - Oral |
| Zeneca | ZD 0101 (inj) | ZD 0101 | Solid Tumors |
| Novartis | ISI 641 | ISI 641 | Solid Tumors |
| Novartis | ODN 698 | ODN 698 | Solid Tumors |
| Tanube Seiyaku | TA 2516 | Marimistat | Solid Tumors |
| British Biotech | Marimastat | Marimastat (BB 2516) | Solid Tumors |

TABLE 3-continued

Cancer Drugs In Development Or On The Market.

| Marketer | Brand Name | Generic Name | Indication |
|---|---|---|---|
| Celltech | CDP 845 | Aggrecanase Inhibitor | Solid Tumors/Breast Cancer |
| Chiroscience | D2163 | D2163 | Solid Tumors/Metastases |
| Warner Lambert | PD 183805 | PD 183805 | |
| Daiichi | DX8951f | DX8951f | Anti-Cancer |
| Daiichi | Lemonal DP 2202 | Lemonal DP 2202 | Anti-Cancer |
| Fujisawa | FK 317 | FK 317 | Anticancer Antibiotic |
| Chugai | Picibanil | OK-432 | Antimalignant Tumor |
| Nycomed Amersham | AD 32/valrubicin | Valrubicin | Bladder Cancer-Refractory In situ Carcinoma |
| Nycomed Amersham | Metastron | Strontium Derivative | Bone Cancer (adjunct therapy, Pain) |
| Schering Plough | Temodal | Temozolomide | Brain Tumors |
| Schering Plough | Temodal | Temozolonide | Brain Tumors |
| Liposome | Evacet | Doxorubicin, Liposomal | Breast Cancer |
| Nycomed Amersham | Yewtaxan | Paclitaxel | Breast Cancer Advanced, Ovarian Cancer Advanced |
| Bristol-Myers Squibb | Taxol | Paclitaxel | Breast Cancer Advanced, Ovarian Cancer Advanced, NSCLC |
| Roche | Xeloda | Capecitabine | Breast Cancer, Colorectal Cancer |
| Roche | Furtulon | Doxifluridine | Breast Cancer, Colorectal Cancer, Gastric Cancer |
| Pharmacia & Upjohn | Adriamycin | Doxorubicin | Breast Cancer, Leukemia |
| Ivax | Cyclopax | Paclitaxel, Oral | Breast/Ovarian Cancer |
| Rhone Poulenc | Oral Taxoid | Oral Taxoid | Broad Cancer |
| AHP | Novantrone | Mitoxantrone | Cancer |
| Sequus | SPI-077 | Cisplatin, Stealth | Cancer |
| Hoechst | HMR 1275 | Flavopiridol | Cancer |
| Pfizer | CP-358, 774 | EGFR | Cancer |
| Pfizer | CP-609, 754 | RAS Oncogene Inhibitor | Cancer |
| Bristol-Myers Squibb | BMS-182751 | Oral Platinum | Cancer (Lung, Ovarian) |
| Bristol-Myers Squibb | UFT (Tegafur/Uracil) | UFT (Tegafur/Uracil) | Cancer Oral |
| Johnson & Johnson | Ergamisol | Levamisole | Cancer Therapy |
| Glaxo Wellcome | Eniluracil/776C85 | 5FU Enhancer | Cancer, Refractory Solid & Colorectal Cancer |
| Johnson & Johnson | Ergamisol | Levamisole | Colon Cancer |
| Rhone Poulenc | Campto | Irinotecan | Colorectal Cancer, Cervical Cancer |
| Pharmacia & Upjohn | Camptosar | Irinotecan | Colorectal Cancer, Cervical Cancer |
| Zeneca | Tomudex | Ralitrexed | Colorectal Cancer, Lung Cancer, Breast Cancer |
| Johnson & Johnson | Leustain | Cladribine | Hairy Cell Leukaemia |
| Ivax | Paxene | Paclitaxel | Kaposi Sarcoma |
| Sequus | Doxil | Doxorubicin, Liposomal | KS/Cancer |
| Sequus | Caelyx | Doxorubicin, Liposomal | KS/Cancer |
| Schering AG | Fludara | Fludarabine | Leukaemia |
| Pharmacia & Upjohn | Pharmorubicin | Epirubicin | Lung/Breast Cancer |
| Chiron | DepoCyt | DepoCyt | Neoplastic Meningitis |
| Zeneca | ZD1839 | ZD 1839 | Non Small Cell Lung Cancer, Pancreatic Cancer |
| BASF | LU 79553 | Bis-Naphtalimide | Oncology |
| BASF | LU 103793 | Dolastain | Oncology |
| Schering Plough | Caetyx | Doxorubicin-Liposome | Ovarian/Breast Cancer |
| Lilly | Gemzar | Gemcitabine | Pancreatic Cancer, Non Small Cell Lung Cancer, Breast, Bladder and Ovarian |
| Zeneca | ZD 0473/Anormed | ZD 0473/Anormed | Platinum based NSCL, ovarian etc. |
| Yamanouchi | YM 116 | YM 116 | Prostate Cancer |
| Nycomed Amersham | Seeds/I-125 Rapid St | Iodine Seeds | Prostate Cancer |
| Agouron | Cdk4/cdk2 inhibitors | cdk4/cdk2 inhibitors | Solid Tumors |
| Agouron | PARP inhibitors | PARP Inhibitors | Solid Tumors |
| Chiroscience | D4809 | Dexifosamide | Solid Tumors |

TABLE 3-continued

Cancer Drugs In Development Or On The Market.

| Marketer | Brand Name | Generic Name | Indication |
|---|---|---|---|
| Bristol-Myers Squibb | UFT (Tegafur/Uracil) | UFT (Tegafur/Uracil) | Solid Tumors |
| Sankyo | Krestin | Krestin | Solid Tumors |
| Asta Medica | Ifex/Mesnex | Ifosamide | Solid Tumors |
| Bristol-Myers Squibb | Ifex/Mesnex | Ifosamide | Solid Tumors |
| Bristol-Myers Squibb | Vumon | Teniposide | Solid Tumors |
| Bristol-Myers Squibb | Paraplatin | Carboplatin | Solid Tumors |
| Bristol-Myers Squibb | Plantinol | Cisplatin, Stealth | Solid Tumors |
| Bristol-Myers Squibb | Plantinol | Cisplatin | Solid Tumors |
| Bristol-Myers Squibb | Vepeside | Etoposide | Solid Tumors Melanoma |
| Zeneca | ZD 9331 | ZD 9331 | Solid Tumors, Advanced Colorectal |
| Chugai | Taxotere | Docetaxel | Solid Tumors, Breast Cancer |
| Rhone Poulenc | Taxotere | Docetaxel | Solid Tumors, Breast Cancer |
| Glaxo Wellcome | Prodrug of guanine arabinside | prodrug of arabinside | T Cell Leukemia/Lymphoma & B Cell Neoplasm |
| Bristol-Myers Squibb | Taxane Analog | Taxane Analog | Taxol follow up |

Another useful anti-cancer therapy is Interferon-α (e.g., INTRON® A, Schering).

The compounds useful according to the invention are nucleic acids. The nucleic acids may be double-stranded or single-stranded. Generally, double-stranded molecules may be more stable in vivo, while single-stranded molecules may have increased activity. The terms "nucleic acid" and "oligonucleotide" refer to multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)) or a modified base. As used herein, the terms refer to oligoribonucleotides as well as oligodeoxyribonucleotides. The terms shall also include polynucleosides (i.e., a polynucleotide minus the phosphate) and any other organic base-containing polymer. The terms "nucleic acid" and "oligonucleotide" also encompass nucleic acids or oligonucleotides with a covalently modified base and/or sugar. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide-nucleic acids (which have amino acid backbone with nucleic acid bases). In some embodiments the nucleic acids are homogeneous in backbone composition.

Nucleic acids also can include base analogs such as C-5 propyne modified bases. Wagner R W et al., *Nature Biotechnol* 14:840-4 (1996). Purines and pyrimidines include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The nucleic acid is a linked polymer of bases or nucleotides. As used herein with respect to linked units of a nucleic acid, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a nucleic acid, are most common. The individual units of a nucleic acid may be linked, however, by synthetic or modified linkages.

Whenever a nucleic acid is represented by a sequence of letters it will be understood that the nucleotides are in 5'→3' order from left to right and that "A" denotes adenosine, "C" denotes cytosine, "G" denotes guanosine, "T" denotes thymidine, and "U" denotes uracil unless otherwise noted.

Nucleic acid molecules useful according to the invention can be obtained from natural nucleic acid sources (e.g., genomic nuclear or mitochondrial DNA or cDNA), or are synthetic (e.g., produced by oligonucleotide synthesis). Nucleic acids isolated from existing nucleic acid sources are referred to herein as native, natural, or isolated nucleic acids. The nucleic acids useful according to the invention may be isolated from any source, including eukaryotic sources, prokaryotic sources, nuclear DNA, mitochondrial DNA, etc. Thus, the term nucleic acid encompasses both synthetic and isolated nucleic acids. The term "isolated" as used herein refers to a nucleic acid which is substantially free of other nucleic acids, proteins, lipids, carbohydrates or other materials with which it is naturally associated. The nucleic acids can be produced on a large scale in plasmids, (see Sambrook T et al., "Molecular Cloning: A Laboratory Manual", Cold Spring Harbor Laboratory Press, New York, 1989) and separated into smaller pieces or administered whole. After being administered to a subject the plasmid can be degraded into oligonucleotides. One skilled in the art can purify viral, bacterial, eukaryotic, etc., nucleic acids using standard techniques, such as those employing restriction enzymes, exonucleases or endonucleases.

For use in the instant invention, the nucleic acids can be synthesized de novo using any of a number of procedures well known in the art. For example, the b-cyanoethyl phosphoramidite method (Beaucage S L et al., *Tetrahedron Lett* 22:1859, 1981); nucleoside H-phosphonate method (Garegg et al., *Tetrahedron Lett* 27:4051-4, 1986; Froehler et al., *Nucl Acid Res* 14:5399-407, 1986; Garegg et al., *Tetrahedron Lett* 27:4055-8, 1986; Gaffney et al., *Tetrahedron Lett* 29:2619-22, 1988). These chemistries can be performed by a variety of automated oligonucleotide synthesizers available in the market.

In some embodiments, the nucleic acids useful according to the invention are immunostimulatory nucleic acids. An immunostimulatory nucleic acid is any nucleic acid, as described above, which is capable of modulating an immune response. A nucleic acid which modulates an immune response is one which produces any form of immune stimulation, including, but not limited to, induction of cytokines, B-cell activation, T-cell activation, monocyte activation. Immunostimulatory nucleic acids include, but are not limited to, CpG nucleic acids, methylated CpG nucleic acids, T-rich nucleic acids, poly-G nucleic acids, and nucleic acids having phosphate modified backbones, such as phosphorothioate backbones.

A "CpG nucleic acid" or a "CpG immunostimulatory nucleic acid" as used herein is a nucleic acid containing at least one unmethylated CpG dinucleotide (cytosine-guanine dinucleotide sequence, i.e., "CpG DNA" or DNA containing a 5' cytosine followed by 3' guanosine and linked by a phosphate bond) and activates a component of the immune system. The entire CpG nucleic acid can be unmethylated or portions may be unmethylated but at least the C of the 5' CG 3' must be unmethylated.

In one embodiment the invention provides a CpG nucleic acid represented by at least the formula:

$$5' N_1 X_1 C G X_2 N_2 3'$$

wherein $X_1$ and $X_2$ are nucleotides and N is any nucleotide and $N_1$ and $N_2$ are nucleic acid sequences composed of from about 0-25 N's each. In some embodiments $X_1$ is adenine, guanine, or thymine and $X_2$ is cytosine, adenine, or thymine. In other embodiments $X_1$ is cytosine and/or $X_2$ is guanine.

In other embodiments the CpG nucleic acid is represented by at least the formula:

$$5' N_1 X_1 X_2 C G X_3 X_4 N_2 3'$$

wherein $X_1$, $X_2$, $X_3$, and $X_4$ are nucleotides. In some embodiments, $X_1 X_2$ are nucleotides selected from the group consisting of: GpT, GpG, GpA, ApA, ApT, ApG, CpT, CpA, CpG, TpA, TpT, and TpG; and $X_3 X_4$ are nucleotides selected from the group consisting of: TpT, CpT, ApT, TpG, ApG, CpG, TpC, ApC, CpC, TpA, ApA, and CpA; N is any nucleotide and $N_1$ and $N_2$ are nucleic acid sequences composed of from about 0-25 N's each. In some embodiments, $X_1 X_2$ are GpA or GpT and $X_3 X_4$ are TpT. In other embodiments $X_1$ or $X_2$ or both are purines and $X_3$ or $X_4$ or both are pyrimidines or $X_1 X_2$ are GpA and $X_3$ or $X_4$ or both are pyrimidines.

In some embodiments $N_1$ and $N_2$ of the nucleic acid do not contain a CCGG or CGCG quadmer or more than one CCG or CGG trimer. The effect of a CCGG or CGCG quadmer or more than one CCG or CGG trimer depends in part on the status of the nucleic acid backbone. For instance, if the nucleic acid has a phosphodiester backbone or a chimeric backbone the inclusion of these sequences in the nucleic acid will only have minimal if any affect on the biological activity of the nucleic acid. If the backbone is completely phosphorothioate or significantly phosphorothioate then the inclusion of these sequences may have more influence on the biological activity or the kinetics of the biological activity, but compounds containing these sequences are still useful. In another embodiment the CpG nucleic acid has the sequence 5' TCN$_1$TX$_1$X$_2$CGX$_3$X$_4$ 3' (SEQ ID NO:850).

A "T-rich nucleic acid" or "T-rich immunostimulatory nucleic acid" is a nucleic acid which includes at least one poly-T sequence and/or which has a nucleotide composition of greater than 25% T nucleotide residues and which activates a component of the immune system. A nucleic acid having a poly-T sequence includes at least four Ts in a row, such as 5' TTTT 3'. Preferably the T-rich nucleic acid includes more than one poly-T sequence. In preferred embodiments the T-rich nucleic acid may have 2, 3, 4, etc., poly-T sequences, such as oligonucleotide #2006 (5' TCGTCGTTTTGTCGTTTTGTCGTT 3', SEQ ID NO: 729). One of the most highly immunostimulatory T-rich oligonucleotides discovered according to the invention is a nucleic acid composed entirely of T nucleotide residues, e.g., oligonucleotide #2183 (5' TTTTTTTTTTTTTTTTTTTTTTTT 3', SEQ ID NO: 841). Other T-rich nucleic acids have a nucleotide composition of greater than 25% T nucleotide residues, but do not necessarily include a poly-T sequence. In these T-rich nucleic acids the T nucleotide resides may be separated from one another by other types of nucleotide residues, i.e., G, C, and A. In some embodiments the T-rich nucleic acids have a nucleotide composition of greater than 30%, 40%, 50%, 60%, 70%, 80%, 90%, and 99%, T nucleotide residues and every integer % in between. Preferably the T-rich nucleic acids have at least one poly-T sequence and a nucleotide composition of greater than 25% T nucleotide residues.

In one embodiment the T-rich nucleic acid is represented by at least the formula:

$$5' X_1 X_2 T T T T X_3 X_4 3'$$

wherein $X_1$, $X_2$, $X_3$, and $X_4$ are nucleotides. In one embodiment $X_1 X_2$ is TT and/or $X_3 X_4$ is TT. In another embodiment $X_1 X_2$ are any one of the following nucleotides TA, TG, TC, AT, AA, AG, AC, CT, CC, CA, CG, GT, GG, GA, and GC; and $X_3 X_4$ are any one of the following nucleotides TA, TG, TC, AT, AA, AG, AC, CT, CC, CA, CG, GT, GG, GA, and GC.

In some embodiments it is preferred that the T-rich nucleic acid does not contain poly-C (CCCC), poly-A (AAAA), poly-G (GGGG), CpG motifs, or multiple GGs. In other embodiments the T-rich nucleic acid includes these motifs. Thus in some embodiments of the invention the T-rich nucleic acids include CpG dinucleotides and in other embodiments the T-rich nucleic acids are free of CpG dinucleotides. The CpG dinucleotides may be methylated or unmethylated.

Poly-G containing nucleic acids are also immunostimulatory. A variety of references, including Pisetsky D S et al., *Mol Biol Rep* 18:217-21 (1993); Krieger M et al., *Annu Rev Biochem* 63:601-37 (1994); Macaya R F et al., *Proc Natl Acad Sci USA* 90:3745-9 (1993); Wyatt J R et al., *Proc Natl Acad Sci USA* 91:1356-60 (1994); Rando and Hogan, 1998, In: *Applied Antisense Oligonucleotide Technology*, eds. Krieg A M and Stein C, pp. 335-352; and Kimura Y et al., *J Biochem (Tokyo)* 116:991-4 (1994) also describe the immunostimulatory properties of poly-G nucleic acids.

Poly G nucleic acids preferably are nucleic acids having the following formulas:

$$5' X_1 X_2 G G G X_3 X_4 3'$$

wherein $X_1$, $X_2$, $X_3$, and $X_4$ are nucleotides. In preferred embodiments at least one of $X_3$ and $X_4$ are a G. In other embodiments both of $X_3$ and $X_4$ are a G. In yet other embodiments the preferred formula is 5' GGGNGGG 3', or 5' GGGNGGGNGGG 3' (SEQ ID NO:849) wherein N represents between 0 and 20 nucleotides. In other embodiments the poly-G nucleic acid is free of unmethylated CG dinucleotides, such as, for example, the nucleic acids listed in Table 4 below as SEQ ID NOs: 12-14, 23, 56, 100, 155, 163, 182, 227, 237, 246, 400, 407, 429, 430, 432, 435, 438, 439, 446, 450, 451, 480, 487, 493, 522, 661, 662, 671-673, 807, 808, 821, 823, and 834. In other embodiments the poly-G nucleic acid includes at least one unmethylated CG dinucleotide, such as, for example, the nucleic acids listed in Table 4 below as SEQ ID NOs: 6, 7, 22, 26, 28-30, 87, 115, 141, 177, 191, 209, 254, 258, 267, 303, 317, 329, 335, 344, 345, 395, 414, 417, 418, 423-426, 428, 431, 433, 434, 436, 437, 440, 442-445, 447-449, 458, 460, 463, 467-469, 474, 515, 516, 594, 638-640, 663, 664, 727, 752, 776, 795, 799, 817, 818, 831, and 832.

Nucleic acids having modified backbones, such as phosphorothioate backbones, also fall within the class of immunostimulatory nucleic acids. U.S. Pat. Nos. 5,723,335 and 5,663,153 issued to Hutcherson, et al. and related PCT publication WO95/26204 describe immune stimulation using phosphorothioate oligonucleotide analogues. These patents describe the ability of the phosphorothioate backbone to stimulate an immune response in a non-sequence specific manner.

The immunostimulatory nucleic acids may be any size but in some embodiments are in the range of between 6 and 100 or in some embodiments between 8 and 35 nucleotides in size. Immunostimulatory nucleic acids can be produced on a large scale in plasmids. These may be administered in plasmid form or alternatively they can be degraded into oligonucleotides.

"Palindromic sequence" shall mean an inverted repeat (i.e., a sequence such as ABCDEE'D'C'BA' in which A and A' are bases capable of forming the usual Watson-Crick base pairs and which includes at least 6 nucleotides in the palindrome. In vivo, such sequences may form double-stranded structures. In one embodiment the nucleic acid contains a palindromic sequence. In some embodiments when the nucleic acid is a CpG nucleic acid, a palindromic sequence used in this context refers to a palindrome in which the CpG is part of the palindrome, and optionally is the center of the palindrome. In another embodiment the nucleic acid is free of a palindrome. A nucleic acid that is free of a palindrome does not have any regions of 6 nucleotides or greater in length which are palindromic. A nucleic acid that is free of a palindrome can include a region of less than 6 nucleotides which are palindromic.

A "stabilized nucleic acid molecule" shall mean a nucleic acid molecule that is relatively resistant to in vivo degradation (e.g., via an exonuclease or endonuclease). Stabilization can be a function of length or secondary structure. Nucleic acids that are tens to hundreds of kbs long are relatively resistant to in vivo degradation. For shorter nucleic acids, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Some stabilized oligonucleotides of the instant invention have a modified backbone. It has been demonstrated that modification of the oligonucleotide backbone provides enhanced activity of the nucleic acids when administered in vivo. Nucleic acids, including at least two phosphorothioate linkages at the 5' end of the oligonucleotide and multiple phosphorothioate linkages at the 3' end, preferably 5, may provide maximal activity and protect the oligonucleotide from degradation by intracellular exo- and endo-nucleases. Other modified oligonucleotides include phosphodiester modified oligonucleotide, combinations of phosphodiester and phosphorothioate oligonucleotide, methylphosphonate, methylphosphorothioate, phosphorodithioate, and combinations thereof. Each of these combinations and their particular effects on immune cells is discussed in more detail in PCT Published Patent Application WO98/18810 claiming priority to U.S. Ser. No. 08/738,652 (now issued as U.S. Pat. No. 6,207,646 B1) and Ser. No. 08/960,774 (now issued as U.S. Pat. No. 6,239,116 B1), filed on Oct. 30, 1996 and Oct. 30, 1997 respectively, the entire contents of which is hereby incorporated by reference. It is believed that these modified oligonucleotides may show more stimulatory activity due to enhanced nuclease resistance, increased cellular uptake, increased protein binding, and/or altered intracellular localization. Both phosphorothioate and phosphodiester nucleic acids are active in immune cells.

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

For use in vivo, nucleic acids are preferably relatively resistant to degradation (e.g., via endonucleases and exonucleases). Secondary structures, such as stem loops, can stabilize nucleic acids against degradation. Alternatively, nucleic acid stabilization can be accomplished via phosphate backbone modifications. One type of stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al., *Chem Rev* 90:544-84 (1990); Goodchild J, *Bioconjugate Chem* 1:165-87 (1990).

The immunostimulatory nucleic acids having backbone modifications useful according to the invention in some embodiments are S- or R-chiral immunostimulatory nucleic acids. An "S chiral immunostimulatory nucleic acid" as used herein is an immunostimulatory nucleic acid wherein at least two nucleotides have a backbone modification forming a chiral center and wherein a plurality of the chiral centers have S chirality. An "R chiral immunostimulatory nucleic acid" as used herein is an immunostimulatory nucleic acid wherein at least two nucleotides have a backbone modification forming a chiral center and wherein a plurality of the chiral centers have R chirality. The backbone modification may be any type of modification that forms a chiral center. The modifications include but are not limited to phosphorothioate, methylphosphonate, methylphosphorothioate, phosphorodithioate, 2'-OMe and combinations thereof. In other embodiments they are non-chiral. A non-chiral nucleic acid is any nucleic acid which does not have at least two chiral centers.

The chiral immunostimulatory nucleic acids must have at least two nucleotides within the nucleic acid that have a backbone modification. All or less than all of the nucleotides in the nucleic acid, however, may have a modified backbone. Of the nucleotides having a modified backbone (referred to as chiral centers), a plurality have a single chirality, S or R. A "plurality" as used herein refers to an amount greater than or equal to 75%. Thus, less than all of the chiral centers may have S or R chirality as long as a plurality of the chiral centers have S or R chirality. In some embodiments at least 75%, 80%, 85%, 90%, 95%, or 100% of the chiral centers have S or R chirality. In other embodiments at least 75%, 80%, 85%, 90%, 95%, or 100% of the nucleotides have backbone modifications.

The S- and R- chiral immunostimulatory nucleic acids may be prepared by any method known in the art for producing chirally pure oligonucleotides. Stec et al. teach methods for producing stereopure phosphorothioate oligodeoxynucleotides using an oxathiaphospholane. Stec W J et al., *J Am Chem Soc* 117:12019 (1995). Other methods for making chirally pure oligonucleotides have been described by companies such as ISIS Pharmaceuticals. U.S. patents which disclose methods for generating stereopure oligonucleotides include U.S. Pat. Nos. 5,212,295, 5,359,052, 5,506,212, 5,512,668, 5,521,302, 5,599,797, 5,837,856, 5,856,465, and 5,883,237, each of which is hereby incorporated by reference in its entirety.

Other sources of nucleic acids useful according to the invention include standard viral and bacterial vectors, many of which are commercially available. In its broadest sense, a "vector" is any nucleic acid material which is ordinarily used to deliver and facilitate the transfer of nucleic acids to cells. The vector as used herein may be an empty vector or a vector carrying a gene which can be expressed. In the case when the vector is carrying a gene the vector generally transports the gene to the target cells with reduced degradation relative to the extent of degradation that would result in the absence of the vector. In this case the vector optionally includes gene expression sequences to enhance expression of the gene in target cells such as immune cells, but it is not required that the gene be expressed in the cell.

In general, vectors include, but are not limited to, plasmids, phagemids, viruses, other vehicles derived from viral or bacterial sources. Viral vectors are one type of vector and include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. Some viral vectors are based on non-cytopathic eukaryotic viruses in which non-essential genes have been replaced with a nucleic acid to be delivered. Non-cytopathic viruses include retroviruses, the life cycle of which involves reverse transcription of genomic viral RNA into DNA.

Standard protocols for producing empty vectors or vectors carrying genes (including the steps of incorporation of exogenous genetic material into a plasmid, transfection of a packaging cell lined with plasmid, production of recombinant retroviruses by the packaging cell line, collection of viral particles from tissue culture media, and/or infection of the target cells with viral particles) are provided in Kriegler M, "Gene Transfer and Expression, A Laboratory Manual," W.H. Freeman Co., New York (1990) and Murry E J, Ed., "Methods in Molecular Biology," vol. 7, Humana Press, Inc., Cliffton, N.J. (1991).

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. In the last few years, plasmid vectors have been found to be particularly advantageous for delivering genes to cells in vivo because of their inability to replicate within and integrate into a host genome. Some plasmids, however, having a promoter compatible with the host cell, can express a peptide from a gene operatively encoded within the plasmid. Some commonly used plasmids include pBR322, pUC18, pUC19, pcDNA3.1, pSV40, and pBlueScript. Other plasmids are well-known to those of ordinary skill in the art. Additionally, plasmids may be custom designed using restriction enzymes and ligation reactions to remove and add specific fragments of DNA.

It has recently been discovered that plasmids (empty or gene-carrying) can be delivered to the immune system using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to immune cells, e.g., dendritic cells, probably by passing through the gut barrier. High levels of immune protection have been established using this methodology. Such methods of delivery are useful for the aspects of the invention utilizing systemic delivery of nucleic acid.

As used herein, administration of an immunostimulatory nucleic acid is intended to embrace the administration of one or more immunostimulatory nucleic acids which may or may not differ in terms of their profile, sequence, backbone modifications and biological effect. As an example, CpG nucleic acids and T-rich nucleic acids may be administered to a single subject along with an antibody and optionally a cancer therapy. In another example, a plurality of CpG nucleic acids which differ in nucleotide sequence may also be administered to a subject.

Some of the nucleic acids useful according to the invention and described herein are presented in Table 4 below.

TABLE 4

Exemplary Nucleic Acids.

| SEQUENCE | BACKBONE | SEQ ID NO: |
|---|---|---|
| aaaaaa | s | 1 |
| aaaaaaaaaaaaaaaaaaaa | o | 2 |
| aaaaccccccccccaaaaa | o | 3 |
| aaaacatgacgttcaaaaaa | sos | 4 |
| aaaacatgacgttcaaaaaa | s2 | 5 |
| aaaacatgacgttcgggggg | sos | 6 |
| aaaacatgacgttcgggggg | s2 | 7 |
| aaaacgtt | o | 8 |

TABLE 4-continued

Exemplary Nucleic Acids.

| SEQUENCE | BACKBONE | SEQ ID NO: |
|---|---|---|
| aaaatcaacgttgaaaaaaa | sos | 9 |
| aaaatctgtgcttttaaaaaa | sos | 10 |
| aaaattgacgttttaaaaaa | sos | 11 |
| aaacattctgggggaattttaagaagtaaacat | o | 12 |
| aaacattctgggggaatttttaagaagttcctccctcccc | o | 13 |
| aaacattctgggggaattttgtctagtaaacat | o | 14 |
| aacgctcgaccttcgat | o | 15 |
| aacgctggaccttccat | o | 16 |
| aacgctggaccttccatgtc | sos | 17 |
| aacgtt | o | 18 |
| aacgttct | o | 19 |
| aacgttg | s | 20 |
| aacgttga | o | 21 |
| aacgttgaggggcat | o | 22 |
| aaggtggggcagtctcaggga | | 23 |
| aatagtcgccataacaaaac | o | 24 |
| aatagtcgccatcccccccc | o | 25 |
| aatagtcgccatcccgggac | o | 26 |
| aatagtcgccatcgcgcgac | o | 27 |
| aatagtcgccatggcggggc | o | 28 |
| aattctctatcggggcttctgtgtctgttgctggttccgctttat | o | 29 |
| acaaccacgagaacgggaac | | 30 |
| acaacgtt | o | 31 |
| acaacgttga | o | 32 |
| accacaacgagaggaacgca | | 33 |
| accatcctgaggccattcgg | | 34 |
| accatggacgaactgtttcccctc | s | 35 |
| accatggacgacctgtttcccctc | s | 36 |
| accatggacgagctgtttcccctc | s | 37 |
| accatggacgagctgtttcccctc | | 38 |
| accatggacgatctgtttcccctc | s | 39 |
| accatggacggtctgtttcccctc | s | 40 |
| accatggacgtactgtttcccctc | s | 41 |
| accatggacgttctgtttcccctc | s | 42 |
| acccatcaatagctctgtgc | s | 43 |
| acccgtcgtaattatagtaaaaccc | o | 44 |
| accgcatggattctaggcca | s | 45 |
| accttattaagattgtgcaatgtgacgtcctttagcatcgcaaga | o | 46 |
| acgctggaccttccat | | 47 |
| acgtcgttccccccccccc | o | 48 |
| acgtgt | s | 49 |
| actagacgttagtgtga | o | 50 |
| actagacgttagtgtga | s | 51 |
| actggacgttagcgtga | o | 52 |
| acttctcatagtcccttggtccag | o | 53 |
| agaacgtt | o | 54 |
| agacagacacgaaacgaccg | | 55 |
| agactcatgggaaaatcccacatttga | o | 56 |
| agatagcaaatcggctgacg | o | 57 |
| agatggttctcagataaagcggaa | | 58 |
| agcaccgaacgtgagagg | o | 59 |
| agcacggtagccttccta | | 60 |
| agcagctttagagctttagagctt | s | 61 |
| agcatcaggaacgacatgga | o | 62 |
| agcatcaggaccgacatgga | o | 63 |
| agcgctga | o | 64 |
| agctcaacgtcatgc | o | 65 |
| agctccatggtgctcactg | s | 66 |
| aggatatc | o | 67 |
| aggtacagccaggactacga | | 68 |
| agicccgigaacgiattcac | o | 69 |
| agtgactctccagcgttctc | o | 70 |
| agtgcgattcgagatctc | o | 71 |
| agtgcgattgcagatcg | o | 72 |
| agtgct | s | 73 |
| agtgct | o | 74 |
| agttgcaact | o | 75 |
| ataaagcgaaactagcagcagtttc | o | 76 |
| ataacgtt | o | 77 |
| ataatagagcttcaagcaag | s | 78 |
| ataatccagcttgaaccaag | s | 79 |
| ataatcgacgttcaagcaag | s | 80 |
| ataatcgacgttccccccccc | s | 81 |
| ataatcgtcgttcaagcaag | s | 82 |
| ataatcgtgcgttcaagaaag | s | 83 |

TABLE 4-continued

Exemplary Nucleic Acids.

| SEQUENCE | BACKBONE | SEQ ID NO: |
|---|---|---|
| atagacaaaaattccctccccggagcc | o | 84 |
| atatatatatatatat | s | 85 |
| atatctaatcaaaacattaacaaa | o | 86 |
| atcaggaacgtcatgggaagc | o | 87 |
| atcgacctacgtgcgttctc | o | 88 |
| atcgacctacgtgcgttztc | o | 89 |
| atcgactcgagcgttctc | o | 90 |
| atcgactctcgagcgttctc | o | 91 |
| atcgactctcgagcgttctc | sos | 92 |
| atcgactctcgagtgttctc | o | 93 |
| atcgactctcgagzgttctc | o | 94 |
| atcgactctctcgagcgttctc | o | 95 |
| atcgacttcgagcgttctc | o | 96 |
| atcgatcgagcgttctc | o | 97 |
| atcgatgt | o | 98 |
| atcggaggactggcgcgccg | | 99 |
| atctggtgagggcaagctatg | s | 100 |
| atgacgttcctgacgtt | s | 101 |
| atgcactctgcagcgttctc | o | 102 |
| atgcatgt | o | 103 |
| atgcccctcaacgtt | o | 104 |
| atgctaaaggacgtcacattgca | o | 105 |
| atggaaggtccacgttctc | o | 106 |
| atggaaggtccagcgttct | o | 107 |
| atggaaggtccagcgttctc | o | 108 |
| atggaaggtccagtgttctc | o | 109 |
| atggaaggtcgagcgttctc | o | 110 |
| atggactctccagcgttctc | o | 111 |
| atgtcctcggtcctgatgct | o | 112 |
| atgtttactagacaaaattcccccagaatgttt | o | 113 |
| atgtttacttcttaaaattcccccagaatgttt | o | 114 |
| attcgatcggggcgggggcgag | o | 115 |
| atzgacctacgtgcgttctc | o | 116 |
| atzgactctzgagzgttctc | o | 117 |
| batggaaggtccagcgttctc | o | 118 |
| bgagaacgctccagcactgat | o | 119 |
| bgagaacgctcgaccttcgat | o | 120 |
| bgagaazgctccagcactgat | o | 121 |
| bgagaazgctcgaccttcgat | o | 122 |
| bgagaaagctggaccttccat | o | 123 |
| bgagcaagztggaccttccat | o | 124 |
| bgctagacgttagcgtga | o | 125 |
| btcaacgtt | o | 126 |
| btccatgacgttcctgatgct | o | 127 |
| btccatgagcttcctgatgct | o | 128 |
| btccattccatgacgttcctgatgcttcca | os | 129 |
| btccattccattctaggcctgagtcttccat | os | 130 |
| btcgtcgttttgtcgttttgtcgttttt | os | 131 |
| bttttttccatgtcgttcctgatgctttttt | os | 132 |
| bttttttcgtcgttcccccccccccc | os | 133 |
| caaacgtt | o | 134 |
| caacgtt | o | 135 |
| caagagatgctaacaatgca | s | 136 |
| caataaatctgaggagaccc | | 137 |
| cacaccttggtcaatgtcacgt | o | 138 |
| caccaccttggtcaatgtcacgt | o | 139 |
| cacggtagccttccta | | 140 |
| cacgttgaggggcat | s | 141 |
| cactgtccttcgtcga | sos | 142 |
| cagacacagaagcccgatagacg | | 143 |
| cagattgtgcaatgtctcga | o | 144 |
| cataacataggaatatttactcctcgc | o | 145 |
| cataggatctcgagctcggaaagtcccctac | o | 146 |
| catgagctcatctggaggaagcgg | o | 147 |
| catttccacgatttccca | o | 148 |
| cattttacgggcgggcgggc | | 149 |
| ccaaatatcggtggtcaagcac | | 150 |
| ccaacgtt | s | 151 |
| ccacgtcgaccctcaggcga | s | 152 |
| ccacgtggacctctagc | o | 153 |
| ccactcacatctgctgctccacaag | o | 154 |
| ccagatgagctcatgggtttctcc | o | 155 |
| ccaggttaagaggaaatgacttcggg | o | 156 |
| ccaggttgtatagaggc | | 157 |
| ccagtgctgatcaccgatatcctgttcggcagtcg | | 158 |

TABLE 4-continued

Exemplary Nucleic Acids.

| SEQUENCE | BACKBONE | SEQ ID NO: |
|---|---|---|
| ccatcgat | o | 159 |
| ccatgcat | o | 160 |
| ccatgctaacctctagc | o | 161 |
| ccatgtcggtcctgatgct | o | 162 |
| ccccaaagggatgagaagtt | o | 163 |
| ccccaaaaaaaaaaccccc | o | 164 |
| cccccc | s | 165 |
| ccccccc | s | 166 |
| cccccccccc | s | 167 |
| cccccccccccccccccc | s | 168 |
| cccccccccccccccccc | sos | 169 |
| ccccccccccccccccccccc | s | 170 |
| ccccccccccccccccccccccccc | s | 171 |
| ccccccccccccccccccccccccccccccc | s | 172 |
| cccccttgacgttttcccccc | sos | 173 |
| cccgaagtcatttcctcttaacctgg | o | 174 |
| ccgaacaggatatcggtgatcagcac | | 175 |
| ccgcttcctccagatgagctcatg | o | 176 |
| ccgcttcctccagatgagctcatgggtttctccaccaag | o | 177 |
| ccggccggccggccggccgg | o | 178 |
| ccgtcgttccccccccccc | o | 179 |
| cctacgttgtatgcgcccagct | o | 180 |
| cctccaaatgaaagaccccc | | 181 |
| cctctatacaacctgggac | | 182 |
| ccttccatgtcggtcctgat | sos | 183 |
| ccttcgat | o | 184 |
| cgaacgtt | o | 185 |
| cgacga | o | 186 |
| cgacgt | s | 187 |
| cgactctcgagcgttctc | o | 188 |
| cgactgccgaacaggatatcggtgatcagcactgg | | 189 |
| cgccgtcgcggcggttgg | o | 190 |
| cgcctggggctggtctgg | o | 191 |
| cgcgcgcgcgcgcgcgcg | s | 192 |
| cgcgcgcgcgcgcgcgcg | o | 193 |
| cgcgta | s | 194 |
| cgctagaggttagcgtga | o | 195 |
| cgctggaccttccat | o | 196 |
| cgctggaccttccatgtcgg | sos | 197 |
| cggctgacgtcatcaa | s | 198 |
| cgggcgactcagtctatcgg | | 199 |
| cgggcttacggcggatgctg | | 200 |
| cggtagccttccta | | 201 |
| cgtaccttacggtga | o | 202 |
| cgtacg | s | 203 |
| cgtcga | s | 204 |
| cgtcga | o | 205 |
| cgtcgt | s | 206 |
| cgtcgtcgt | o | 207 |
| cgtcgtcgtcgtcgtcgt | s | 208 |
| cgtctatcgggcttctgtgtctg | | 209 |
| cgttcg | s | 210 |
| ctaacgtt | o | 211 |
| ctaatctttctaatttttttctaa | s | 212 |
| ctagataaagcggaaccagcaacagacacagaagccccgatagag | o | 213 |
| ctagcgct | o | 214 |
| ctagcggctgacgtcataaagctagc | s | 215 |
| ctagcggctgacgtcatcaagctag | o | 216 |
| ctagcggctgacgtcatcaatctag | o | 217 |
| ctagcggctgagctcataaagctagc | s | 218 |
| ctagcttgatgacgtcagccgctag | o | 219 |
| ctagcttgatgagctcagccgctag | o | 220 |
| ctagctttatgacgtcagccgctagc | s | 221 |
| ctaggctgacgtcatcaagctagt | o | 222 |
| ctagtggctgacgtcatcaagctag | s | 223 |
| ctatcggaggactggcgcgcc | | 224 |
| ctatcggaggactggcgcgcg | | 225 |
| ctcaacgctggaccttccat | o | 226 |
| ctcatgggtttctccaccaag | o | 227 |
| ctccagctccaagaaaggacg | o | 228 |
| ctcgccccgccccgatcgaat | o | 229 |
| ctctccaagctcacttacag | | 230 |
| ctctctgtaggcccgcttgg | s | 231 |
| ctcttgcgacctggaaggta | | 232 |
| ctgacgtcat | o | 233 |

TABLE 4-continued

Exemplary Nucleic Acids.

| SEQUENCE | BACKBONE | SEQ ID NO: |
|---|---|---|
| ctgacgtg | o | 234 |
| ctgattgctctctcgtga | sos | 235 |
| ctgattgctctctcgtga | o | 236 |
| ctgcagcctgggac | o | 237 |
| ctgcgttagcaatttaactgtg | o | 238 |
| ctgctgagactggag | s | 239 |
| ctgctgctgctgctgctg | | 240 |
| ctggaccttccatgtc | sos | 241 |
| ctggaccttccatgtcgg | sos | 242 |
| ctggtctttctggttttttctgg | s | 243 |
| ctggtctttctggttttttctgg | o | 244 |
| ctgtaagtgagcttggagag | | 245 |
| ctgtatgaaacaaattttcctctttgggca | o | 246 |
| ctgtca | s | 247 |
| ctgtcaggaactgcaggtaagg | o | 248 |
| ctgtcccatattttagaca | | 249 |
| ctgtcg | s | 250 |
| ctgtcg | o | 251 |
| ctgtcgttcccccccccccc | o | 252 |
| ctgtgctttctgtgtttttctgtg | s | 253 |
| cttggagggcctcccggcgg | | 254 |
| cttggtggagaaacccatgag | o | 255 |
| cttggtggagaaacccatgagctcatctggaggaagcgg | o | 256 |
| cttttccgttggaccctggg | s | 257 |
| czggczggczgggczccgg | o | 258 |
| faacgttga | o | 259 |
| fcgcgaattcgcg | o | 260 |
| ftcaacgtt | o | 261 |
| gaaacgtt | o | 262 |
| gaaactgctgctagtttcgctttat | o | 263 |
| gaaccttccatgctgtt | | 264 |
| gaaccttccatgctgttccg | | 265 |
| gaacgctggaccttccat | | 266 |
| gaagttcacgttgaggggcat | o | 267 |
| gaagtttctggtaagtcttcg | o | 268 |
| gaccttccat | | 269 |
| gaccttccatgtcggtcctgat | | 270 |
| gaccttctatgtcggtcctg | | 271 |
| gacgtcat | o | 272 |
| gactgacgtcagcgt | o | 273 |
| gagaacgatggaccttccat | o | 274 |
| gagaacgctagaccttctat | o | 275 |
| gagaacgctccaccttccat | o | 276 |
| gagaacgctccagcactgat | o | 277 |
| gagaacgctccagcttgat | o | 278 |
| gagaacgctccgaccttcgat | s | 279 |
| gagaacgctcgaccttccat | o | 280 |
| gagaacgctcgaccttcgatb | s | 281 |
| gagaacgctggacctatccat | o | 282 |
| gagaacgctggacctcatcatccat | o | 283 |
| gagaacgctggacctcatccat | o | 284 |
| gagaacgctggaccttcc | | 285 |
| gagaacgctggaccttccat | | 286 |
| gagaacgctggaccttccat | s | 287 |
| gagaacgctggaccttccatgt | | 288 |
| gagaacgctggaccttcgat | o | 289 |
| gagaacgctggaccttcgta | o | 290 |
| gagaacgctggaccttgcat | o | 291 |
| gagaacgctggacgctcatccat | o | 292 |
| gagaacgctggacttccat | o | 293 |
| gagaacgctggaczttccat | o | 294 |
| gagaacgctggatccat | o | 295 |
| gagaatgctggaccttccat | o | 296 |
| gagaazgctggaccttccat | o | 297 |
| gagaccgctcgaccttcgat | | 298 |
| gagcaagctggaccttccat | s | 299 |
| gagcaagctggaccttccatb | s | 300 |
| gaggaacgtcatggagaggaacgtcatggagaggaacgtcatgga | o | 301 |
| gaggaaggigiggaigacgt | o | 302 |
| gagggggaccatttttacgggc | | 303 |
| gatccagattctgccaggtcactgtgactggat | o | 304 |
| gatccagattctgctgagtcactgtgactggat | o | 305 |
| gatccagtcacagtgacctggcagaatctggat | o | 306 |
| gatccagtcacagtgactcagcagaatctggat | o | 307 |
| gatccggctgactcatcactagatc | o | 308 |

TABLE 4-continued

Exemplary Nucleic Acids.

| SEQUENCE | BACKBONE | SEQ ID NO: |
|---|---|---|
| gatcgctgatctaatgctcg | sos | 309 |
| gatcggaggactggcgcgccg | | 310 |
| gatctagtgatgagtcagccggatc | o | 311 |
| gattcaacttgcgctcatcttaggc | o | 312 |
| gcaacgtt | o | 313 |
| gcaatattgcb | o | 314 |
| gcaatattgcf | o | 315 |
| gcacatcgtcccgcagccga | s | 316 |
| gcagcctctatacaacctgggacggga | | 317 |
| gcatagcgttgagct | sos | 318 |
| gcatgacgttgagct | s | 319 |
| gcatgacgttgagct | sos | 320 |
| gcatgacgttgagct | o | 321 |
| gcatgacgttgagct | s | 322 |
| gcatgagcttgagctga | o | 323 |
| gcatgatgttgagct | o | 324 |
| gcatgazgttgagct | o | 325 |
| gcatggcgttgagct | sos | 326 |
| gcatgtagctgagct | o | 327 |
| gcatgtcgttgagct | sos | 328 |
| gcattcatcaggcgggcaagaat | o | 329 |
| gcattgcgttgagct | sos | 330 |
| gcatttcgaggagct | o | 331 |
| gccaccaaaacttgtccatg | | 332 |
| gccagatgttagctgga | o | 333 |
| gccatggacgaactgttcccctc | s | 334 |
| gcgacgggcggcgcgcgccc | s | 335 |
| gcgacggtcggcgcgcgccc | s | 336 |
| gcgacgtgcggcgcgcgccc | s | 337 |
| gcgacgttcggcgcgcgccc | s | 338 |
| gcgatgtcgttcctgatgcg | o | 339 |
| gcgatgtcgttcctgatgct | o | 340 |
| gcgccagtcctccgatagac | | 341 |
| gcgcgcgcgcgcgcgcgcg | o | 342 |
| gcgctaccggtagcctgagt | | 343 |
| gcggcgggcggcgcgcgccc | o | 344 |
| gcggcgggcggcgcgcgccc | s | 345 |
| gcggcggtcggcgcgcgccc | s | 346 |
| gcggcgtgcggcgcgcgccc | s | 347 |
| gcggcgttcggcgcgcgccc | s | 348 |
| gcgtcgttccccccccccc | o | 349 |
| gcgtgcgttgtcgttgtcgtt | s | 350 |
| gcgttttttttgcg | s | 351 |
| gctaaacgttagcgt | o | 352 |
| gctaacgttagcgtga | o | 353 |
| gctaccttagcgtga | o | 354 |
| gctaccttagzgtga | o | 355 |
| gctacttagcgtga | o | 356 |
| gctagacgatagcgt | o | 357 |
| gctagacgctagcgtga | o | 358 |
| gctagacgt | o | 359 |
| gctagacgtaagcgtga | o | 360 |
| gctagacgtctagc | o | 361 |
| gctagacgttagc | o | 362 |
| gctagacgttagcgt | o | 363 |
| gctagacgttagcgtga | | 364 |
| gctagacgttagctgga | o | 365 |
| gctagacgttagctgga | sos | 366 |
| gctagacgttaggctga | o | 367 |
| gctagacgttagtgt | o | 368 |
| gctagacgttagzgt | o | 369 |
| gctagacgtttagc | o | 370 |
| gctagagcttagcgtga | o | 371 |
| gctagaggttagcgtga | o | 372 |
| gctagaggttagcgtga | s | 373 |
| gctagatgttaacgt | o | 374 |
| gctagatgttagcgt | o | 375 |
| gctagatgttagcgt | s | 376 |
| gctagatgttagcgtga | o | 377 |
| gctagazgttagcgt | o | 378 |
| gctagazgttagtgt | o | 379 |
| gctagctttagagctttagagctt | o | 380 |
| gctaggcgttagcgt | o | 381 |
| gctagtcgatagc | o | 382 |
| gctagtcgatagcgt | o | 383 |

TABLE 4-continued

Exemplary Nucleic Acids.

| SEQUENCE | BACKBONE | SEQ ID NO: |
|---|---|---|
| gctagtcgctagc | o | 384 |
| gctandcghhagc | o | 385 |
| gctatgacgttccaaggg | s | 386 |
| gctcga | s | 387 |
| gctcgttcagcgcgtct | sos | 388 |
| gctgaaccttccatgctgtt | | 389 |
| gctgagctcatgccgtctgc | sos | 390 |
| gctggaccttccat | | 391 |
| gctggaccttccat | o | 392 |
| gctggccagcttacctcccg | | 393 |
| gctgtaaaatgaatcggccg | sos | 394 |
| gctgtgggcggctcctg | s | 395 |
| gcttgacgtcaagc | o | 396 |
| gcttgacgtctagc | o | 397 |
| gcttgacgtttagc | o | 398 |
| gcttgcgttgcgtttt | sos | 399 |
| gcttggagggcctgtaagtg | | 400 |
| ggaacgtt | o | 401 |
| ggaagacgttaga | o | 402 |
| ggaattagtaatagatatagaagtt | o | 403 |
| ggagaaacccatgagctcatctgg | o | 404 |
| ggagctcttcgaacgccata | | 405 |
| ggcagtgcaggctcaccggg | | 406 |
| ggccaactttcaatgtgggatggcctc | | 407 |
| ggccatcccacattgaaagtt | | 408 |
| ggccttttcccccccccccc | o | 409 |
| ggcggcggcggcggcggcgg | o | 410 |
| ggcgttattcctgactcgcc | o | 411 |
| ggctatgtcgatcctagcc | o | 412 |
| ggctatgtcgttcctagcc | o | 413 |
| ggctccggggagggaattttttgtctat | o | 414 |
| ggctgtattcctgactgccc | s | 415 |
| gggaatgaaagattttattataag | o | 416 |
| ggggactttccgctggggactttccaggggggactttcc | sos | 417 |
| ggggagggaggaacttcttaaaattcccccagaatgtttt | o | 418 |
| ggggagggg | s | 419 |
| ggggagggt | s | 420 |
| ggggcatgacgttcaaaaaa | s | 421 |
| ggggcatgacgttcaaaaaa | sos | 422 |
| ggggcatgacgttcgggggg | s2 | 423 |
| ggggcatgacgttcgggggg | sos | 424 |
| ggggcatgagcttcgggggg | s | 425 |
| ggggcatgagcttcgggggg | sos | 426 |
| ggggcctctatacaacctggg | | 427 |
| gggggacgttggggg | o | 428 |
| ggggggggggggggggggggg | sos | 429 |
| ggggggggggggggggggggg | o | 430 |
| gggggggttgggggaaaacccggacttcctgca | o | 431 |
| gggggttttttttttgggggg | o | 432 |
| ggggtaatcgatcagggggg | sos | 433 |
| ggggtaatcgatgagggggg | o | 434 |
| ggggtaatgcatcagggggg | sos | 435 |
| ggggtcaacgttgagggggg | sos | 436 |
| ggggtcaacgttgagggggg | s | 437 |
| ggggtcaagcttgagggggg | sos | 438 |
| ggggtcaagtctgagggggg | sos | 439 |
| ggggtccagcgtgcgccatggggg | sos | 440 |
| ggggtccctgagactgcc | | 441 |
| ggggtcgaccttggagggggg | sos | 442 |
| ggggtcgacgtcgagggggg | s | 443 |
| ggggtcgtcgttttgggggg | | 444 |
| ggggtctgtcgttttgggggg | sos | 445 |
| ggggtctgtgcttttgggggg | sos | 446 |
| ggggtgacgttcaggggggg | sos | 447 |
| ggggtgtcgttcaggggggg | sos | 448 |
| ggggttgacgttttggggggg | sos | 449 |
| ggggttggggtt | s | 450 |
| ggtacctgtggggacattgtg | o | 451 |
| ggtgaggtg | s | 452 |
| ggtggtgtaggttttgg | o | 453 |
| ggttacggtctgtccatat | | 454 |
| ggttcacgtgctcatggctg | o | 455 |
| gtaacgtt | o | 456 |
| gtagccttccta | | 457 |
| gtaggggactttccgagctcgagatcctatg | o | 458 |

TABLE 4-continued

Exemplary Nucleic Acids.

| SEQUENCE | BACKBONE | SEQ ID NO: |
|---|---|---|
| gtcactcgtggtacctcga | s | 459 |
| gtccatggcgtgcgggatga | | 460 |
| gtcccaggttgtatagaggctgc | | 461 |
| gtccccatttcccagaggaggaaat | o | 462 |
| gtccgggccaggccaaagtc | s | 463 |
| gtcggtcctgatgctgttcc | sos | 464 |
| gtctatcggaggactggcgc | | 465 |
| gtctgtcccatgatctcgaa | | 466 |
| gtgaaticgttcicgggict | o | 467 |
| gtgccggggtctccgggc | s | 468 |
| gtgccggggtctccgggc | o | 469 |
| gtgcgcgcgagcccgaaatc | s | 470 |
| gtgctgatcaccgatatcctgttcgg | | 471 |
| gtgcttgaccaccgatatttgg | | 472 |
| gtggttacggtcgtgcccat | | 473 |
| gtgtcggggtctccgggc | o | 474 |
| gttctcagataaagcggaaccagcaacagacacagaa | | 475 |
| gttgaaacccgagaacatcat | s | 476 |
| gttggatacaggccagactttgttg | o | 477 |
| gtttttatataatttggg | o | 478 |
| gzaatattgcb | o | 479 |
| gzggzgggzggzgzgzgccc | | 480 |
| taaacgtt | s | 481 |
| taagcgct | o | 482 |
| taagctctgtcaacgccagg | | 483 |
| taccgagcttcgacgagatttca | o | 484 |
| taccgcgtgcgaccctct | s | 485 |
| tactcttcggatcccttgcg | sos | 486 |
| tagaaacagcattcttcttttagggcagcaca | | 487 |
| tagacgtc | o | 488 |
| tagacgttagcgtga | o | 489 |
| tatagtccctgagactgccccaccttctcaacaacc | | 490 |
| tatcggaggactggcgcgccg | | 491 |
| tatgccgcgcccggacttat | sos | 492 |
| tcaaatgtgggattttcccatgagtct | o | 493 |
| tcaacgt | s | 494 |
| tcaacgtc | o | 495 |
| tcaacgtt | p-ethoxy | 496 |
| tcaacgtt | s | 497 |
| tcaacgtt | o | 498 |
| tcaacgttaacgttaacgtt | o | 499 |
| tcaacgttaacgttaacgttaacgttb | s | 500 |
| tcaacgttga | s | 501 |
| tcaacgttga | o | 502 |
| tcaacgttgab | o | 503 |
| tcaacgttgaf | o | 504 |
| tcaagctt | p-ethoxy | 505 |
| tcaagctt | o | 506 |
| tcaatgctgaf | o | 507 |
| tcaazgtt | o | 508 |
| tcaazgttgab | o | 509 |
| tcaccggt | s | 510 |
| tcacgctaacctctagc | o | 511 |
| tcacgctaacctctgac | o | 512 |
| tcacgctaacgtctagc | o | 513 |
| tcacgt | o | 514 |
| tcagaccacgtggtcggtgttcctga | o | 515 |
| tcagaccagctggtcggtgttcctga | o | 516 |
| tcagcgct | o | 517 |
| tcagcgtgcgcc | s | 518 |
| tcagctctggtactttttca | | 519 |
| tcaggaacacccgaccacgtggtctga | o | 520 |
| tcaggaacacccgaccagctggtctga | o | 521 |
| tcagggtgggggaacctt | sos | 522 |
| tcagzgct | o | 523 |
| tcatcgat | o | 524 |
| tccaagacgttcctgatgct | o | 525 |
| tccaagtagttcctagttct | o | 526 |
| tccaccacgtggctgatgct | o | 527 |
| tccaccacgtggtctatgct | s | 528 |
| tccacgactttttcgacgtt | s | 529 |
| tccagacggtgaagt | o | 530 |
| tccagacgttgaagt | o | 531 |
| tccagagcttgaagt | o | 532 |
| tccagcgtgcgccata | sos | 533 |

TABLE 4-continued

Exemplary Nucleic Acids.

| SEQUENCE | BACKBONE | SEQ ID NO: |
|---|---|---|
| tccaggacgttcctagttct | o | 534 |
| tccaggacttctctcaggtt | s | 535 |
| tccaggacttctctcaggtt | sos | 536 |
| tccaggactttcctcaggtt | s | 537 |
| tccaggactttcctcaggtt | o | 538 |
| tccaggagcttcctagttct | o | 539 |
| tccaggatgttcctagttct | o | 540 |
| tccagtctaggcctagttct | o | 541 |
| tccagttccttcctcagtct | o | 542 |
| tccagttcgagcctagttct | o | 543 |
| tccataacgttcctgagtct | sos | 544 |
| tccataacgttcctgatgct | o | 545 |
| tccatagcgatcctagcgat | o | 546 |
| tccatagcggtcctagcggt | o | 547 |
| tccatagcgttcctagcgtt | s | 548 |
| tccatagcgttcctagcgtt | o | 549 |
| tccatcacgtgcctgagtct | sos | 550 |
| tccatgacattcctgatgct | o | 551 |
| tccatgacggtcctgacggt | s | 552 |
| tccatgacggtcctgacggt | o | 553 |
| tccatgacggtcctgagtct | sos | 554 |
| tccatgacggtcctgatgct | s | 555 |
| tccatgacgtccctgagtct | sos | 556 |
| tccatgacgtccctgatgct | o | 557 |
| tccatgacgttcctagttct | o | 558 |
| tccatgacgttcctctccatgacgttcctctccatgacgttcctc | o | 559 |
| tccatgacgttcctgacgtt | s | 560 |
| tccatgacgttcctgacgtt |  | 561 |
| tccatgacgttcctgacgtt | sos | 562 |
| tccatgacgttcctgacgtt | o | 563 |
| tccatgacgttcctgagtct | sos | 564 |
| tccatgacgttcctgatcc |  | 565 |
| tccatgacgttcctgatgct | o | 566 |
| tccatgacgttcctgatgct | s | 567 |
| tccatgacgttcctgcagttcctgacgtt | s | 568 |
| tccatgacgttcctgccgtt | s | 569 |
| tccatgacgttcctgcgttt | s | 570 |
| tccatgacgttcctggcggg | s | 571 |
| tccatgacgttcztgatgct | o | 572 |
| tccatgagcttcctgagctt | s | 573 |
| tccatgagcttcctgagtct | o | 574 |
| tccatgagcttcctgagtct | p-ethoxy | 575 |
| tccatgagcttcctgagtct | s | 576 |
| tccatgagcttcctgatgct | s2 | 577 |
| tccatgagcttccttgagtct |  | 578 |
| tccatgaigttcctgaigtt | s | 579 |
| tccatgatgttcctagttct | o | 580 |
| tccatgazgttcctagttct | o | 581 |
| tccatgazgttcctgatgct | o | 582 |
| tccatgazgttcctgazgtt | s | 583 |
| tccatgccggtcctgagtct | sos | 584 |
| tccatgccggtcctgatgct | o | 585 |
| tccatgccggtcctgccggt | o | 586 |
| tccatgccgttcctgccgtt | s | 587 |
| tccatgccgttcctgccgtt | o | 588 |
| tccatgcgcgtcctgcgcgt | o | 589 |
| tccatgcgtgcgtgcgtttt | s | 590 |
| tccatgcgttgcgttgcgtt | s | 591 |
| tccatgctggtcctgagtct | sos | 592 |
| tccatgctggtcctgatgct | o | 593 |
| tccatggcgggcctggcggg | s | 594 |
| tccatggcggtcctgatgct | o | 595 |
| tccatgtagttcctagttct | o | 596 |
| tccatgtccttcctgatgct |  | 597 |
| tccatgtcgatcctgagtct | sos | 598 |
| tccatgtcgatcctgatgct | o | 599 |
| tccatgtcgctcctgagtct | sos | 600 |
| tccatgtcgctcctgatcct | o | 601 |
| tccatgtcggtcctgagtct | sos | 602 |
| tccatgtcggtcctgatgct |  | 603 |
| tccatgtcggtcctgatgct | s | 604 |
| tccatgtcggtcctgctgat | o | 605 |
| tccatgtcggtzctgatgct | o | 606 |
| tccatgtcgttccgcgcgcg | o | 607 |
| tccatgtcgttcctagttct |  | 608 |

TABLE 4-continued

Exemplary Nucleic Acids.

| SEQUENCE | BACKBONE | SEQ ID NO: |
|---|---|---|
| tccatgtcgttcctgagtct | sos | 609 |
| tccatgtcgttcctgatgcg | o | 610 |
| tccatgtcgttcctgatgct | o | 611 |
| tccatgtcgttcctgccgct | o | 612 |
| tccatgtcgttcctgtagct | o | 613 |
| tccatgtcgttcctgtcgtt | s | 614 |
| tccatgtcgttcctgtcgtt | o | 615 |
| tccatgtcgtttttgtcgtt | s | 616 |
| tccatgtgcttcctgatgct | o | 617 |
| tccatgtzggtcctgagtct | sos | 618 |
| tccatgtzggtcctgatgct | o | 619 |
| tccatgtzgttcctgatgct | o | 620 |
| tccatgtzgttcctgtzgtt | s | 621 |
| tccattgcgttccttgcgtt | o | 622 |
| tcccgacggtgaagt | o | 623 |
| tcccgccgttgaagt | o | 624 |
| tcccgcgcgttccgcgcgtt | s | 625 |
| tccctgagactgccccacctt |  | 626 |
| tccgatcg | o | 627 |
| tccggacggtgaagt | o | 628 |
| tccggccgttgaagt | o | 629 |
| tccgtacg | o | 630 |
| tcctaacgttgaagt | o | 631 |
| tcctagcgttgaagt | o | 632 |
| tcctcacgttgaagt | o | 633 |
| tcctga | o | 634 |
| tcctgaaaaggaagt | s | 635 |
| tcctgacgatgaagt | o | 636 |
| tcctgacgctgaagt | o | 637 |
| tcctgacggggaagt | o | 638 |
| tcctgacggggaagt | s | 639 |
| tcctgacggggagt | s | 640 |
| tcctgacggtgaagt | o | 641 |
| tcctgacggtgaagt | s | 642 |
| tcctgacgtagaagt | o | 643 |
| tcctgacgtcgaagt | o | 644 |
| tcctgacgtggaagt | o | 645 |
| tcctgacgtggaagt | s | 646 |
| tcctgacgttaga | o | 647 |
| tcctgacgttccc | o | 648 |
| tcctgacgttccctggcggtccctgtcgct | o | 649 |
| tcctgacgttcctgacgtt | s | 650 |
| tcctgacgttcctggcggtcctgtcgct | o | 651 |
| tcctgacgttccttc | o | 652 |
| tcctgacgttcggcgcgcgccc | s | 653 |
| tcctgacgttgaagt | o | 654 |
| tcctgacgttgaagt | s | 655 |
| tcctgagcttgaagt | o | 656 |
| tcctgagcttgaagt | s | 657 |
| tcctgazgttgaagt | o | 658 |
| tcctgccgttgaagt | o | 659 |
| tcctgccgttgaagt | s | 660 |
| tcctggaggggaagt | o | 661 |
| tcctggaggggaagt | s | 662 |
| tcctggcggggaagt | o | 663 |
| tcctggcggggaagt | s | 664 |
| tcctggcggtcctggcggtt | s | 665 |
| tcctggcggtgaagt | o | 666 |
| tcctggcggtgaagt | s | 667 |
| tcctggcgtggaagt | o | 668 |
| tcctggcgttgaagt | o | 669 |
| tcctggcgttgaagt | s | 670 |
| tcctgggggggaagt | o | 671 |
| tcctggtggggaagt | o | 672 |
| tcctggzggggaagt | o | 673 |
| tcctgtcgctcctgtcgct | o | 674 |
| tcctgtcgctcctgtcgctcctgtcgct | o | 675 |
| tcctgtcgttcctgtcgtt | s | 676 |
| tcctgtcgttcctgtcgttggaacgacagg | o | 677 |
| tcctgtcgttcctgtcgtttcaacgtcaggaacgacagga | o | 678 |
| tcctgtcgttccttgtcgt | s | 679 |
| tcctgtcgttgaagt | o | 680 |
| tcctgtcgttgaagttttttt | o | 681 |
| tcctgtcgtttttgtcgtt | s | 682 |
| tccttacgttgaagt | o | 683 |

TABLE 4-continued

Exemplary Nucleic Acids.

| SEQUENCE | BACKBONE | SEQ ID NO: |
|---|---|---|
| tccttgtcgttcctgtcgtt | s | 684 |
| tcgacgtc | o | 685 |
| tcgacgttcccccccccccc | o | 686 |
| tcgagacattgcacaatcatctg | o | 687 |
| tcgccgttcccccccccccc | o | 688 |
| tcgcgtgcgttttgtcgttttgacgtt | s | 689 |
| tcgga | o | 690 |
| tcggcgttcccccccccccc | o | 691 |
| tcgtag | s | 692 |
| tcgtca | o | 693 |
| tcgtcattcccccccccccc | o | 694 |
| tcgtcgatcccccccccccc | o | 695 |
| tcgtcgctcccccccccccc | o | 696 |
| tcgtcgctgtctccg | s | 697 |
| tcgtcgctgtctccgcttctt | s | 698 |
| tcgtcgctgtctccgcttctt | so | 699 |
| tcgtcgctgtctccgcttctt | s2o | 700 |
| tcgtcgctgtctccgcttcttcttgcc | s | 701 |
| tcgtcgctgtctgcccttctt | s | 702 |
| tcgtcgctgttgtcgtttctt | s | 703 |
| tcgtcggtcccccccccccc | o | 704 |
| tcgtcgtcagttcgctgtcg | sos | 705 |
| tcgtcgtcgtcgtcgtcgtt | sos | 706 |
| tcgtcgtcgtcgtt | s | 707 |
| tcgtcgtcgtcgtt | s2 | 708 |
| tcgtcgtcgtcgtt | s2o | 709 |
| tcgtcgtcgtcgtt | os2 | 710 |
| tcgtcgttcccccccccc | s | 711 |
| tcgtcgttcccccccccccc | o | 712 |
| tcgtcgttcccccccccccb | o | 713 |
| tcgtcgttcccccccczcccc | o | 714 |
| tcgtcgttggtgtcgttggtgtcgtt | s | 715 |
| tcgtcgttggttgtcgttttggtt | s | 716 |
| tcgtcgttgtcgttgtcgtt | s | 717 |
| tcgtcgttgtcgttgtcgtt | sos | 718 |
| tcgtcgttgtcgttttgtcgtt | s | 719 |
| tcgtcgttgtcgttttgtcgtt | sos | 720 |
| tcgtcgtttcgtcgttttgacgtt | s | 721 |
| tcgtcgtttgcgtgcgtttcgtcgtt | s | 722 |
| tcgtcgtttgtcgttttgtcgtt | s | 723 |
| tcgtcgttttgacgttttgacgtt | s | 724 |
| tcgtcgttttgacgttttgtcgtt | s | 725 |
| tcgtcgttttgcgtgcgttt | s | 726 |
| tcgtcgttttgtcgttttgggggg | | 727 |
| tcgtcgttttgtcgttttgtcgt | s2 | 728 |
| tcgtcgttttgtcgttttgtcgtt | s | 729 |
| tcgtcgttttgtcgttttgtcgtt | sos | 730 |
| tcgtcgttttgtcgttttgtcgtt | o | 731 |
| tcgtcgttttgtcgttttgtcgtt | s2 | 732 |
| tcgtcgttttgtcgttttgtcgttb | o | 733 |
| tcgtcgttttgtcgttttgtcgttttgtcgtt | s | 734 |
| tcgtcgttttgtggttttgtggtt | s | 735 |
| tcgtcgtttttgtcgtttttgtcgtt | s | 736 |
| tcgtcgtttttttttttttttt | s | 737 |
| tcgtga | s | 738 |
| tcgtga | o | 739 |
| tcgtgg | s | 740 |
| tcgtzgttcccccccccccc | o | 741 |
| tcntcgtnttntcgtnttntcgtn | s | 742 |
| tctaaaaaccatctattcttaaccct | o | 743 |
| tctagcgttttagcgttcc | sos | 744 |
| tctatcccaggtggttcctgttag | o | 745 |
| tctatcgacgttcaagcaag | s | 746 |
| tctccatcctatggttttatcg | o | 747 |
| tctccatgatggttttatcg | | 748 |
| tctcccagcgagcgagcgccat | s | 749 |
| tctcccagcgagcgccat | s | 750 |
| tctcccagcgcgcgccat | s | 751 |
| tctcccagcgggcgcat | s | 752 |
| tctcccagcgtacgccat | s | 753 |
| tctcccagcgtcgccat | s | 754 |
| tctcccagcgtgcgccat | s | 755 |
| tctcccagcgtgcgccat | o | 756 |
| tctcccagcgtgcgccatat | sos | 757 |
| tctcccagcgtgcgccttttt | sos | 758 |

TABLE 4-continued

Exemplary Nucleic Acids.

| SEQUENCE | BACKBONE | SEQ ID NO: |
|---|---|---|
| tctcccagcgtgcgtgcgccat | s | 759 |
| tctcccagcgtgcgttatat | sos | 760 |
| tctcccagcgtgcgttttt | s | 761 |
| tctcccagcgttgcgccatat | sos | 762 |
| tctcccatcgtcgccat | s | 763 |
| tctcccgacgtgcgccat | s | 764 |
| tctcccgtcgtgcgccat | s | 765 |
| tctccctgcgtgcgccatat | sos | 766 |
| tctcctagcgtgcgccatat | sos | 767 |
| tctgacgtcatctgacgttggctgacgtct | o | 768 |
| tctgcgtgcgtgcgccatat | sos | 769 |
| tcttcgaa | o | 770 |
| tcttgcgatgctaaaggacgtcacattgcacaatcttaataaggt | o | 771 |
| tctttattagtgactcagcacttggca | o | 772 |
| tcztgacgttgaagt | o | 773 |
| tgaacgtt | o | 774 |
| tgcaatgtgacgtcctttagcat | o | 775 |
| tgcaggaagtccgggttttccccaaccccc | o | 776 |
| tgcatcagctct | s | 777 |
| tgcatcagctct | sos | 778 |
| tgcatcccccaggccaccat | s | 779 |
| tgcatgccgtacacagctct | sos | 780 |
| tgcatgccgtacacagctct | s | 781 |
| tgcatgccgtacacagctct | o | 782 |
| tgcatgccgtgcatccgtacacagctct | s | 783 |
| tgccaagtgctgagtcactaataaaga | o | 784 |
| tgcccaaagaggaaaatttgtttcatacag | o | 785 |
| tgcgctct | s | 786 |
| tgctagctgtgcctgtacct | | 787 |
| tgctagctgtgcctgtacct | s | 788 |
| tgctgcttcccccccccccc | o | 789 |
| tgctgcttcccccccccccc | s | 790 |
| tgctgcttttgtgcttttgtgctt | o | 791 |
| tgctgcttttgtgcttttgtgctt | s | 792 |
| tggaccttccat | | 793 |
| tggaccttctatgtcggtcc | | 794 |
| tggagggtgagggtggggccagagcgggtggggctgattggaa | o | 795 |
| tggaggtcccaccgagatcggag | o | 796 |
| tggttacggtctgtcccatg | | 797 |
| tgtatctctctgaaggact | o | 798 |
| tgtccagccgaggggaccat | | 799 |
| tgtcccatgttttagaagc | | 800 |
| tgtcgttgtcgtt | s | 801 |
| tgtcgttgtcgttgtcgttgtcgtt | s | 802 |
| tgtcgtttgtcgtttgtcgtt | s | 803 |
| ttaacggtggtagcggtattggtc | o | 804 |
| ttaacgtt | o | 805 |
| ttaagaccaataccgctaccaccg | o | 806 |
| ttaggacaaggtctagggtg | | 807 |
| ttagggttagggttagggtt | s2 | 808 |
| ttcagttgtcttgctgcttagctaa | o | 809 |
| ttcatgccttgcaaaatggcg | | 810 |
| ttccaatcagccccacccgctctggccccaccctcaccctcca | o | 811 |
| ttccatgctgttccggctgg | | 812 |
| ttccatgtcggtcctgat | sos | 813 |
| ttccgccgaatggcctcaggatggtac | | 814 |
| ttccgctttatctgagaaccatct | | 815 |
| ttcctctctgcaagagact | o | 816 |
| ttcgggcggactcctccatt | sos | 817 |
| ttcgggcggactcctccatt | o | 818 |
| ttcgtcgttttgtcgttttgtcgtt | s | 819 |
| ttctgtgtctgttgctggttccgctttatctgagaac | | 820 |
| ttgaaactgaggtgggac | | 821 |
| ttgccccatattttagaaac | | 822 |
| ttgggggggggtt | s | 823 |
| ttgtactctccatgatggtt | | 824 |
| tttaccttttataaacataactaaaacaaa | o | 825 |
| tttgaatcctcagcggtctccagtggc | o | 826 |
| tttgaattcaggactggtgaggttgag | o | 827 |
| tttgaattccgtgtacagaagcgagaagc | o | 828 |
| tttgagaacgctggaccttc | sos | 829 |
| tttgcggccgctagacttaacctgagagata | o | 830 |
| tttgggcccacgagagacagagacacttc | o | 831 |
| tttgggcccgcttctcgcttctgtacacg | o | 832 |
| ttttctagagaggtgcacaatgctctgg | o | 833 |

TABLE 4-continued

Exemplary Nucleic Acids.

| SEQUENCE | BACKBONE | SEQ ID NO: |
|---|---|---|
| tttttggggggggggttttt | o | 834 |
| ttttttttttttttf | o | 835 |
| ttttttttttttttf | so | 836 |
| ttttttttttttttttttt | s | 837 |
| tttttttttttttttttttttt | s | 838 |
| tttttttttttttttttttttt | o | 839 |
| ttttttttttttttttttttttt | s | 840 |
| ttttttttttttttttttttttttt | s | 841 |
| tttttttttttttttttttttttttttttt | s | 842 |
| tzaacgtt | o | 843 |
| tzgtcgttccccccccccc | o | 844 |
| tzgtcgttttgtcgttttgtcgtt | o | 845 |
| tzgtggttccccccccccc | o | 846 |
| tzgtzgttttgtzgttttgtzgtt | o | 847 |
| tzgtzgttttgtzgttttgtzgtt | s | 848 |

In Table 4 with respect to sequences the letter symbols aside from a, c, t, and g are defined as follows: "b" indicates a biotin moiety attached to that end of the oligonucleotide when it is single and is listed on the 5' or 3' end of oligonucleotide; "d" represents a, g, or t; "f" represents fluorescein isothiocyanate (FITC) moiety attached to the 5' or 3' end of oligonucleotide; "h" represents a, c, or t; "i" represents inosine; "n" represents any nucleotide; "z" represents 5-methylcytosine.

Also in Table 4 with respect to backbones the notations are defined as follows: "o" represents phosphodiester; "os" represents phosphorothioate and phosphodiester chimeric with phosphodiester on 5' end; "os2" represents phosphorodithioate and phosphodiester chimeric with phosphodiester on 5' end; "p-ethoxy" represents p-ethoxy backbone (see, e.g., U.S. Pat. No. 6,015,886); "po" represents phospholdiester; "s" represents phosphorothioate; "s2" represents phosphorodithioate; "s2o" represents phosphorodithioate and phosphodiester chimeric with phosphodiester on 3' end; "so" represents phosphorothioate and phosphodiester chimeric with phosphodiester on 3' end; and "sos" represents chimeric phosphorothioate/phosphodiester with phosphorothioate at the 5' and 3' ends.

The nucleic acids are delivered in effective amounts. The term "effective amount" of a immunostimulatory nucleic acid refers to the amount necessary or sufficient to realize a desired biologic effect. For example, an effective amount of an immunostimulatory nucleic acid could be that amount necessary to cause activation of the immune system. According to some aspects of the invention, an effective amount is that amount of an immunostimulatory nucleic acid and that amount of an antibody, which when combined or co-administered, results in the prevention or the treatment of the cancer. In some embodiments a synergistic effect is observed. A synergistic amount is that amount which produces an anti-cancer response that is greater than the sum of the individual effects of either the immunostimulatory nucleic acid and the antibody alone. For example, a synergistic combination of an immunostimulatory nucleic acid and an antibody provides a biological effect which is greater than the combined biological effect which could have been achieved using each of the components (i.e., the nucleic acid and the antibody) separately. The biological effect may be the amelioration and or absolute elimination of symptoms resulting from the cancer. In another embodiment, the biological effect is the complete abrogation of the cancer, as evidenced for example, by the absence of a tumor or a biopsy or blood smear which is free of cancer cells.

The effective amount of immunostimulatory nucleic acid necessary to treat a cancer or in the reduction of the risk of developing a cancer may vary depending upon the sequence of the immunostimulatory nucleic acid, the backbone constituents of the nucleic acid, and the mode of delivery of the nucleic acid. The effective amount for any particular application can also vary depending on such factors as the cancer being treated, the particular immunostimulatory nucleic acid being administered (e.g., the nature, number or location of immunostimulatory motifs in the nucleic acid), the size of the subject, or the severity of the disease or condition. One of ordinary skill in the art can empirically determine the effective amount of a particular immunostimulatory nucleic acid and antibody combination without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Therapeutic doses of cancer therapies are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer. Therapeutic dosages of immunostimulatory nucleic acids have also been described in the art and methods for identifying therapeutic dosages in subjects are described in more detail herein.

Subject doses of the compounds described herein typically range from about 0.1 µg to mg per administration, which depending on the application could be given daily, weekly, or monthly and any other amount of time therebetween. More typically mucosal or local doses range from about 10 µg to 5 mg per administration, and most typically from about 100 µg to 1 mg, with 2-4 administrations being spaced hours, days or weeks apart. More typically, immune stimulant doses range from 1 µg to 10 mg per administration, and most typically 10 µg to 1 mg, with daily or weekly administrations. Subject doses of the compounds described herein for parenteral delivery, wherein the compounds are delivered without another therapeutic agent are typically 5 to 10,000 times higher than the effective mucosal dose or for immune stimulant applications, and more typically 10 to 1,000 times higher, and most typically 20 to 100 times higher. More typically parenteral doses for these purposes range from about 10 μg to 5 mg per administration, and most typically from about 100 μg to 1 mg, with 2-4 administrations being spaced hours, days or weeks apart. In some embodiments, however, parenteral doses for these purposes may be used in a range of 5 to 10,000 times higher than the typical doses described above.

For any compound described herein the therapeutically effective amount can be initially determined from animal models, e.g., the animal models described herein. A therapeutically effective dose can also be determined from human data for CpG nucleic acids which have been tested in humans (human clinical trials have been initiated and the results publicly disseminated) and for compounds which are known to exhibit similar pharmacological activities. Higher doses may be required for parenteral administration, as described above. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the nucleic acid can be administered to a subject by any mode that delivers the nucleic acid to a subject. "Administering" the pharmaceutical composition of the present invention may be accomplished by any means known to the skilled artisan. Some routes of administration include but are not limited to oral, intranasal, intratracheal, inhalation, ocular, vaginal, rectal, parenteral (e.g., intramuscular, intradermal, intravenous or subcutaneous injection) and direct injection.

For oral administration, the compounds (i.e., nucleic acids and antibodies) can be delivered alone without any pharmaceutical carriers or formulated readily by combining the active compound(s) with pharmaceutically acceptable carriers well known in the art. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions.

Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray, from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions may also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer R, *Science* 249:1527-33 (1990), which is incorporated herein by reference.

The nucleic acids and/or antibodies may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The nucleic acids or other therapeutics useful in the invention may be delivered in mixtures with additional antibodies. A mixture may consist of several antibodies in addition to the nucleic acid.

A variety of administration routes are available. The particular mode selected will depend, of course, upon the particular nucleic acids or antibodies selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix =such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The nucleic acid may be directly administered to the subject or may be administered in conjunction with a pharmaceutically acceptable carrier or a delivery vehicle. The nucleic acid and optionally other therapeutic agents may be administered alone (e.g., in saline or buffer) or using any delivery vehicles known in the art. One type of delivery vehicle is referred to herein as a nucleic acid delivery complex. A "nucleic acid delivery complex" shall mean a nucleic acid molecule associated with (e.g., ionically or covalently bound to; or encapsulated within) a targeting means (e.g., a molecule that results in higher affinity binding to target cell (e.g., dendritic cell surfaces and/or increased cellular uptake by target cells). Examples of nucleic acid delivery complexes include nucleic acids associated with: a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to reduce significant uncoupling prior to internalization by the target cell. However, the complex may be cleavable under appropriate conditions within the cell so that the nucleic acid may be released in a functional form.

The nucleic acids may be delivered by non-invasive methods as described above. Non-invasive delivery of compounds is desirable for treatment of children, elderly, animals, and even adults and also to avoid the risk of needle-stick injury. Delivery vehicles for delivering compounds to mucosal surfaces have been described and include but are not limited to: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et al., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus* Calmette -Guérin, *Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); Polymers (e.g., carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998).

The invention also includes kits. The kits generally include a package with a plurality of containers housing active agents and instructions for carrying out the methods of the invention. The active agents include but are not limited to immunostimulatory nucleic acids, antibodies such as antibodies specific for a cell surface antigen, and anti-cancer therapies.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Introduction:

Extensive cross-talk exists between healthy B cells and T cells. There is evidence that malignant B cells also communicate with T cells. However, malignant cells appear to differ from their normal counterparts in a number of ways, including a decreased tendency to undergo apoptosis in response to normal signals, altered expression of a variety of surface markers, and altered ability to function as effective antigen presenting cells. Lagneaux L et al., *Blood* 91:2387-96 (1998); Gordon J et al., *Leukemia* 7 Suppl 2:S5-9 (1993); Gordon J et al., *Adv Exp Med Biol* 406:139-44 (1996); Chaperot L et al., *Exp Hematol* 27:479-88 (1999). Immunotherapeutic approaches have recently become part of our therapy of some subtypes of B-cell malignancy. Improved immunotherapy of B-cell malignancy will need to be designed based on the growing understanding of the cellular immunology of this disease. Schultze J L et al., *J Mol Med* 77:322-32 (1999).

A variety of cellular receptors and antigens are involved in growth, differentiation and apoptosis of B-cell malignancies. Antibodies or ligands against a variety of antigens can cause growth inhibition or even apoptosis including CD20, surface immunoglobulins, MHC II, CD80, CD86 and CD40. Maloney D G, *Semin Oncol* 26:74-8 (1999); McLaughlin P et al., *Semin Oncol* 26:79-87 (1999); Shan D et al., *Blood* 91:1644-52 (1998); Coiffier B et al., *Blood* 92:1927-32 (1998); McLaughlin P et al., *Oncology (Huntingt)* 12:1763-70, 1775-7 (1998); Tutt A L et al., *J Immunol* 161:3176-85 (1998); Funakoshi S et al., *Blood* 83:2787-94 (1994); Mayumi M et al., *J Allergy Clin Immunol* 98:S238-47 (1996); Higaki Y et al., *Immunol Cell Biol* 72:205-14 (1994); Elsasser D et al., *Blood* 87:3803-12 (1996); Link B K et al., *Blood* 81:3343-9 (1993); Link B K et al., *Int J Cancer* 77:251-6 (1998). The relative contribution of antibody dependent cellular cytotoxicity (ADCC) versus trans-membrane signaling mediated by anti-B cell antibodies remains unclear. In the present study, we examined how CpG-DNA impacts on the phenotype, apoptosis and proliferation of different types of B-cell malignancy including follicular B-cell lymphoma and B-CLL.

Materials and Methods:

Cell culture: Fresh lymph node samples were obtained from the operating suite and were minced with a scalpel under aseptic conditions. The resulting suspension was passed sequentially through a sterilized sieve-tissue grinder containing a nylon mesh screen, a 150 µm mesh screen and a 60 µm mesh screen. Alternatively, mononuclear cells were obtained from peripheral blood or pleural fluid as described. Hartmann G et al., *J Pharmacol Exp Ther* 285:920-8 (1998). Red blood cells were removed by resuspending the cells in 5 ml ACK lysis buffer according to standard procedures. Cells were frozen slowly and stored in liquid nitrogen. For analysis, cells were thawed and resuspended in 10% (v/v) heat-inactivated (56° C., 1 h) FCS (HyClone, Logan, U T), 1.5 mM L-glutamine (all from Gibco BRL, Grand Island, N.Y.) and incubated on a 96-well-plate ($1 \times 10^6$ cells/ml) in the presence of ODN as indicated below. Not all assays were performed for all samples because of the limited number of cells available for some samples.

Oligonucleotides: Nuclease-resistant phosphorothioate-modified oligodeoxynucleotide (ODN) were purchased from Operon Technologies (Alameda, Calif.) and Hybridon Specialty Products (Milford, Mass.). Sequences were as follows: CpG ODN 2006: 5'-TCGTCGTTTTGTCGTTTTGTCGTT-3' (SEQ ID NO: 729), and control ODN 2017: 5'-CCCCCCCCCCCCCCCCCCCC-3' (SEQ ID NO: 168). ODN was diluted in TE (10 mM Tris-HCl, 1 mM EDTA, pH 8) using pyrogen-free reagents. ODN was added at a final concentration of 5 µg/ml.

Flow cytometry: Cells were washed and resuspended in ice-cold PBS or Annexin V binding buffer (10 mM HEPES/NaOH, 140 mM NaCl, 2.5 mM $CaCl_2$, pH 7.4). Murine or human serum was added (final concentration 1%) to block non-specific binding of antibodies. Surface antigen staining was as described. Hartmann G et al., *J Pharmacol Exp Ther* 285:920-8 (1998). In brief, $1 \times 10^5$ cells per sample were stained with CyChrome-labeled anti-CD19 and FITC- or PE-labeled antibodies as indicated for 20 min on ice. They were then washed and analyzed by flow cytometry. Monoclonal antibodies to CD40 (5C3), CD69 (FN50), CD80 (L307.4), CD86 (IT2.2), CD54 (HA58), MHC I (G46-2.6) and MHC II (TU39) as well as isotype controls (IgG1, MOPC-21 and IgG2a, G155-178) were purchased from PharMingen, San Diego, Calif. FITC-labeled polyclonal anti-human Ig was purchased from Southern Biotech, Birmingham, Ala. 1D10, a monoclonal humanized antibody directed against a variant of HLA-DR was produced in our laboratory as described earlier. Link B K et al., *Blood* 81:3343-9 (1993). C2B8, a monoclonal humanized anti-CD20 antibody, was purchased from IDEC Pharmaceuticals, San Diego, Calif. 1D10 and C2B8 were labeled with FITC according to standard protocols. The analysis gate was set on viable cells identified according to FSC/SSC characteristics and Annexin V staining (>97% viable cells within analysis gate). Spectral overlap was corrected by appropriate compensation. Flow cytometric data from 1×10⁴ cells per sample were acquired on a FACScan (Beckton Dickinson Immunocytometry Systems, San Jose, Calif.). Data were analyzed using the computer program FlowJo (version 2.5.1, Tree Star, Inc., Stanford, Calif.).

CFSE staining: CFSE 5-(and 6-) carboxyfluorescein diacetate succinimidyl ester, Molecular Probes, USA, is a fluorescein-derived intracellular fluorescent label which is divided equally between daughter cells upon cell division. Staining of cells with CFSE allows both quantification and immunophenotyping of proliferating cells in a mixed cell suspension. Interference between oligonucleotide degradation products and thymidine uptake (standard proliferation assay) is avoided by using this method. The technique has described in detail previously. Lyons A B et al., *J Immunol Methods* 171:131-7 (1994). Briefly, cells were washed twice in PBS, resuspended in PBS (1×10⁷ cells/ml) containing CFSE at a final concentration of 1 µM, and incubated at 37° C. for 10 minutes. Cells were washed three times with PBS.

TUNEL assay: A two-color DNA strand break labeling assay, based on a modification of the assay described by Li et al. (Li X et al., *ExpCell Res* 222:28-37 (1996)) was used to assess B-cell proliferation in response to CpG ODN. This assay involved terminal transferase-mediated dUTP nick end labeling (TUNEL) before and after induction of DNA strand breaks in BrdU-labeled cells. Briefly, cells were cultured for 3 days with and without ODN. They were then incubated for 16 hours in 10 µM BrdU and placed onto slides by cytospin. Cells were then in 1% paraformaldehyde in PBS for 15 minutes followed by 20 minutes in 70% ethanol. DNA cleavage indicative of apoptosis cells was detected by labeling the 3'-DNA end of nicked strands with FITC-ddUTP (Boehringer-Mannheim). The use of dideoxy-dUTP prevented further elongation of the 3'-ends in subsequent steps. Slides were then placed face-down on a 2 mm support at both ends on a UV transilluminator and exposed for 5 minutes. The new DNA strand breaks induced by photolysis at sites of BrdU incorporation (i.e., proliferating cells) were detected by a second TUNEL labeling using tetramethylrhodamine-dUTP (TMR-dUTP, Boehringer-Mannheim). Both TUNEL staining steps included incubating slides in 50 µl of TdT mix (34 µl distilled water, 10 µl of 5×TdT buffer, 5 µl of 25 mM cobalt chloride, 12.5 units terminal transferase and 0.5 nmol fluorochrome-conjugated-dUTP) (Boehringer-Mannheim) under a coverslip for one hour at 37° C. in a humidified chamber. The slides were then washed in 5 quick changes of distilled water followed by 3 changes of 2×SSC containing 30% formamide for 5 minutes each at room temperature. After the second TUNEL labeling step, cells were counterstained for CD19, and also stained with Wright solution for blood cell differentiation and mounted in Vectashield media containing DAPI counterstain (Vector Laboratories, Burlingame, Calif.). The morphology and staining of cells were assessed using both visible light and fluorescence microscopy. Apoptotic cells were identified by green fluorescence (FITC label), and proliferating cells by red fluorescence (TMR label). The percentage of apoptotic and proliferating cells was determined by counting at least 200 cells per sample by three observers blinded to whether cells were treated with ODN. Mean and standard error were determined for each sample based on these three readings.

Example 1

Immunostimulatory Nucleic Acids Induce Morphological and Phenotypic Changes in Malignant B Cells Our prior studies demonstrated that activation of naive human B cells by CpG ODN results in increased cell size (FSC) and granularity (SSC). Hartmann G et al., *J Immunol* 164:944-53 (2000). We therefore first determined whether such changes also occur in malignant B cells. Primary malignant B cells were obtained from lymph node biopsies, peripheral blood, or pleural fluid of patients with various types of B-cell malignancy. In addition, cells from the lymph node of a patient with benign reactive follicular hyperplasia were studied. Nine samples in total were evaluated (see Table 5). Cells were incubated for 72 hours in media containing CpG ODN 2006 (5 µg/ml) or control ODN 2017. FSC and SSC were examined with gating on CD19+ viable cells (FIG. 1). Varying degrees of change in FSC and SSC were noted in response to CpG ODN 2006 when compared to control ODN 2017 or medium alone. Comparable changes were not found in the cells from the patient with benign reactive follicular hyperplasia.

FIG. 1 depicts the morphologic changes of marginal zone lymphoma cells upon CpG ODN stimulation. Malignant B cells from a patient with marginal zone lymphoma were stimulated with 5 µg/ml of no ODN (A and D), control ODN (B and E) or CpG ODN (C and F) for 72 hours and analyzed by flow cytometry. A, B, and C illustrate FSC (x-axis) vs. SSC (y-axis). D, E and F illustrate CD19 expression (x-axis) against FSC (y-axis), allowing for separation of B cells from other leukocyte subpopulations. Upon stimulation with CpG ODN, B cells shifted up and to the right, indicating an increase in granularity and size. No changes could be detected without stimulation or on stimulation with the non-CpG ODN.

Expression of CD20, CD40, CD69, CD80, CD86, surface Ig, CD54, MHC I, MHC II, and an HLA-DR variant antigen (moAb 1D10) were examined on viable CD19+ cells after incubation of cells with CpG ODN for 72 hours. Each of these markers was upregulated to varying extents in response to the CpG ODN 2006 compared to the control ODN 2017 (FIG. 2, FIG. 3).

Figure 2:
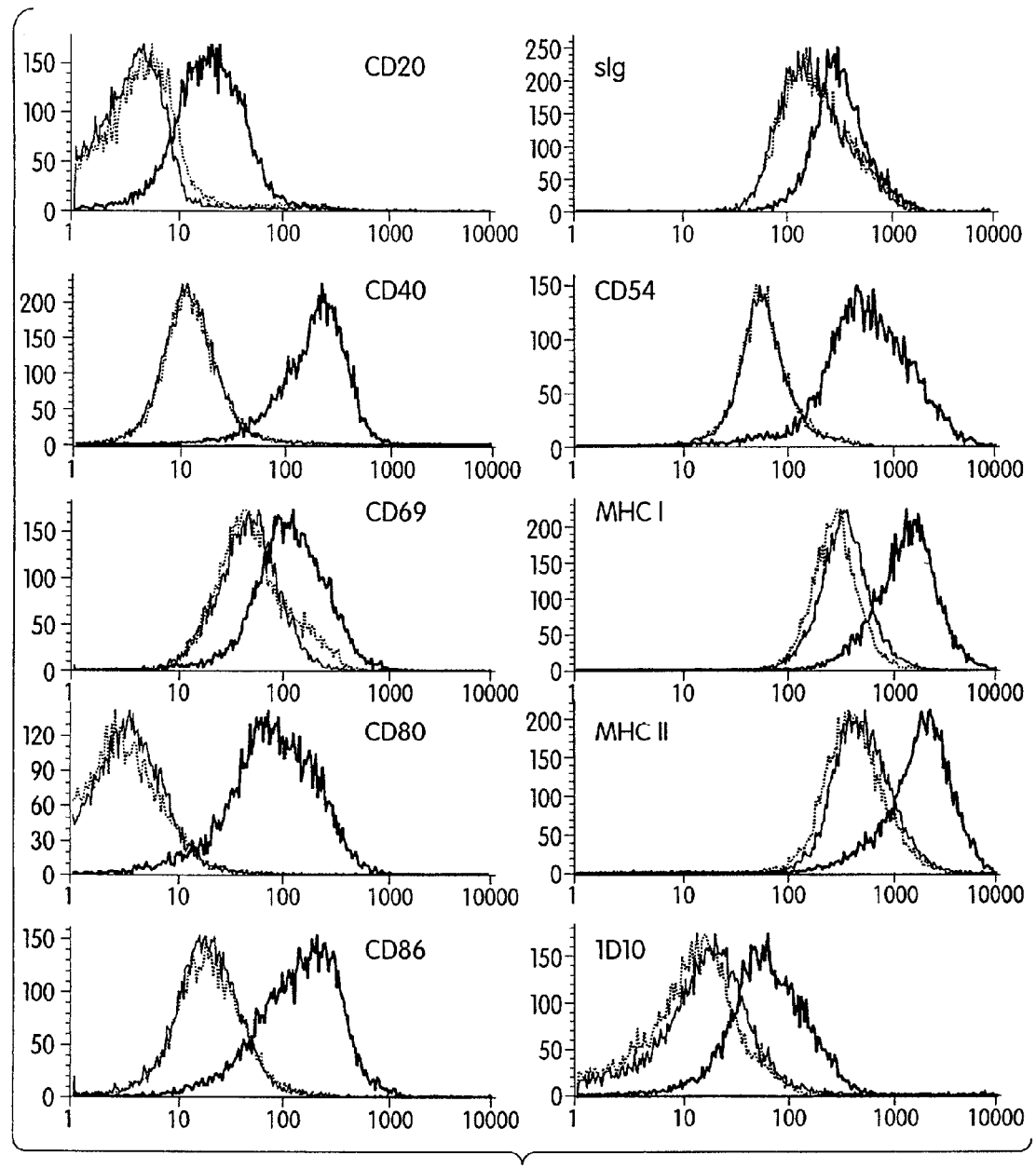
FIG. 2 depicts data from flow cytometry which demonstrates the change in expression of surface antigens on marginal zone lymphoma cells upon CpG oligodoeynucleotide (ODN) treatment. Flow cytometric analysis of surface antigen expression on malignant B cells from a patient with marginal zone lymphoma was performed using either CpG or non-CpG oligonucleotide. Thin curves indicate incubation with medium alone, dotted curves indicate incubation with control oligonucleotide, and bold curves indicate incubation with CpG oligonucleotide.

FIG. 2 depicts the expression of surface antigens on marginal zone lymphoma cells upon CpG ODN treatment. Flow cytometric analysis of surface antigen expression on malignant B cells from a patient with marginal zone lymphoma was performed 72 hours after stimulation with 5 µg/ml of either CpG ODN or non-CpG ODN. On stimulation with CpG ODN, median fluorescence intensity for all markers tested shifted to the right, indicating an increase in surface expression. Thin curves indicate incubation with medium alone, dotted curves incubation with control ODN, and bold curves incubation with CpG ODN.

Figure 3:
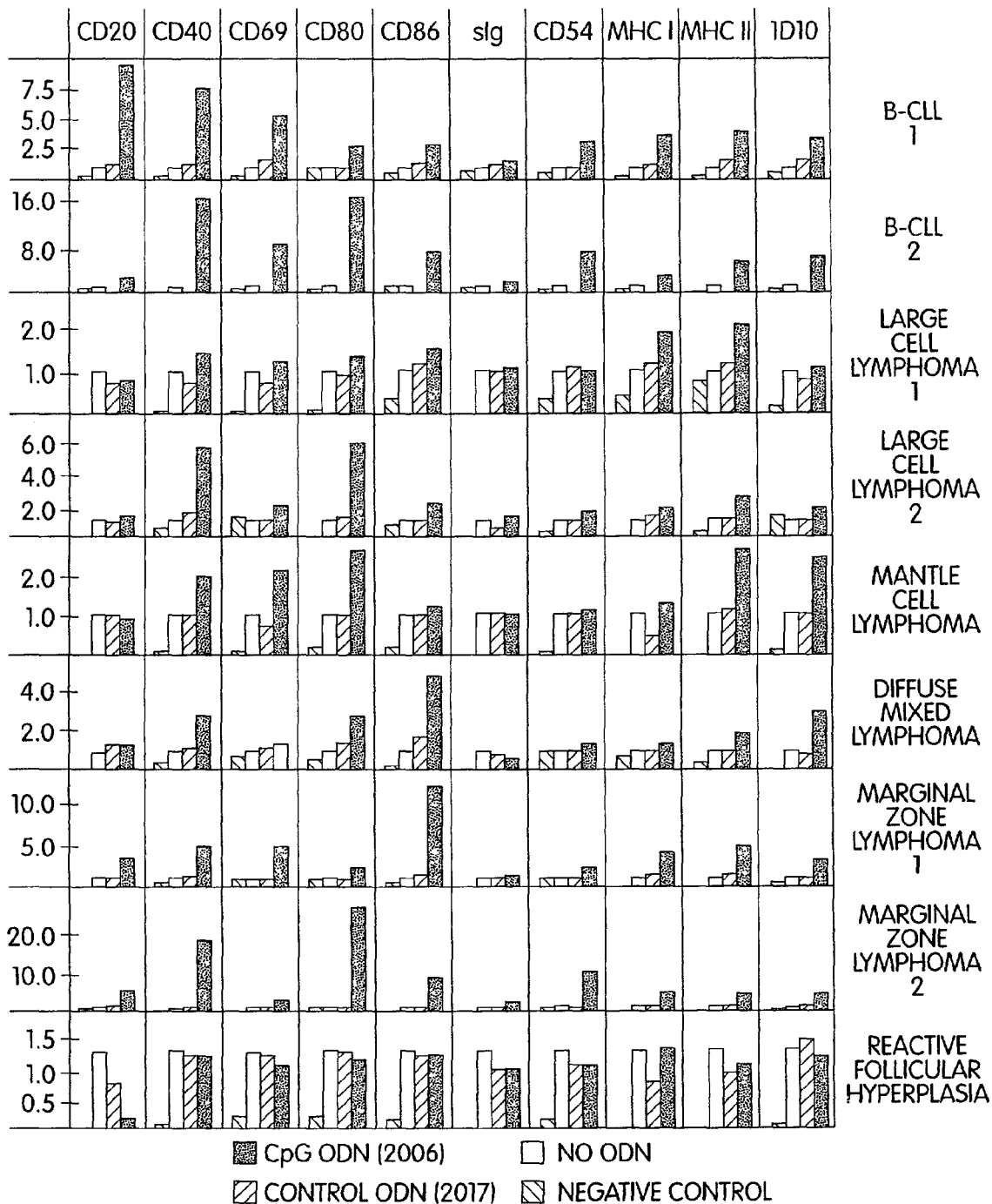
FIG. 3 is a set of bar graphs depicting changes in expression of surface antigens on primary cells representing different B-cell malignancies and cells of a benign follicular hyperplasia upon treatment with, from left to right in each panel: negative control, no oligonucleotide, control oligonucleotide (ODN 2017, SEQ ID NO: 168), or CpG oligonucleotide (ODN 2006, SEQ ID NO: 729). Each panel represents one experiment.

FIG. 3 depicts the expression of surface antigens on primary cells representing different B-cell malignancies and cells of a benign follicular hyperplasia upon CpG ODN treatment. Cells from lymph node biopsies, peripheral blood or pleural fluid from patients with different B-cell malignancies were incubated for 72 hours with either media alone, control ODN or CpG ODN. Each panel represents one experiment.

Figure 4:
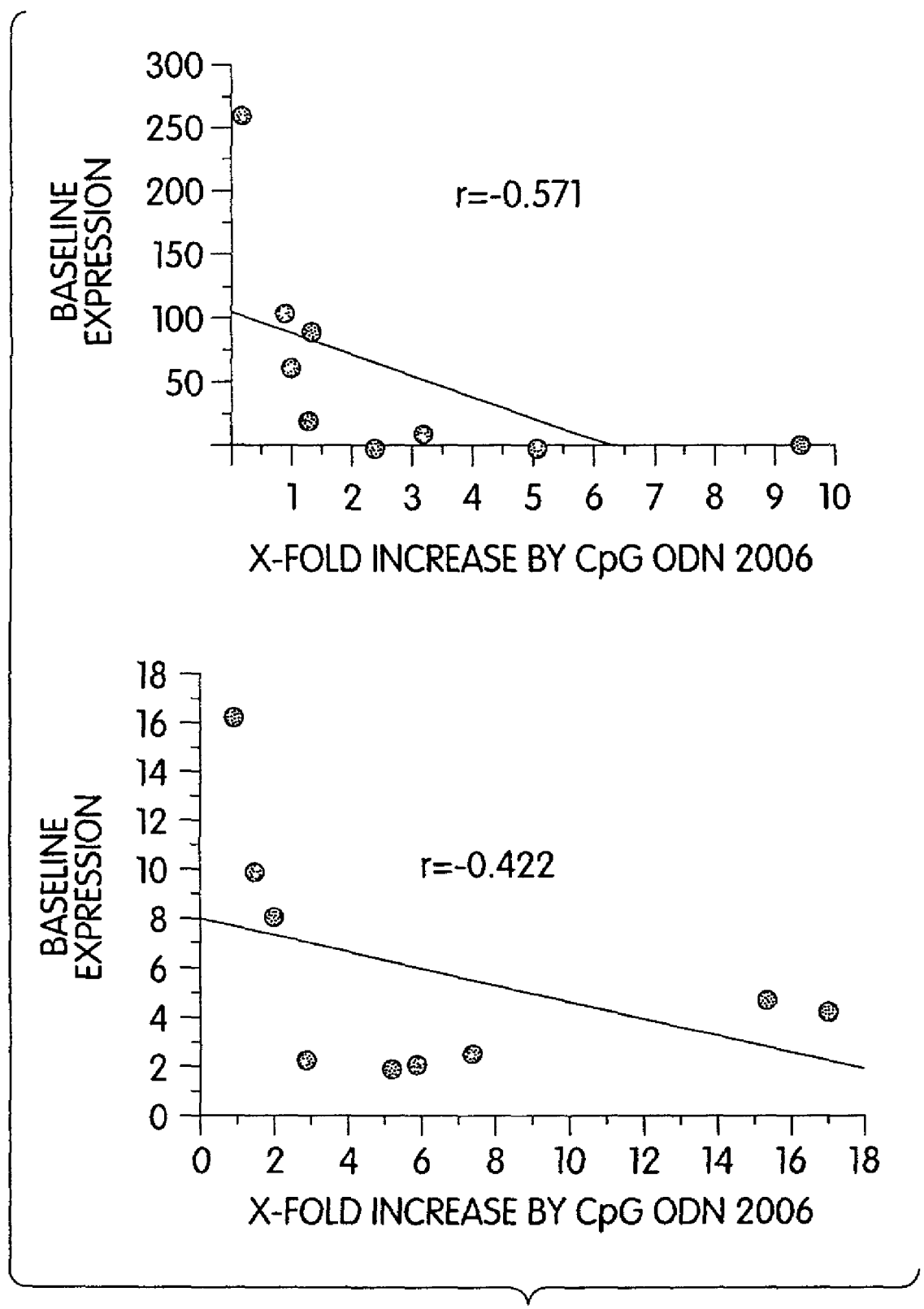
FIG. 4 is a set of graphs depicting the observation that the effect of CpG oligonucleotide on CD20 (top) and CD40 (bottom) is dependent on the baseline level of expression of CD20 and CD40. Cells from lymph node biopsies, peripheral blood or pleural fluid from patients with different B-cell malignancies were incubated with or without CpG oligonucleotide, and expression of CD20 and CD40 was measured by flow cytometry.

CD20 was expressed to varying degrees in all samples tested. As is well known, baseline CD20 expression was lower in the B-CLL samples when compared to the B-cell malignancies of other histologies. CpG-ODN 2006 but not the control ODN 2017 increased CD20 expression in both B-CLLs and both marginal zone lymphomas. No or only little upregulation was seen in the other lymphoma samples. Non-malignant CD19+ cells derived from the reactive follicular hyperplasia decreased CD20 expression in response to CpG (FIG. 3). This data demonstrated a reverse correlation between the baseline expression of CD20 and CD40, and expression of these markers after incubation with CpG ODN; thus the lower the baseline level of CD20 and CD40, the higher was the responsiveness to CpG ODN (r: −0.6; −0.4) (FIG. 4). This correlation was less clear for the other markers. CD19+ cells derived from the reactive follicular hyperplasia showed high baseline expression of activation markers which was not further upregulated by CpG.

FIG. 4 shows the CpG ODN effect on CD20 and CD40 is dependent on the baseline level of expression. Cells from lymph node biopsies, peripheral blood or pleural fluid from patients with different B-cell malignancies (see Table 5) were incubated with or without CpG ODN for 72 hours. Expression of CD20 and CD40 was measured by flow cytometry. Baseline expression of CD20 and CD40 with medium alone was compared to the expression of CD20 and CD40 in the presence of CpG ODN. The coefficients of correlation are indicated.

TABLE 5

Percentage Of CD19+ Cells In Samples Tested.

| Sample Number | Histology | Source | % CD19+ Cells |
| --- | --- | --- | --- |
| 1 | Chronic Lymphocytic Leukemia 1 | Peripheral Blood | >98% |
| 2 | Chronic Lymphocytic Leukemia 2 | Peripheral Blood | 70% |
| 3 | Large Cell Lymphoma 1 | Pleural Fluid | 55% |
| 4 | Large Cell Lymphoma 2 | Lymph Node | 75% |
| 5 | Mantle Cell Lymphoma | Lymph Node | 98% |
| 6 | Diffuse Mixed Small and Large Cell Lymphoma | Lymph Node | 50% |
| 7 | Marginal Zone Lymphoma 1 | Lymph Node | 80% |
| 8 | Marginal Zone Lymphoma 2 | Peripheral Blood | >94% |
| 9 | Reactive Follicular Hyperplasia | Lymph Node | 35% |

Example 2

Figure 5:
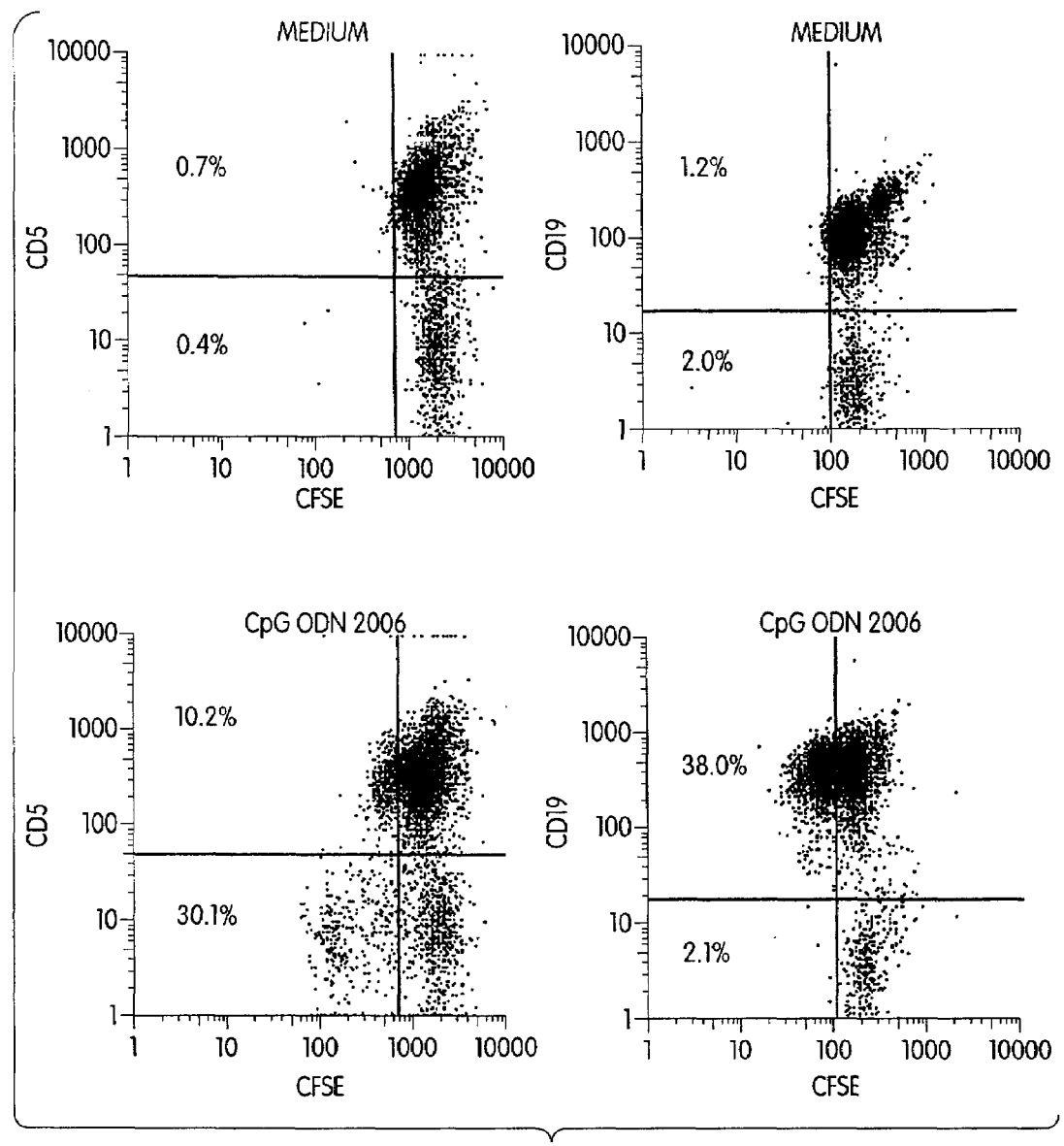
FIG. 5 depicts data from flow cytometry which demonstrates the effect of CpG oligonucleotide-induced proliferation of malignant and normal B cells. Peripheral blood mononuclear cells from patients with B-CLL (left) or marginal zone lymphoma with circulating malignant cells (right), were incubated with CpG oligonucleotide (bottom) or medium alone (top) and evaluated by two-color flow cytometry. CFSE fluorescence (x-axis) and expression of CD5 (B-CLL) or CD19 (marginal zone lymphoma) (y-axis) were evaluated.

Immunostimulatory Nucleic Acids Induce Proliferation and Apoptosis of Malignant B Cells CpG induces a strong proliferative response of primary human B cells. Hartmann G et. al., *J Immunol* 164:944-53 (2000). Two techniques were used to assess whether CpG ODN is capable of inducing proliferation of B-CLL cells. For select samples, cells were stained with CFSE and incubated for four days. Proliferation of cells is indicated by a loss of CFSE stain with every cell division. In B-CLL, CD5 can be used to identify malignant B cells among CD19+ cells. Proliferation of malignant B cells (CD5+ and CD19+) was lower than proliferation of normal B cells (CD5− and CD19+) (FIG. 5). For the marginal zone lymphoma, CpG ODN 2006 induced proliferation of the CD19+ cell population (FIG. 5).

FIG. 5 shows a comparison of CpG ODN induced proliferation of malignant and normal B cells. Peripheral blood mononuclear cells from two patients, one with B-CLL and one with marginal zone lymphoma with circulating malignant cells, were incubated for 72 hours with CpG ODN or medium alone and evaluated by two-color flow cytometry. CFSE fluorescence (x-axis) and expression of CD5 (CLL) or CD19 (marginal zone lymphoma) (y-axis) were evaluated. In CLL, CpG ODN enhanced proliferation of both CD5+ and the CD5− cells. However the relative number of proliferating cells and the number of divisions is lower in the CD5− subset than in the CD5+ subset. In marginal zone lymphoma CpG ODN enhanced proliferation in the CD19+ cell subset.

No consistent pattern was apparent related to determining whether CpG ODN altered the percent of dead cells as determined by morphological criteria (see Table 6).

TABLE 6

Percent Apoptotic Cells Based On Morphologic Criteria.

| Sample Number | Histology | Media | CpG ODN 2006 |
| --- | --- | --- | --- |
| 1 | Chronic Lymphocytic Leukemia 1 | 25.9 | 21.5 |
| 2 | Chronic Lymphocytic Leukemia 2 | 32.6 | 45.3 |
| 3 | Large Cell Lymphoma 1 | 33.9 | 26.2 |
| 4 | Large Cell Lymphoma 2 | 16.0 | 9.8 |
| 5 | Mantle Cell Lymphoma | 55.1 | 60.0 |
| 6 | Diffuse Mixed Small and Large Cell Lymphoma | 27.6 | 26.6 |
| 7 | Marginal Zone Lymphoma 1 | 32.9 | 32.8 |
| 8 | Marginal Zone Lymphoma 2 | 38.8 | 56.0 |
| 9 | Reactive Follicular Hyperplasia | 8.6 | 18.0 |

A TUNEL assay was utilized to assess the effect of CpG ODN on both proliferation and apoptosis. The results are shown in Table 7.

TABLE 7

Apoptosis And Proliferation As Determined By TUNEL.

| | Baseline | | CpG ODN | | Control ODN | |
| --- | --- | --- | --- | --- | --- | --- |
| Sample | Apop | Prolif | Apop | Prolif | Apop | Prolif |
| 1663141 | 15 | 8 | 11 | 10 | 12 | 5 |
| 12142812 | 3 | <1 | 1 | 10 | 2 | 12 |
| 12141811 | <1 | <1 | <1 | 11 | ? | ? |

Example 3

Figure 6:
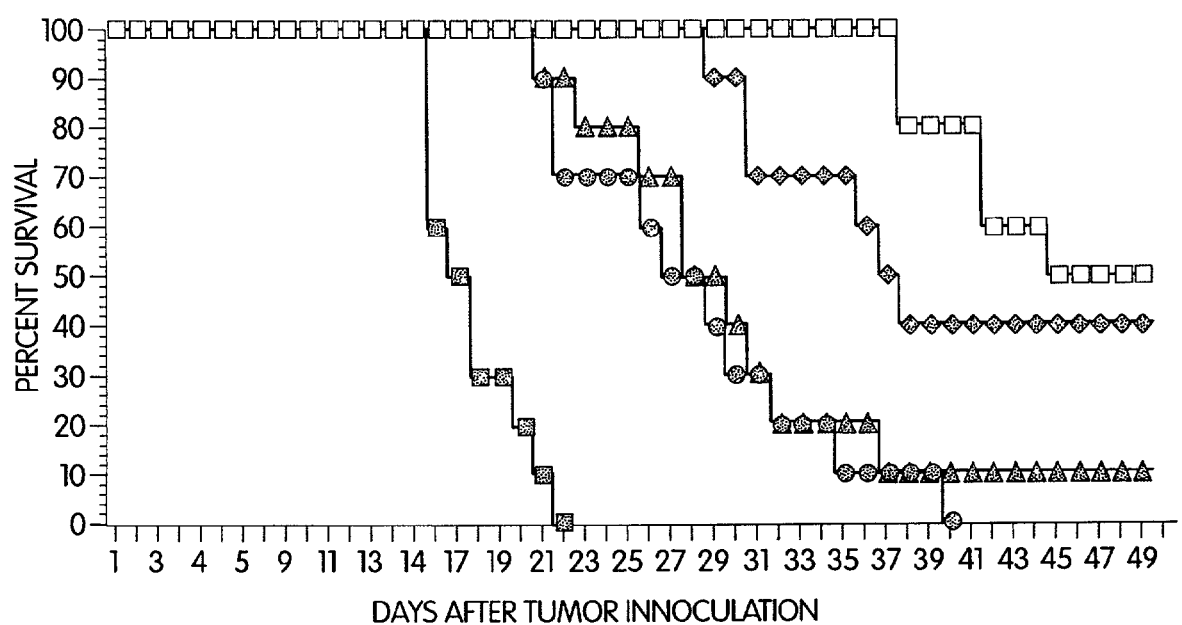
FIG. 6 is a graph depicting the survival of mice injected on Day 0 with tumor cells in response to CpG simulation in combination with murine IgG2a and murine IgG1 anti-tumor antibodies. Treatments are shown as filled squares, untreated controls; filled circles, murine IgG1; filled triangles, murine IgG1 plus CpG; filled diamonds, murine IgG2a; and open squares, murine IgG2a plus CpG.

CpG ODN Enhance the Therapeutic Effect of Murine IgG2a (Which Relates to Human IgG1) but not Murine IgG1 (Which Relates to Human IgG2) Anti-tumor Antibody CpG ODN when combined with antibody of murine subtype IgG2a dramatically promotes survival in mice having tumors. Mice were injected i.p. with 5000 T3C cells on day 0. They were then given 100 μg anti-idiotype monoclonal antibody as either IgG1 (MS5A10) or IgG2a (MS11G6) on days 5, 7, and 10. In this model, the target antigen is the idiotype expressed by the lymphoma cells. Therefore, the anti-tumor antibodies are also "anti-idiotype." These antibodies (MS5A10 and MS11G6) are simultaneously both anti-tumor antibodies and anti-idiotype antibodies. Twenty micrograms of CpG ODN 1826 (5' TCCATGACGTTCCTGACGTT 3'; SEQ ID NO: 560) was given at the same time. Results are shown in FIG. 6. Untreated controls had a median survival time (MST) of 17 days after inoculation with tumor. Mice treated with murine IgG1 antibody plus CpG ODN had survival that was similar to those treated with murine IgG1 antibody alone (MST 28 days and 27 days, respectively). In contrast, mice treated with murine IgG2a plus CpG ODN had survival that was significantly improved when compared to mice treated with murine IgG2a alone (MST 45 days and 37 days, respectively).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for treating a subject having a B-cell malignancy resistant to therapy with an antibody specific for a surface antigen selected from CD19, CD20, and CD22, wherein cells of the malignancy have low or no baseline expression of the surface antigen, the method comprising:
   administering to the subject the immunostimulatory CpG oligonucleotide ODN 2006 (SEQ ID NO:729) comprising a backbone modification and an unmethylated C, in an effective amount to upregulate expression of the surface antigen by the cells; and
   administering to the subject an antibody specific for the upregulated surface antigen, in an effective amount to treat the subject.

2. A method for treating a subject having a B-cell malignancy, wherein cells of the B-cell malignancy have low or no baseline expression of CD20, the method comprising:
   administering to the subject the immunostimulatory CpG oligonucleotide ODN 2006 (SEQ ID NO:729) comprising a backbone modification and an unmethylated C, in an effective amount to upregulate expression of CD20 by the cells; and
   administering to the subject an antibody specific for CD20, in an effective amount to treat the subject.

3. A method for treating a subject having a marginal zone lymphoma or B-cell chronic lymphocytic leukemia, wherein cells of the lymphoma or leukemia have low or no baseline expression of an antigen selected from CD19 and CD22, the method comprising:
   administering to the subject the immunostimulatory CpG oligonucleotide ODN 2006 (SEQ ID NO:729) comprising a backbone modification and an unmethylated C, in an effective amount to upregulate expression of the antigen by the cells of the lymphoma or leukemia; and
   administering to the subject an antibody specific for the upregulated antigen, in an effective amount to treat the subject.

4. A method for treating a subject having a B-cell malignancy, wherein cells of the malignancy upregulate expression of a surface antigen selected from CD19, CD20, and CD22, in response to immunostimulatory CpG oligonucleotide, the method comprising:
   isolating malignant B cells from the subject;
   identifying a surface antigen selected from CD19, CD20, and CD22, the expression of which can be upregulated in response to immunostimulatory CpG oligonucleotide, wherein the surface antigen is expressed by the malignant B cells in an amount lower than that of normal B cells;
   administering to the subject the immunostimulatory CpG oligonucleotide ODN 2006 (SEQ ID NO:729) comprising a backbone modification and an unmethylated C, in an effective amount to upregulate expression of the surface antigen by the cells; and
   administering to the subject an antibody specific for the upregulated surface antigen, in an amount effective to treat the subject.

* * * * *

```
                        SEQUENCE LISTING

<160> NUMBER OF SEQ ID NOS: 848

<210> SEQ ID NO 1
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 1 aaaaaa                                                                     6

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 2
aaaaaaaaaa aaaaaaaaaa                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 3
aaaaaccccc cccccaaaaa                                                     20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: Chimeric phosphorothioate/phosphodiester
      backbone with phosphorothioate at 5' and 3' ends

<400> SEQUENCE: 4
aaaacatgac gttcaaaaaa                                                     20
```

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 5
aaaacatgac gttcaaaaaa                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 6
aaaacatgac gttcggggggg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 7
aaaacatgac gttcggggggg                                                   20

<210> SEQ ID NO 8
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 8 aaaacgtt                                                                  8

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 9
aaaatcaacg ttgaaaaaaa                                                    20

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 10
aaaatctgtg cttttaaaaa a                                                    21

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 11
aaaattgacg ttttaaaaaa                                                      20

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 12
aaacattctg ggggaatttt aagaagtaaa cat                                       33

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 13
aaacattctg ggggaatttt aagaagttcc tccctcccc                                 39

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 14
aaacattctg ggggaatttt gtctagtaaa cat                                       33

<210> SEQ ID NO 15
<211> LENGTH: 17

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 15
aacgctcgac cttcgat                                              17

<210> SEQ ID NO 16
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 16
aacgctggac cttccat                                              17

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 17
aacgctggac cttccatgtc                                           20

<210> SEQ ID NO 18
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 18 aacgtt                                                           6

<210> SEQ ID NO 19
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 19 aacgttct                                                         8

<210> SEQ ID NO 20
<211> LENGTH: 7
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 20 aacgttg                                                                    7

<210> SEQ ID NO 21
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 21 aacgttga                                                                   8

<210> SEQ ID NO 22
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 22
aacgttgagg ggcat                                                           15

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
aaggtggggc agtctcaggg a                                                    21

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 24
aatagtcgcc ataacaaaac                                                      20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 25
```
aatagtcgcc atcccccccc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 26
aatagtcgcc atcccgggac                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 27
aatagtcgcc atcgcgcgac                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 28
aatagtcgcc atggcggggc                                               20

<210> SEQ ID NO 29
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 29
aattctctat cggggcttct gtgtctgttg ctggttccgc tttat                   45

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
acaaccacga gaacgggaac                                               20

<210> SEQ ID NO 31
<211> LENGTH: 8
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 31 acaacgtt                                                                 8

<210> SEQ ID NO 32
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 32
acaacgttga                                                              10

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
accacaacga gaggaacgca                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
accatcctga ggccattcgg                                                   20

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 35
accatggacg aactgtttcc cctc                                              24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 36
accatggacg acctgtttcc cctc                                              24
```

```
<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 37
accatggacg agctgtttcc cctc                                              24

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
accatggacg agctgtttcc cctc                                              24

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 39
accatggacg atctgtttcc cctc                                              24

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 40
accatggacg gtctgtttcc cctc                                              24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 41
accatggacg tactgtttcc cctc                                              24

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphorothioate backbone

<400> SEQUENCE: 42
accatggacg ttctgtttcc cctc                                              24

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 43
acccatcaat agctctgtgc                                                   20

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 44
acccgtcgta attatagtaa aaccc                                             25

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 45
accgcatgga ttctaggcca                                                   20

<210> SEQ ID NO 46
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 46
accttattaa gattgtgcaa tgtgacgtcc tttagcatcg caaga                       45

<210> SEQ ID NO 47
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 47
acgctggacc ttccat                                                       16
```

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 48
acgtcgttcc cccccccccc                                                    20

<210> SEQ ID NO 49
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 49 acgtgt                                                                    6

<210> SEQ ID NO 50
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 50
actagacgtt agtgtga                                                       17

<210> SEQ ID NO 51
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 51
actagacgtt agtgtga                                                       17

<210> SEQ ID NO 52
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 52
actggacgtt agcgtga                                                       17

<210> SEQ ID NO 53
<211> LENGTH: 25

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 53
acttctcata gtccctttgg tccag                                          25

<210> SEQ ID NO 54
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 54 agaacgtt                                                              8

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agacagacac gaaacgaccg                                                20

<210> SEQ ID NO 56
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 56
agactcatgg gaaaatccca catttga                                        27

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 57
agatagcaaa tcggctgacg                                                20

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
```

```
agatggttct cagataaagc ggaa                                          24

<210> SEQ ID NO 59
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 59
agcaccgaac gtgagagg                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 60
agcacggtag ccttccta                                                 18

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 61
agcagcttta gagctttaga gctt                                          24

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 62
agcatcagga acgacatgga                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 63
agcatcagga ccgacatgga                                               20

<210> SEQ ID NO 64
<211> LENGTH: 8
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 64 agcgctga                                                                    8

<210> SEQ ID NO 65
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 65
agctcaacgt catgc                                                           15

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 66
agctccatgg tgctcactg                                                       19

<210> SEQ ID NO 67
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 67 aggatatc                                                                    8

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
aggtacagcc aggactacga                                                      20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (3)...(3)
```

```
<223> OTHER INFORMATION: I
<221> NAME/KEY: modified_base
<222> LOCATION: (8)...(8)
<223> OTHER INFORMATION: I
<221> NAME/KEY: modified_base
<222> LOCATION: (14)...(14)
<223> OTHER INFORMATION: I

<400> SEQUENCE: 69
agncccgnga acgnattcac                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 70
agtgactctc cagcgttctc                                               20

<210> SEQ ID NO 71
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 71
agtgcgattc gagatcg                                                  17

<210> SEQ ID NO 72
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 72
agtgcgattg cagatcg                                                  17

<210> SEQ ID NO 73
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 73 agtgct                                                               6

<210> SEQ ID NO 74
<211> LENGTH: 6
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphodiester backbone

<400> SEQUENCE: 74 agtgct                                                                      6

<210> SEQ ID NO 75
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 75
agttgcaact                                                                 10

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 76
ataaagcgaa actagcagca gtttc                                                25

<210> SEQ ID NO 77
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 77 ataacgtt                                                                    8

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 78
ataatagagc ttcaagcaag                                                      20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
```

```
<400> SEQUENCE: 79
ataatccagc ttgaaccaag                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 80
ataatcgacg ttcaagcaag                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 81
ataatcgacg ttcccccccc                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 82
ataatcgtcg ttcaagcaag                                              20

<210> SEQ ID NO 83
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 83
ataatcgtgc gttcaagaaa g                                            21

<210> SEQ ID NO 84
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 84
atagacaaaa attccctccc cggagcc                                      27
```

```
<210> SEQ ID NO 85
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 85
atatatatat atatatat                                                       18

<210> SEQ ID NO 86
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 86
atatctaatc aaaacattaa caaa                                                24

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 87
atcaggaacg tcatgggaag c                                                   21

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 88
atcgacctac gtgcgttctc                                                     20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (18)...(18)
<223> OTHER INFORMATION: m5c

<400> SEQUENCE: 89
atcgacctac gtgcgttntc                                                     20
```

```
<210> SEQ ID NO 90
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 90
atcgactcga gcgttctc                                                 18

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 91
atcgactctc gagcgttctc                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 92
atcgactctc gagcgttctc                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 93
atcgactctc gagtgttctc                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (14)...(14)
<223> OTHER INFORMATION: m5c

<400> SEQUENCE: 94
atcgactctc gagngttctc                                               20
```

```
<210> SEQ ID NO 95
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 95
atcgactctc tcgagcgttc tc                                              22

<210> SEQ ID NO 96
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 96
atcgacttcg agcgttctc                                                  19

<210> SEQ ID NO 97
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 97
atcgatcgag cgttctc                                                    17

<210> SEQ ID NO 98
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 98 atcgatgt                                                               8

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
atcggaggac tggcgcgccg                                                 20

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphorothioate backbone

<400> SEQUENCE: 100
atctggtgag ggcaagctat g                                              21

<210> SEQ ID NO 101
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 101
atgacgttcc tgacgtt                                                   17

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 102
atgcactctg cagcgttctc                                                20

<210> SEQ ID NO 103
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 103 atgcatgt                                                              8

<210> SEQ ID NO 104
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 104 atgccccctca acgtt                                                    15

<210> SEQ ID NO 105
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 105
```
atgctaaagg acgtcacatt gca                                    23

<210> SEQ ID NO 106
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 106
atggaaggtc cacgttctc                                         19

<210> SEQ ID NO 107
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 107
atggaaggtc cagcgttct                                         19

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 108
atggaaggtc cagcgttctc                                        20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 109
atggaaggtc cagtgttctc                                        20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 110
atggaaggtc gagcgttctc                                        20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 111
atggactctc cagcgttctc                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 112
atgtcctcgg tcctgatgct                                              20

<210> SEQ ID NO 113
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 113
atgtttacta gacaaaattc ccccagaatg ttt                               33

<210> SEQ ID NO 114
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 114
atgtttactt cttaaaattc ccccagaatg ttt                               33

<210> SEQ ID NO 115
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 115
attcgatcgg ggcggggcga g                                            21

<210> SEQ ID NO 116
<211> LENGTH: 20
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (3)...(3)
<223> OTHER INFORMATION: m5c

<400> SEQUENCE: 116
atngacctac gtgcgttctc                                           20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (3)...(3)
<223> OTHER INFORMATION: m5c
<221> NAME/KEY: modified_base
<222> LOCATION: (10)...(10)
<223> OTHER INFORMATION: m5c
<221> NAME/KEY: modified_base
<222> LOCATION: (14)...(14)
<223> OTHER INFORMATION: m5c

<400> SEQUENCE: 117
atngactctn gagngttctc                                           20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end

<400> SEQUENCE: 118
atggaaggtc cagcgttctc                                           20

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated 5' end

<400> SEQUENCE: 119
gagaacgctc cagcactgat                                           20

<210> SEQ ID NO 120
<211> LENGTH: 20
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated 5' end

<400> SEQUENCE: 120
gagaacgctc gaccttcgat                                                    20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated 5' end
<221> NAME/KEY: modified_base
<222> LOCATION: (6)...(6)
<223> OTHER INFORMATION: m5c

<400> SEQUENCE: 121
gagaangctc cagcactgat                                                    20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated 5' end
<221> NAME/KEY: modified_base
<222> LOCATION: (6)...(6)
<223> OTHER INFORMATION: m5c

<400> SEQUENCE: 122
gagaangctc gaccttcgat                                                    20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end

<400> SEQUENCE: 123
gagcaagctg gaccttccat                                                    20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end
<221> NAME/KEY: modified_base
<222> LOCATION: (8)...(8)
<223> OTHER INFORMATION: m5c

<400> SEQUENCE: 124
gagcaagntg gaccttccat                                                   20

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end

<400> SEQUENCE: 125
gctagacgtt agcgtga                                                      17

<210> SEQ ID NO 126
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end

<400> SEQUENCE: 126 tcaacgtt                                                                 8

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: biotinylated at 5' end

<400> SEQUENCE: 127
tccatgacgt tcctgatgct                                                   20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
```

```
<222> LOCATION: (1)...(1)
<223> OTHER INFORMATION: biotinylated at 5' end

<400> SEQUENCE: 128
tccatgagct tcctgatgct                                               20

<210> SEQ ID NO 129
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 5' end
<221> NAME/KEY: misc_feature
<222> LOCATION: (1)...(1)
<223> OTHER INFORMATION: biotinylated at 5' end

<400> SEQUENCE: 129
tccattccat gacgttcctg atgcttcca                                     29

<210> SEQ ID NO 130
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 5' end
<221> NAME/KEY: misc_feature
<222> LOCATION: (1)...(1)
<223> OTHER INFORMATION: biotinylated at 5' end

<400> SEQUENCE: 130
tccattccat tctaggcctg agtcttccat                                    30

<210> SEQ ID NO 131
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 5' end
<221> NAME/KEY: misc_feature
<222> LOCATION: (1)...(1)
<223> OTHER INFORMATION: biotinylated at 5' end

<400> SEQUENCE: 131
tcgtcgtttt gtcgttttgt cgttttttt                                     29

<210> SEQ ID NO 132
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 5' end
<221> NAME/KEY: misc_feature
<222> LOCATION: (1)...(1)
<223> OTHER INFORMATION: biotinylated at 5' end
```

<400> SEQUENCE: 132 ttttccatg tcgttcctga tgcttttt                                28

<210> SEQ ID NO 133
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
    backbone with phosphodiester on 5' end
<221> NAME/KEY: misc_feature
<222> LOCATION: (1)...(1)
<223> OTHER INFORMATION: biotinylated at 5' end

<400> SEQUENCE: 133
tttttcgtcg ttcccccccc cccc                                   24

<210> SEQ ID NO 134
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 134 caaacgtt                                                     8

<210> SEQ ID NO 135
<211> LENGTH: 7
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 135 caacgtt                                                      7

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 136
caagagatgc taacaatgca                                        20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
caatcaatct gaggagaccc                                        20

```
<210> SEQ ID NO 138
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 138
cacaccttgg tcaatgtcac gt                                             22

<210> SEQ ID NO 139
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 139
caccaccttg gtcaatgtca cgt                                            23

<210> SEQ ID NO 140
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 140
cacggtagcc ttccta                                                    16

<210> SEQ ID NO 141
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 141
cacgttgagg ggcat                                                     15

<210> SEQ ID NO 142
<211> LENGTH: 16
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 142
cactgtcctt cgtcga                                                    16

<210> SEQ ID NO 143
<211> LENGTH: 23
<212> TYPE: DNA
<213> ORGANISM: Artificial Sequence
```

```
<220> FEATURE:
<223> OTHER INFORMATION: Synthetic oligonucleotide

<400> SEQUENCE: 143
cagacacaga agcccgatag acg                                                23

<210> SEQ ID NO 144
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 144
cagattgtgc aatgtctcga                                                    20

<210> SEQ ID NO 145
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 145
cataacatag gaatatttac tcctcgc                                             27

<210> SEQ ID NO 146
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 146
cataggatct cgagctcgga aagtcccta c                                        31

<210> SEQ ID NO 147
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 147
catgagctca tctggaggaa gcgg                                               24

<210> SEQ ID NO 148
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 148
```
catttccacg atttccca                                              18

<210> SEQ ID NO 149
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 149
cattttacgg gcgggcgggc                                            20

<210> SEQ ID NO 150
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 150
ccaaatatcg gtggtcaagc ac                                         22

<210> SEQ ID NO 151
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 151 ccaacgtt                                                          8

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 152
ccacgtcgac cctcaggcga                                            20

<210> SEQ ID NO 153
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 153
ccacgtggac ctctagc                                               17

<210> SEQ ID NO 154
<211> LENGTH: 25
<212> TYPE: DNA
<213> ORGANISM: Artificial Sequence
<220> FEATURE:
<223> OTHER INFORMATION: Synthetic oligonucleotide

```
<221> NAME/KEY: misc_feature
<222> LOCATION: (0)...(0)
<223> OTHER INFORMATION: phosphodiester backbone

<400> SEQUENCE: 154
ccactcacat ctgctgctcc acaag                                         25

<210> SEQ ID NO 155
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 155
ccagatgagc tcatgggttt ctcc                                          24

<210> SEQ ID NO 156
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 156
ccaggttaag aggaaatgac ttcggg                                        26

<210> SEQ ID NO 157
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 157
ccaggttgta tagaggc                                                  17

<210> SEQ ID NO 158
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 158
ccagtgctga tcaccgatat cctgttcggc agtcg                              35

<210> SEQ ID NO 159
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 159 ccatcgat                                                             8

<210> SEQ ID NO 160
```

```
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 160 ccatgcat                                                                    8

<210> SEQ ID NO 161
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 161
ccatgctaac ctctagc                                                         17

<210> SEQ ID NO 162
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 162
ccatgtcggt cctgatgct                                                       19

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 163
ccccaaaggg atgagaagtt                                                      20

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 164 ccccaaaaa aaaaccccc                                                        20

<210> SEQ ID NO 165
<211> LENGTH: 6
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 165 cccccc                                                              6

<210> SEQ ID NO 166
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 166 cccccccc                                                            8

<210> SEQ ID NO 167
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 167
cccccccccc cc                                                      12

<210> SEQ ID NO 168
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 168
cccccccccc cccccccccc                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 169
cccccccccc cccccccccc                                              20

<210> SEQ ID NO 170
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

```
<223> OTHER INFORMATION: phosphorothioate backbone

<400> SEQUENCE: 170
cccccccccc cccccccccc cccc                                          24

<210> SEQ ID NO 171
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 171
cccccccccc cccccccccc ccccccc                                       28

<210> SEQ ID NO 172
<211> LENGTH: 35
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 172
cccccccccc cccccccccc cccccccccc ccccc                              35

<210> SEQ ID NO 173
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 173
ccccttgacg ttttcccccc                                               20

<210> SEQ ID NO 174
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 174
cccgaagtca tttcctctta acctgg                                        26

<210> SEQ ID NO 175
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 175
ccgaacagga tatcggtgat cagcac                                        26
```

<210> SEQ ID NO 176
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 176
ccgcttcctc cagatgagct catg                                              24

<210> SEQ ID NO 177
<211> LENGTH: 39
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 177
ccgcttcctc cagatgagct catgggtttc tccaccaag                              39

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 178
ccggccggcc ggccggccgg                                                   20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphodiester backbone

<400> SEQUENCE: 179
ccgtcgttcc cccccccccc                                                   20

<210> SEQ ID NO 180
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 180
cctacgttgt atgcgcccag ct                                                22

<210> SEQ ID NO 181
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 181
cctccaaatg aaagaccccc                                              20

<210> SEQ ID NO 182
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 182
cctctataca acctgggac                                               19

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 183
ccttccatgt cggtcctgat                                              20

<210> SEQ ID NO 184
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphodiester backbone

<400> SEQUENCE: 184 ccttcgat                                                            8

<210> SEQ ID NO 185
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 185 cgaacgtt                                                            8

<210> SEQ ID NO 186
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 186
``` cgacga                                                        6

<210> SEQ ID NO 187
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 187 cgacgt                                                        6

<210> SEQ ID NO 188
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 188
cgactctcga gcgttctc                                          18

<210> SEQ ID NO 189
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 189
cgactgccga acaggatatc ggtgatcagc actgg                       35

<210> SEQ ID NO 190
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 190
cgccgtcgcg gcggttgg                                          18

<210> SEQ ID NO 191
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 191
cgcctggggc tggtctgg                                          18

<210> SEQ ID NO 192
<211> LENGTH: 20
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 192
cgcgcgcgcg cgcgcgcgcg                                                    20

<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 193
cgcgcgcgcg cgcgcgcgcg                                                    20

<210> SEQ ID NO 194
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 194 cgcgta                                                                    6

<210> SEQ ID NO 195
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 195
cgctagaggt tagcgtga                                                      18

<210> SEQ ID NO 196
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 196
cgctggacct tccat                                                         15

<210> SEQ ID NO 197
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

-continued

```
<223> OTHER INFORMATION: chimeric phosphorothioate/phosphodiester
      backbone with phosphorothioate at 5' and 3' ends

<400> SEQUENCE: 197
cgctggacct tccatgtcgg                                            20

<210> SEQ ID NO 198
<211> LENGTH: 16
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 198
cggctgacgt catcaa                                                16

<210> SEQ ID NO 199
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 199
cgggcgactc agtctatcgg                                            20

<210> SEQ ID NO 200
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 200
cgggcttacg gcggatgctg                                            20

<210> SEQ ID NO 201
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 201
cggtagcctt ccta                                                  14

<210> SEQ ID NO 202
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 202
cgtaccttac ggtga                                                 15

<210> SEQ ID NO 203
<211> LENGTH: 6
<212> TYPE: DNA
<213> ORGANISM: Artificial Sequence
<220> FEATURE:
```

<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 203 cgtacg                                                                     6

<210> SEQ ID NO 204
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 204 cgtcga                                                                     6

<210> SEQ ID NO 205
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 205 cgtcga                                                                     6

<210> SEQ ID NO 206
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 206 cgtcgt                                                                     6

<210> SEQ ID NO 207
<211> LENGTH: 9
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 207 cgtcgtcgt                                                                  9

<210> SEQ ID NO 208
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

```
<400> SEQUENCE: 208
cgtcgtcgtc gtcgtcgtcg t                                    21

<210> SEQ ID NO 209
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 209
cgtctatcgg gcttctgtgt ctg                                  23

<210> SEQ ID NO 210
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 210 cgttcg                                                      6

<210> SEQ ID NO 211
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 211 ctaacgtt                                                    8

<210> SEQ ID NO 212
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 212
ctaatctttc taattttttt ctaa                                 24

<210> SEQ ID NO 213
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 213
ctagataaag cggaaccagc aacagacaca gaagccccga tagag          45

<210> SEQ ID NO 214
```

```
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 214 ctagcgct                                                                    8

<210> SEQ ID NO 215
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 215
ctagcggctg acgtcataaa gctagc                                               26

<210> SEQ ID NO 216
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 216
ctagcggctg acgtcatcaa gctag                                                25

<210> SEQ ID NO 217
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 217
ctagcggctg acgtcatcaa tctag                                                25

<210> SEQ ID NO 218
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 218
ctagcggctg agctcataaa gctagc                                               26

<210> SEQ ID NO 219
<211> LENGTH: 25
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 219
ctagcttgat gacgtcagcc gctag                                              25

<210> SEQ ID NO 220
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 220
ctagcttgat gagctcagcc gctag                                              25

<210> SEQ ID NO 221
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 221
ctagctttat gacgtcagcc gctagc                                             26

<210> SEQ ID NO 222
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 222
ctaggctgac gtcatcaagc tagt                                               24

<210> SEQ ID NO 223
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 223
ctagtggctg acgtcatcaa gctag                                              25

<210> SEQ ID NO 224
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 224
```

```
ctatcggagg actggcgcgc c                                              21
```

<210> SEQ ID NO 225
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 225

```
ctatcggagg actggcgcgc cg                                             22
```

<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 226

```
ctcaacgctg gaccttccat                                                20
```

<210> SEQ ID NO 227
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 227

```
ctcatgggtt tctccaccaa g                                              21
```

<210> SEQ ID NO 228
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 228

```
ctccagctcc aagaaaggac g                                              21
```

<210> SEQ ID NO 229
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 229

```
ctcgccccgc cccgatcgaa t                                              21
```

<210> SEQ ID NO 230
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 230
ctctccaagc tcacttacag                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 231
ctctctgtag gcccgcttgg                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 232
ctcttgcgac ctggaaggta                                               20

<210> SEQ ID NO 233
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 233
ctgacgtcat                                                          10

<210> SEQ ID NO 234
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 234 ctgacgtg                                                            8

<210> SEQ ID NO 235
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 235
ctgattgctc tctcgtga                                                 18
```

```
<210> SEQ ID NO 236
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 236
ctgattgctc tctcgtga                                              18

<210> SEQ ID NO 237
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 237
ctgcagcctg ggac                                                  14

<210> SEQ ID NO 238
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 238
ctgcgttagc aatttaactg tg                                         22

<210> SEQ ID NO 239
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 239
ctgctgagac tggag                                                 15

<210> SEQ ID NO 240
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 240
ctgctgctgc tgctgctgct g                                          21

<210> SEQ ID NO 241
<211> LENGTH: 16
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 241
ctggaccttc catgtc                                                       16

<210> SEQ ID NO 242
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 242
ctggaccttc catgtcgg                                                     18

<210> SEQ ID NO 243
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 243
ctggtctttc tggttttttt ctgg                                              24

<210> SEQ ID NO 244
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 244
ctggtctttc tggttttttt ctgg                                              24

<210> SEQ ID NO 245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 245
ctgtaagtga gcttggagag                                                   20

<210> SEQ ID NO 246
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphodiester backbone

<400> SEQUENCE: 246
ctgtatgaaa caaatttttcc tctttgggca                                      30

<210> SEQ ID NO 247
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 247 ctgtca                                                                  6

<210> SEQ ID NO 248
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 248
ctgtcaggaa ctgcaggtaa gg                                               22

<210> SEQ ID NO 249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 249
ctgtcccata ttttttagaca                                                 20

<210> SEQ ID NO 250
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 250 ctgtcg                                                                  6

<210> SEQ ID NO 251
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 251 ctgtcg                                                                  6
```

```
<210> SEQ ID NO 252
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 252
ctgtcgttcc cccccccccc                                           20

<210> SEQ ID NO 253
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 253
ctgtgctttc tgtgtttttc tgtg                                      24

<210> SEQ ID NO 254
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 254
cttggagggc ctcccggcgg                                           20

<210> SEQ ID NO 255
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 255
cttggtggag aaacccatga g                                         21

<210> SEQ ID NO 256
<211> LENGTH: 39
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 256
cttggtggag aaacccatga gctcatctgg aggaagcgg                      39

<210> SEQ ID NO 257
<211> LENGTH: 20
<212> TYPE: DNA
<213> ORGANISM: Artificial Sequence
<220> FEATURE:
<223> OTHER INFORMATION: Synthetic oligonucleotide
```

<221> NAME/KEY: misc_feature
<222> LOCATION: (0)...(0)
<223> OTHER INFORMATION: phosphorothioate backbone

<400> SEQUENCE: 257
ctttccgttg gaccccctggg                                        20

<210> SEQ ID NO 258
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c
<221> NAME/KEY: modified_base
<222> LOCATION: (6)...(6)
<223> OTHER INFORMATION: m5c
<221> NAME/KEY: modified_base
<222> LOCATION: (10)...(10)
<223> OTHER INFORMATION: m5c
<221> NAME/KEY: modified_base
<222> LOCATION: (15)...(15)
<223> OTHER INFORMATION: m5c

<400> SEQUENCE: 258
cnggcnggcn gggcnccgg                                          19

<210> SEQ ID NO 259
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: FITC labeled

<400> SEQUENCE: 259 aacgttga                                                       8

<210> SEQ ID NO 260
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: FITC labeled

<400> SEQUENCE: 260
cgcgaattcg cg                                                 12

<210> SEQ ID NO 261
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature

```
<222> LOCATION: (0)...(0)
<223> OTHER INFORMATION: phosphodiester backbone
<221> NAME/KEY: misc_feature
<222> LOCATION: (1)...(1)
<223> OTHER INFORMATION: FITC labeled

<400> SEQUENCE: 261 tcaacgtt                                                                  8

<210> SEQ ID NO 262
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 262 gaaacgtt                                                                  8

<210> SEQ ID NO 263
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 263
gaaactgctg ctagtttcgc tttat                                              25

<210> SEQ ID NO 264
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 264
gaaccttcca tgctgtt                                                       17

<210> SEQ ID NO 265
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 265
gaaccttcca tgctgttccg                                                    20

<210> SEQ ID NO 266
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 266
gaacgctgga ccttccat                                                      18

<210> SEQ ID NO 267
<211> LENGTH: 21
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 267
gaagttcacg ttgaggggca t                                                    21

<210> SEQ ID NO 268
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 268
gaagtttctg gtaagtcttc g                                                    21

<210> SEQ ID NO 269
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 269
gaccttccat                                                                 10

<210> SEQ ID NO 270
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 270
gaccttccat gtcggtcctg at                                                   22

<210> SEQ ID NO 271
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 271
gaccttctat gtcggtcctg                                                      20

<210> SEQ ID NO 272
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 272 gacgtcat                                                                    8

<210> SEQ ID NO 273
```

```
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 273
gactgacgtc agcgt                                                        15

<210> SEQ ID NO 274
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 274
gagaacgatg gaccttccat                                                   20

<210> SEQ ID NO 275
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 275
gagaacgcta gaccttctat                                                   20

<210> SEQ ID NO 276
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 276
gagaacgctc caccttccat                                                   20

<210> SEQ ID NO 277
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 277
gagaacgctc cagcactgat                                                   20

<210> SEQ ID NO 278
<211> LENGTH: 20
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 278
gagaacgctc cagcttcgat                                                     20

<210> SEQ ID NO 279
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 279
gagaacgctc cgaccttcga t                                                   21

<210> SEQ ID NO 280
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 280
gagaacgctc gaccttccat                                                     20

<210> SEQ ID NO 281
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: misc_feature
<222> LOCATION: (20)...(20)
<223> OTHER INFORMATION: biotinylated at 3' end

<400> SEQUENCE: 281
gagaacgctc gaccttcgat                                                     20

<210> SEQ ID NO 282
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 282
gagaacgctg gacctatcca t                                                   21

<210> SEQ ID NO 283
<211> LENGTH: 25
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphodiester backbone

<400> SEQUENCE: 283
gagaacgctg gacctcatca tccat                                              25

<210> SEQ ID NO 284
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 284
gagaacgctg gacctcatcc at                                                 22

<210> SEQ ID NO 285
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 285
gagaacgctg gaccttcc                                                      18

<210> SEQ ID NO 286
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 286
gagaacgctg gaccttccat                                                    20

<210> SEQ ID NO 287
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 287
gagaacgctg gaccttccat                                                    20

<210> SEQ ID NO 288
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 288
gagaacgctg gaccttccat gt                                                 22

<210> SEQ ID NO 289
<211> LENGTH: 20
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 289
gagaacgctg gaccttcgat                                                    20

<210> SEQ ID NO 290
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 290
gagaacgctg gaccttcgta                                                    20

<210> SEQ ID NO 291
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 291
gagaacgctg gaccttgcat                                                    20

<210> SEQ ID NO 292
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 292
gagaacgctg gacgctcatc cat                                                23

<210> SEQ ID NO 293
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 293
gagaacgctg gacttccat                                                     19

<210> SEQ ID NO 294
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

<223> OTHER INFORMATION: phosphodiester backbone
<221> NAME/KEY: modified_base
<222> LOCATION: (14)...(14)
<223> OTHER INFORMATION: m5c

<400> SEQUENCE: 294
gagaacgctg gacnttccat            20

<210> SEQ ID NO 295
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 295
gagaacgctg gatccat            17

<210> SEQ ID NO 296
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 296
gagaatgctg gaccttccat            20

<210> SEQ ID NO 297
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (6)...(6)
<223> OTHER INFORMATION: m5c

<400> SEQUENCE: 297
gagaangctg gaccttccat            20

<210> SEQ ID NO 298
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 298
gagaccgctc gaccttcgat            20

<210> SEQ ID NO 299
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 299
gagcaagctg gaccttccat                                                                               20

<210> SEQ ID NO 300
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: misc_feature
<222> LOCATION: (20)...(20)
<223> OTHER INFORMATION: biotinylated at 3' end

<400> SEQUENCE: 300
gagcaagctg gaccttccat                                                                               20

<210> SEQ ID NO 301
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 301
gaggaacgtc atggagagga acgtcatgga gaggaacgtc atgga                                                   45

<210> SEQ ID NO 302
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (9)...(9)
<223> OTHER INFORMATION: I
<221> NAME/KEY: modified_base
<222> LOCATION: (11)...(11)
<223> OTHER INFORMATION: I
<221> NAME/KEY: modified_base
<222> LOCATION: (15)...(15)
<223> OTHER INFORMATION: I

<400> SEQUENCE: 302
gaggaaggng nggangacgt                                                                               20

<210> SEQ ID NO 303
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 303
gaggggacca ttttacgggc                                                                               20

<210> SEQ ID NO 304
<211> LENGTH: 33
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 304
gatccagatt ctgccaggtc actgtgactg gat                          33

<210> SEQ ID NO 305
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 305
gatccagatt ctgctgagtc actgtgactg gat                          33

<210> SEQ ID NO 306
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 306
gatccagtca cagtgacctg gcagaatctg gat                          33

<210> SEQ ID NO 307
<211> LENGTH: 33
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 307
gatccagtca cagtgactca gcagaatctg gat                          33

<210> SEQ ID NO 308
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 308
gatccggctg actcatcact agatc                                   25

<210> SEQ ID NO 309
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

<223> OTHER INFORMATION: chimeric phosphorothioate/phosphodiester
      backbone with phosphorothioate at 5' and 3' ends

<400> SEQUENCE: 309
gatcgctgat ctaatgctcg                                               20

<210> SEQ ID NO 310
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 310
gatcggagga ctggcgcgcc g                                             21

<210> SEQ ID NO 311
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 311
gatctagtga tgagtcagcc ggatc                                         25

<210> SEQ ID NO 312
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 312
gattcaactt gcgctcatct taggc                                         25

<210> SEQ ID NO 313
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 313 gcaacgtt                                                             8

<210> SEQ ID NO 314
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: biotinylated at 3' end

<400> SEQUENCE: 314
gcaatattgc                                                            10

<210> SEQ ID NO 315
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: FITC labeled

<400> SEQUENCE: 315
gcaatattgc                                                            10

<210> SEQ ID NO 316
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 316
gcacatcgtc ccgcagccga                                                 20

<210> SEQ ID NO 317
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 317
gcagcctcta tacaacctgg gacggga                                         27

<210> SEQ ID NO 318
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 318
gcatagcgtt gagct                                                      15

<210> SEQ ID NO 319
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 319
gcatgacgtt gagct                                                      15

<210> SEQ ID NO 320
<211> LENGTH: 15

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 320
gcatgacgtt gagct                                                    15

<210> SEQ ID NO 321
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 321
gcatgacgtt gagct                                                    15

<210> SEQ ID NO 322
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 322
gcatgacgtt gagct                                                    15

<210> SEQ ID NO 323
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 323
gcatgagctt gagctga                                                  17

<210> SEQ ID NO 324
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 324
gcatgatgtt gagct                                                    15

<210> SEQ ID NO 325
<211> LENGTH: 15
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: m5c

<400> SEQUENCE: 325
gcatgangtt gagct                                                   15

<210> SEQ ID NO 326
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 326
gcatggcgtt gagct                                                   15

<210> SEQ ID NO 327
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 327
gcatgtagct gagct                                                   15

<210> SEQ ID NO 328
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 328
gcatgtcgtt gagct                                                   15

<210> SEQ ID NO 329
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 329
gcattcatca ggcgggcaag aat                                          23

<210> SEQ ID NO 330
<211> LENGTH: 15
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 330
gcattgcgtt gagct                                                   15

<210> SEQ ID NO 331
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 331
gcatttcgag gagct                                                   15

<210> SEQ ID NO 332
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 332
gccaccaaaa cttgtccatg                                              20

<210> SEQ ID NO 333
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 333
gccagatgtt agctgga                                                 17

<210> SEQ ID NO 334
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 334
gccatggacg aactgttccc cctc                                         24

<210> SEQ ID NO 335
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
```

```
<400> SEQUENCE: 335
gcgacgggcg gcgcgcgccc                                               20

<210> SEQ ID NO 336
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 336
gcgacggtcg gcgcgcgccc                                               20

<210> SEQ ID NO 337
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 337
gcgacgtgcg gcgcgcgccc                                               20

<210> SEQ ID NO 338
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 338
gcgacgttcg gcgcgcgccc                                               20

<210> SEQ ID NO 339
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 339
gcgatgtcgt tcctgatgcg                                               20

<210> SEQ ID NO 340
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 340
gcgatgtcgt tcctgatgct                                               20
```

```
<210> SEQ ID NO 341
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 341
gcgccagtcc tccgatagac                                               20

<210> SEQ ID NO 342
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 342
gcgcgcgcgc gcgcgcgcg                                                19

<210> SEQ ID NO 343
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 343
gcgctaccgg tagcctgagt                                               20

<210> SEQ ID NO 344
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 344
gcggcgggcg gcgcgcgccc                                               20

<210> SEQ ID NO 345
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 345
gcggcgggcg gcgcgcgccc                                               20

<210> SEQ ID NO 346
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
```

<400> SEQUENCE: 346
gcggcggtcg gcgcgcgccc          20

<210> SEQ ID NO 347
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 347
gcggcgtgcg gcgcgcgccc          20

<210> SEQ ID NO 348
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 348
gcggcgttcg gcgcgcgccc          20

<210> SEQ ID NO 349
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 349
gcgtcgttcc cccccccccc          20

<210> SEQ ID NO 350
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 350
gcgtgcgttg tcgttgtcgt t          21

<210> SEQ ID NO 351
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 351
gcgttttttt ttgcg          15

<210> SEQ ID NO 352
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 352
gctaaacgtt agcgt                                                    15

<210> SEQ ID NO 353
<211> LENGTH: 16
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 353
gctaacgtta gcgtga                                                   16

<210> SEQ ID NO 354
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 354
gctaccttag cgtga                                                    15

<210> SEQ ID NO 355
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (11)...(11)
<223> OTHER INFORMATION: m5c

<400> SEQUENCE: 355
gctaccttag ngtga                                                    15

<210> SEQ ID NO 356
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 356
gctacttagc gtga                                                     14

```
<210> SEQ ID NO 357
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 357
gctagacgat agcgt                                                    15

<210> SEQ ID NO 358
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 358
gctagacgct agcgtga                                                  17

<210> SEQ ID NO 359
<211> LENGTH: 9
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 359 gctagacgt                                                            9

<210> SEQ ID NO 360
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 360
gctagacgta agcgtga                                                  17

<210> SEQ ID NO 361
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 361
gctagacgtc tagc                                                     14

<210> SEQ ID NO 362
<211> LENGTH: 13
<212> TYPE: DNA
```

```
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 362
gctagacgtt agc                                                          13

<210> SEQ ID NO 363
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 363
gctagacgtt agcgt                                                        15

<210> SEQ ID NO 364
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 364
gctagacgtt agcgtga                                                      17

<210> SEQ ID NO 365
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 365
gctagacgtt agctgga                                                      17

<210> SEQ ID NO 366
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 366
gctagacgtt agctgga                                                      17

<210> SEQ ID NO 367
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

<400> SEQUENCE: 367
gctagacgtt aggctga                                                        17

<210> SEQ ID NO 368
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 368
gctagacgtt agtgt                                                          15

<210> SEQ ID NO 369
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (13)...(13)
<223> OTHER INFORMATION: m5c

<400> SEQUENCE: 369
gctagacgtt agngt                                                          15

<210> SEQ ID NO 370
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 370
gctagacgtt tagc                                                           14

<210> SEQ ID NO 371
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 371
gctagagctt agcgtga                                                        17

<210> SEQ ID NO 372
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

```
<400> SEQUENCE: 372
gctagaggtt agcgtga                                                    17

<210> SEQ ID NO 373
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 373
gctagaggtt agcgtga                                                    17

<210> SEQ ID NO 374
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 374
gctagatgtt aacgt                                                      15

<210> SEQ ID NO 375
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 375
gctagatgtt agcgt                                                      15

<210> SEQ ID NO 376
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 376
gctagatgtt agcgt                                                      15

<210> SEQ ID NO 377
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 377
gctagatgtt agcgtga                                                    17
```

```
<210> SEQ ID NO 378
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: m5c

<400> SEQUENCE: 378
gctagangtt agcgt                                                    15

<210> SEQ ID NO 379
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: m5c
<400> SEQUENCE: 379
gctagangtt agtgt                                                    15

<210> SEQ ID NO 380
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 380
gctagcttta gagctttaga gctt                                          24

<210> SEQ ID NO 381
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 381
gctaggcgtt agcgt                                                    15

<210> SEQ ID NO 382
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 382
gctagtcgat agc                                                      13
```

```
<210> SEQ ID NO 383
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 383
gctagtcgat agcgt                                                       15

<210> SEQ ID NO 384
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 384
gctagtcgct agc                                                         13

<210> SEQ ID NO 385
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 385
gctandcghh agc                                                         13

<210> SEQ ID NO 386
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 386
gctatgacgt tccaaggg                                                    18

<210> SEQ ID NO 387
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphorothioate backbone

<400> SEQUENCE: 387 gctcga                                                                  6

<210> SEQ ID NO 388
<211> LENGTH: 17
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 388
gctcgttcag cgcgtct                                                    17

<210> SEQ ID NO 389
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 389
gctgaacctt ccatgctgtt                                                 20

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 390
gctgagctca tgccgtctgc                                                 20

<210> SEQ ID NO 391
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 391
gctggacctt ccat                                                       14

<210> SEQ ID NO 392
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 392
gctggacctt ccat                                                       14

<210> SEQ ID NO 393
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 393
gctggccagc ttacctcccg                                                 20
```

```
<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 394
gctgtaaaat gaatcggccg                                                   20

<210> SEQ ID NO 395
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 395
gctgtggggc ggctcctg                                                     18

<210> SEQ ID NO 396
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 396
gcttgacgtc aagc                                                         14

<210> SEQ ID NO 397
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 397
gcttgacgtc tagc                                                         14

<210> SEQ ID NO 398
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 398
gcttgacgtt tagc                                                         14

<210> SEQ ID NO 399
```

```
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 399
gcttgcgttg cgttt                                                      15

<210> SEQ ID NO 400
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 400
gcttggaggg cctgtaagtg                                                 20

<210> SEQ ID NO 401
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 401 ggaacgtt                                                               8

<210> SEQ ID NO 402
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 402
ggaagacgtt aga                                                        13

<210> SEQ ID NO 403
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 403
ggaattagta atagatatag aagtt                                           25

<210> SEQ ID NO 404
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphodiester backbone

<400> SEQUENCE: 404
ggagaaaccc atgagctcat ctgg                                          24

<210> SEQ ID NO 405
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 405
ggagctcttc gaacgccata                                               20

<210> SEQ ID NO 406
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 406
ggcagtgcag gctcaccggg                                               20

<210> SEQ ID NO 407
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 407
ggccaacttt caatgtggga tggcctc                                       27

<210> SEQ ID NO 408
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 408
ggccatccca cattgaaagt t                                             21

<210> SEQ ID NO 409
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 409 ggcctttttcc ccccccccc                                               20

<210> SEQ ID NO 410
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

-continued

<223> OTHER INFORMATION: phosphodiester backbone

<400> SEQUENCE: 410
ggcggcggcg gcggcggcgg                                               20

<210> SEQ ID NO 411
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 411
ggcgttattc ctgactcgcc                                               20

<210> SEQ ID NO 412
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 412
ggctatgtcg atcctagcc                                                19

<210> SEQ ID NO 413
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 413
ggctatgtcg ttcctagcc                                                19

<210> SEQ ID NO 414
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 414
ggctccgggg agggaattttt tgtctat                                      27

<210> SEQ ID NO 415
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 415
ggctgtattc ctgactgccc                                              20

<210> SEQ ID NO 416
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 416
gggaatgaaa gattttatta taag                                         24

<210> SEQ ID NO 417
<211> LENGTH: 38
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 417
ggggactttc cgctggggac tttccagggg gactttcc                           38

<210> SEQ ID NO 418
<211> LENGTH: 39
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 418
ggggagggag gaacttctta aaattccccc agaatgttt                          39

<210> SEQ ID NO 419
<211> LENGTH: 9
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 419 ggggagggg                                                           9

<210> SEQ ID NO 420
<211> LENGTH: 9
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 420 ggggagggt                                                           9

```
<210> SEQ ID NO 421
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 421
ggggcatgac gttcaaaaaa                                                      20

<210> SEQ ID NO 422
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 422
ggggcatgac gttcaaaaaa                                                      20

<210> SEQ ID NO 423
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 423
ggggcatgac gttcggggggg                                                     20

<210> SEQ ID NO 424
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 424
ggggcatgac gttcggggggg                                                     20

<210> SEQ ID NO 425
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 425
ggggcatgag cttcggggggg                                                     20

<210> SEQ ID NO 426
<211> LENGTH: 20
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 426
ggggcatgag cttcgggggg                                              20

<210> SEQ ID NO 427
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 427
ggggcctcta tacaacctgg g                                            21

<210> SEQ ID NO 428
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 428
gggggacgtt ggggg                                                   15

<210> SEQ ID NO 429
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 429
gggggggggg gggggggggg                                              20

<210> SEQ ID NO 430
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 430
gggggggggg gggggggggg                                              20

<210> SEQ ID NO 431
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphodiester backbone

<400> SEQUENCE: 431 gggggggttgg ggaaaacccg gacttcctgc a                                          31

<210> SEQ ID NO 432
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 432
gggggttttt tttttggggg                                                        20

<210> SEQ ID NO 433
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 433
ggggtaatcg atcagggggg                                                        20

<210> SEQ ID NO 434
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 434
ggggtaatcg atgagggggg                                                        20

<210> SEQ ID NO 435
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 435
ggggtaatgc atcagggggg                                                        20

<210> SEQ ID NO 436
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
``` backbone with phosphorothioate at 5' and 3' ends

<400> SEQUENCE: 436 gggtcaacg ttgagggggg                     20

<210> SEQ ID NO 437
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 437 gggtcaacg ttgagggggg                     20

<210> SEQ ID NO 438
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
    backbone with phosphorothioate at 5' and 3' ends

<400> SEQUENCE: 438 gggtcaagc ttgagggggg                     20

<210> SEQ ID NO 439
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
    backbone with phosphorothioate at 5' and 3' ends

<400> SEQUENCE: 439 gggtcaagt ctgagggggg                     20

<210> SEQ ID NO 440
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
    backbone with phosphorothioate at 5' and 3' ends

<400> SEQUENCE: 440 gggtccagc gtgcgccatg gggg                24

<210> SEQ ID NO 441
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 441

```
ggggtccctg agactgcc                                          18

<210> SEQ ID NO 442
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 442
ggggtcgacc ttggaggggg g                                      21

<210> SEQ ID NO 443
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 443
ggggtcgacg tcgaggggggg                                       20

<210> SEQ ID NO 444
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 444
ggggtcgtcg ttttgggggg                                        20

<210> SEQ ID NO 445
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 445
ggggtctgtc gttttgggggg g                                     21

<210> SEQ ID NO 446
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 446
ggggtctgtg cttttgggggg g                                     21

<210> SEQ ID NO 447
```

```
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 447 gggggtgacgt tcaggggggg                                                 19

<210> SEQ ID NO 448
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 448
ggggtgtcgt tcagggggg                                                   19

<210> SEQ ID NO 449
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 449 gggggttgacg ttttggggggg                                                20

<210> SEQ ID NO 450
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 450
ggggttgggg gtt                                                         13

<210> SEQ ID NO 451
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 451
ggtacctgtg gggacattgt g                                                21

<210> SEQ ID NO 452
<211> LENGTH: 9
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 452 ggtgaggtg                                                                  9

<210> SEQ ID NO 453
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 453
ggtggtgtag gttttgg                                                        17

<210> SEQ ID NO 454
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 454
ggttacggtc tgtcccatat                                                     20

<210> SEQ ID NO 455
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 455
ggttcacgtg ctcatggctg                                                     20

<210> SEQ ID NO 456
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 456 gtaacgtt                                                                   8

<210> SEQ ID NO 457
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 457
```
gtagccttcc ta                                                    12

<210> SEQ ID NO 458
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 458 gtagggact ttccgagctc gagatcctat g                                31

<210> SEQ ID NO 459
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 459
gtcactcgtg gtacctcga                                             19

<210> SEQ ID NO 460
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 460
gtccatggcg tgcgggatga                                            20

<210> SEQ ID NO 461
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 461
gtcccaggtt gtatagaggc tgc                                        23

<210> SEQ ID NO 462
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 462
gtccccattt cccagaggag gaaat                                      25

<210> SEQ ID NO 463
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature -continued

```
<222> LOCATION: (0)...(0)
<223> OTHER INFORMATION: phosphorothioate backbone

<400> SEQUENCE: 463
gtccgggcca ggccaaagtc                                              20

<210> SEQ ID NO 464
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 464
gtcggtcctg atgctgttcc                                              20

<210> SEQ ID NO 465
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 465
gtctatcgga ggactggcgc                                              20

<210> SEQ ID NO 466
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 466
gtctgtccca tgatctcgaa                                              20

<210> SEQ ID NO 467
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: I
<221> NAME/KEY: modified_base
<222> LOCATION: (13)...(13)
<223> OTHER INFORMATION: I
<221> NAME/KEY: modified_base
<222> LOCATION: (18)...(18)
<223> OTHER INFORMATION: I

<400> SEQUENCE: 467
gtgaatncgt tcncgggnct                                              20

<210> SEQ ID NO 468
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphorothioate backbone

<400> SEQUENCE: 468
gtgccggggt ctccgggc                                                18

<210> SEQ ID NO 469
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 469
gtgccggggt ctccgggc                                                18

<210> SEQ ID NO 470
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 470
gtgcgcgcga gcccgaaatc                                              20

<210> SEQ ID NO 471
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 471
gtgctgatca ccgatatcct gttcgg                                       26

<210> SEQ ID NO 472
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 472
gtgcttgacc accgatattt gg                                           22

<210> SEQ ID NO 473
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 473
gtggttacgg tcgtgcccat                                              20

<210> SEQ ID NO 474
<211> LENGTH: 18
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 474
gtgtcggggt ctccgggc                                                18

<210> SEQ ID NO 475
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 475
gttctcagat aaagcggaac cagcaacaga cacagaa                           37

<210> SEQ ID NO 476
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 476
gttgaaaccc gagaacatca t                                            21

<210> SEQ ID NO 477
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphodiester backbone

<400> SEQUENCE: 477
gttggataca ggccagactt tgttg                                        25

<210> SEQ ID NO 478
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 478 gttttatat aatttggg                                                 18

<210> SEQ ID NO 479
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: biotinylated at 3' end
```

```
<221> NAME/KEY: modified_base
<222> LOCATION: (2)...(2)
<223> OTHER INFORMATION: m5c

<400> SEQUENCE: 479 gnaatattgc                                                              10

<210> SEQ ID NO 480
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: modified_base
<222> LOCATION: (2)...(2)
<223> OTHER INFORMATION: m5c
<221> NAME/KEY: modified_base
<222> LOCATION: (5)...(5)
<223> OTHER INFORMATION: m5c
<221> NAME/KEY: modified_base
<222> LOCATION: (9)...(9)
<223> OTHER INFORMATION: m5c
<221> NAME/KEY: modified_base
<222> LOCATION: (12)...(12)
<223> OTHER INFORMATION: m5c
<221> NAME/KEY: modified_base
<222> LOCATION: (14)...(14)
<223> OTHER INFORMATION: m5c
<221> NAME/KEY: modified_base
<222> LOCATION: (16)...(16)
<223> OTHER INFORMATION: m5c

<400> SEQUENCE: 480
gnggngggng gngngngccc                                                   20

<210> SEQ ID NO 481
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 481 taaacgtt                                                                8

<210> SEQ ID NO 482
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 482 taagcgct                                                                8

<210> SEQ ID NO 483
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 483
taagctctgt caacgccagg                                                   20
```

<210> SEQ ID NO 484
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 484
taccgagctt cgacgagatt tca                                            23

<210> SEQ ID NO 485
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 485
taccgcgtgc gaccctct                                                  18

<210> SEQ ID NO 486
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 486
tactcttcgg atcccttgcg                                                20

<210> SEQ ID NO 487
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 487
tagaaacagc attcttcttt tagggcagca ca                                  32

<210> SEQ ID NO 488
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 488 tagacgtc                                                              8

<210> SEQ ID NO 489
<211> LENGTH: 15
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 489
tagacgttag cgtga                                                          15

<210> SEQ ID NO 490
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 490
tatagtccct gagactgccc caccttctca acaacc                                   36

<210> SEQ ID NO 491
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 491
tatcggagga ctggcgcgcc g                                                   21

<210> SEQ ID NO 492
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 492
tatgccgcgc ccggacttat                                                     20

<210> SEQ ID NO 493
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 493
tcaaatgtgg gattttccca tgagtct                                             27

<210> SEQ ID NO 494
<211> LENGTH: 7
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 494 tcaacgt                                                                    7
```

```
<210> SEQ ID NO 495
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 495 tcaacgtc                                                                  8

<210> SEQ ID NO 496
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: p-ethoxy backbone

<400> SEQUENCE: 496 tcaacgtt                                                                  8

<210> SEQ ID NO 497
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 497 tcaacgtt                                                                  8

<210> SEQ ID NO 498
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 498 tcaacgtt                                                                  8

<210> SEQ ID NO 499
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 499
tcaacgttaa cgttaacgtt                                                    20

<210> SEQ ID NO 500
<211> LENGTH: 32
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: misc_feature
<222> LOCATION: (32)...(32)
<223> OTHER INFORMATION: biotinylated at 3' end

<400> SEQUENCE: 500
tcaacgttaa cgttaacgtt aacgttaacg tt                                32

<210> SEQ ID NO 501
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 501
tcaacgttga                                                         10

<210> SEQ ID NO 502
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 502
tcaacgttga                                                         10

<210> SEQ ID NO 503
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: biotinylated at 3' end

<400> SEQUENCE: 503
tcaacgttga                                                         10

<210> SEQ ID NO 504
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: FITC labeled

<400> SEQUENCE: 504
```

```
tcaacgttga                                                              10

<210> SEQ ID NO 505
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: p-ethoxy backbone

<400> SEQUENCE: 505 tcaagctt                                                                 8

<210> SEQ ID NO 506
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 506 tcaagctt                                                                 8

<210> SEQ ID NO 507
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (10)...(10)
<223> OTHER INFORMATION: FITC labeled

<400> SEQUENCE: 507
tcaatgctga                                                              10

<210> SEQ ID NO 508
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (5)...(5)
<223> OTHER INFORMATION: m5c

<400> SEQUENCE: 508 tcaangtt                                                                 8

<210> SEQ ID NO 509
<211> LENGTH: 10
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
```

```
<222> LOCATION: (10)...(10)
<223> OTHER INFORMATION: biotinylated at 3' end
<221> NAME/KEY: modified_base
<222> LOCATION: (5)...(5)
<223> OTHER INFORMATION: m5c

<400> SEQUENCE: 509 tcaangttga                                                                 10

<210> SEQ ID NO 510
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 510 tcaccggt                                                                    8

<210> SEQ ID NO 511
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 511
tcacgctaac ctctagc                                                         17

<210> SEQ ID NO 512
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 512
tcacgctaac ctctgac                                                         17

<210> SEQ ID NO 513
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 513
tcacgctaac gtctagc                                                         17

<210> SEQ ID NO 514
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

```
<223> OTHER INFORMATION: phosphodiester backbone

<400> SEQUENCE: 514 tcacgt                                                              6

<210> SEQ ID NO 515
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 515
tcagaccacg tggtcgggtg ttcctga                                      27

<210> SEQ ID NO 516
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 516
tcagaccagc tggtcgggtg ttcctga                                      27

<210> SEQ ID NO 517
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 517 tcagcgct                                                            8

<210> SEQ ID NO 518
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 518
tcagcgtgcg cc                                                      12

<210> SEQ ID NO 519
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 519
tcagctctgg tacttttca                                               20
```

```
<210> SEQ ID NO 520
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 520
tcaggaacac ccgaccacgt ggtctga                                            27

<210> SEQ ID NO 521
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 521
tcaggaacac ccgaccagct ggtctga                                            27

<210> SEQ ID NO 522
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 522
tcaggggtgg ggggaacctt                                                    20

<210> SEQ ID NO 523
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (5)...(5)
<223> OTHER INFORMATION: m5c

<400> SEQUENCE: 523 tcagngct                                                                  8

<210> SEQ ID NO 524
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 524 tcatcgat                                                                  8
```

```
<210> SEQ ID NO 525
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 525
tccaagacgt tcctgatgct                                              20

<210> SEQ ID NO 526
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 526
tccaagtagt tcctagttct                                              20

<210> SEQ ID NO 527
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 527
tccaccacgt ggctgatgct                                              20

<210> SEQ ID NO 528
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 528
tccaccacgt ggtctatgct                                              20

<210> SEQ ID NO 529
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 529
tccacgacgt tttcgacgtt                                              20

<210> SEQ ID NO 530
<211> LENGTH: 15
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 530
tccagacggt gaagt                                                      15

<210> SEQ ID NO 531
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 531
tccagacgtt gaagt                                                      15

<210> SEQ ID NO 532
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 532
tccagagctt gaagt                                                      15

<210> SEQ ID NO 533
<211> LENGTH: 16
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 533
tccagcgtgc gccata                                                     16

<210> SEQ ID NO 534
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 534
tccaggacgt tcctagttct                                                 20

<210> SEQ ID NO 535
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphorothioate backbone

<400> SEQUENCE: 535
tccaggactt ctctcaggtt                                               20

<210> SEQ ID NO 536
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 536
tccaggactt ctctcaggtt                                               20

<210> SEQ ID NO 537
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 537
tccaggactt tcctcaggtt                                               20

<210> SEQ ID NO 538
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 538
tccaggactt tcctcaggtt                                               20

<210> SEQ ID NO 539
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 539
tccaggagct tcctagttct                                               20

<210> SEQ ID NO 540
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

```
<400> SEQUENCE: 540
tccaggatgt tcctagttct                                                    20

<210> SEQ ID NO 541
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 541
tccagtctag gcctagttct                                                    20

<210> SEQ ID NO 542
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 542
tccagttcct tcctcagtct                                                    20

<210> SEQ ID NO 543
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 543
tccagttcga gcctagttct                                                    20

<210> SEQ ID NO 544
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 544
tccataacgt tcctgagtct                                                    20

<210> SEQ ID NO 545
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 545
tccataacgt tcctgatgct                                                    20
```

```
<210> SEQ ID NO 546
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 546
tccatagcga tcctagcgat                                              20

<210> SEQ ID NO 547
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 547
tccatagcgg tcctagcggt                                              20

<210> SEQ ID NO 548
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 548
tccatagcgt tcctagcgtt                                              20

<210> SEQ ID NO 549
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 549
tccatagcgt tcctagcgtt                                              20

<210> SEQ ID NO 550
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 550
tccatcacgt gcctgagtct                                              20

<210> SEQ ID NO 551
```

```
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 551
tccatgacat tcctgatgct                                                 20

<210> SEQ ID NO 552
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 552
tccatgacgg tcctgacggt                                                 20

<210> SEQ ID NO 553
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 553
tccatgacgg tcctgacggt                                                 20

<210> SEQ ID NO 554
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 554
tccatgacgg tcctgagtct                                                 20

<210> SEQ ID NO 555
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 555
tccatgacgg tcctgatgct                                                 20

<210> SEQ ID NO 556
<211> LENGTH: 20
<212> TYPE: DNA
<213> ORGANISM: Artificial Sequence
```

<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 556
tccatgacgt ccctgagtct                                                  20

<210> SEQ ID NO 557
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 557
tccatgacgt ccctgatgct                                                  20

<210> SEQ ID NO 558
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 558
tccatgacgt tcctagttct                                                  20

<210> SEQ ID NO 559
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 559
tccatgacgt tcctctccat gacgttcctc tccatgacgt tcctc                      45

<210> SEQ ID NO 560
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 560
tccatgacgt tcctgacgtt                                                  20

<210> SEQ ID NO 561
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 561
tccatgacgt tcctgacgtt                                              20

<210> SEQ ID NO 562
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 562
tccatgacgt tcctgacgtt                                              20

<210> SEQ ID NO 563
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 563
tccatgacgt tcctgacgtt                                              20

<210> SEQ ID NO 564
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 564
tccatgacgt tcctgagtct                                              20

<210> SEQ ID NO 565
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 565
tccatgacgt tcctgatcc                                               19

<210> SEQ ID NO 566
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 566
tccatgacgt tcctgatgct                                              20
```

```
<210> SEQ ID NO 567
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 567
tccatgacgt tcctgatgct                                               20

<210> SEQ ID NO 568
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 568
tccatgacgt tcctgcagtt cctgacgtt                                     29

<210> SEQ ID NO 569
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 569
tccatgacgt tcctgccgtt                                               20

<210> SEQ ID NO 570
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 570
tccatgacgt tcctgcgttt                                               20

<210> SEQ ID NO 571
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 571
tccatgacgt tcctggcggg                                               20

<210> SEQ ID NO 572
<211> LENGTH: 20
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (13)...(13)
<223> OTHER INFORMATION: m5c

<400> SEQUENCE: 572
tccatgacgt tcntgatgct                                                  20

<210> SEQ ID NO 573
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 573
tccatgagct tcctgagctt                                                  20

<210> SEQ ID NO 574
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 574
tccatgagct tcctgagtct                                                  20

<210> SEQ ID NO 575
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: p-ethoxy backbone

<400> SEQUENCE: 575
tccatgagct tcctgagtct                                                  20

<210> SEQ ID NO 576
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 576
tccatgagct tcctgagtct                                                  20

<210> SEQ ID NO 577
<211> LENGTH: 20
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 577
tccatgagct tcctgatgct                                              20

<210> SEQ ID NO 578
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 578
tccatgagct tccttgagtc t                                            21

<210> SEQ ID NO 579
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: modified_base
<222> LOCATION: (8)...(8)
<223> OTHER INFORMATION: I
<221> NAME/KEY: modified_base
<222> LOCATION: (17)...(17)
<223> OTHER INFORMATION: I

<400> SEQUENCE: 579
tccatgangt tcctgangtt                                              20

<210> SEQ ID NO 580
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 580
tccatgatgt tcctagttct                                              20

<210> SEQ ID NO 581
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (8)...(8)
<223> OTHER INFORMATION: m5c

<400> SEQUENCE: 581
tccatgangt tcctagttct                                              20

<210> SEQ ID NO 582
<211> LENGTH: 20
<212> TYPE: DNA
```

```
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (8)...(8)
<223> OTHER INFORMATION: m5c

<400> SEQUENCE: 582
tccatgangt tcctgatgct                                          20

<210> SEQ ID NO 583
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: modified_base
<222> LOCATION: (8)...(8)
<223> OTHER INFORMATION: m5c
<221> NAME/KEY: modified_base
<222> LOCATION: (17)...(17)
<223> OTHER INFORMATION: m5c

<400> SEQUENCE: 583
tccatgangt tcctgangtt                                          20

<210> SEQ ID NO 584
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 584
tccatgccgg tcctgagtct                                          20

<210> SEQ ID NO 585
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 585
tccatgccgg tcctgatgct                                          20

<210> SEQ ID NO 586
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 586
```

```
tccatgccgg tcctgccggt                                              20

<210> SEQ ID NO 587
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 587
tccatgccgt tcctgccgtt                                              20

<210> SEQ ID NO 588
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 588
tccatgccgt tcctgccgtt                                              20

<210> SEQ ID NO 589
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 589
tccatgcgcg tcctgcgcgt                                              20

<210> SEQ ID NO 590
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 590
tccatgcgtg cgtgcgtttt                                              20

<210> SEQ ID NO 591
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 591
tccatgcgtt gcgttgcgtt                                              20

<210> SEQ ID NO 592
```

```
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 592
tccatgctgg tcctgagtct                                              20

<210> SEQ ID NO 593
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 593
tccatgctgg tcctgatgct                                              20

<210> SEQ ID NO 594
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 594
tccatggcgg gcctggcggg                                              20

<210> SEQ ID NO 595
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 595
tccatggcgg tcctgatgct                                              20

<210> SEQ ID NO 596
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 596
tccatgtagt tcctagttct                                              20

<210> SEQ ID NO 597
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 597
tccatgtcct tcctgatgct                                           20

<210> SEQ ID NO 598
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 598
tccatgtcga tcctgagtct                                           20

<210> SEQ ID NO 599
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 599
tccatgtcga tcctgatgct                                           20

<210> SEQ ID NO 600
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 600
tccatgtcgc tcctgagtct                                           20

<210> SEQ ID NO 601
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 601
tccatgtcgc tcctgatcct                                           20

<210> SEQ ID NO 602
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
``` backbone with phosphorothioate at 5' and 3' ends

<400> SEQUENCE: 602
tccatgtcgg tcctgagtct				20

<210> SEQ ID NO 603
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 603
tccatgtcgg tcctgatgct				20

<210> SEQ ID NO 604
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 604
tccatgtcgg tcctgatgct				20

<210> SEQ ID NO 605
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 605
tccatgtcgg tcctgctgat				20

<210> SEQ ID NO 606
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (12)...(12)
<223> OTHER INFORMATION: m5c

<400> SEQUENCE: 606
tccatgtcgg tnctgatgct				20

<210> SEQ ID NO 607
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 607
tccatgtcgt tccgcgcgcg                                      20

<210> SEQ ID NO 608
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 608
tccatgtcgt tcctagttct                                      20

<210> SEQ ID NO 609
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 609
tccatgtcgt tcctgagtct                                      20

<210> SEQ ID NO 610
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 610
tccatgtcgt tcctgatgcg                                      20

<210> SEQ ID NO 611
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 611
tccatgtcgt tcctgatgct                                      20

<210> SEQ ID NO 612
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 612
tccatgtcgt tcctgccgct                                      20

<210> SEQ ID NO 613
<211> LENGTH: 20
<212> TYPE: DNA

```
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 613
tccatgtcgt tcctgtagct                                              20

<210> SEQ ID NO 614
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 614
tccatgtcgt tcctgtcgtt                                              20

<210> SEQ ID NO 615
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 615
tccatgtcgt tcctgtcgtt                                              20

<210> SEQ ID NO 616
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 616
tccatgtcgt ttttgtcgtt                                              20

<210> SEQ ID NO 617
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 617
tccatgtgct tcctgatgct                                              20

<210> SEQ ID NO 618
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: chimeric phosphorothioate/phosphodiester
      backbone with phosphorothioate at 5' and 3' ends
<221> NAME/KEY: modified_base
<222> LOCATION: (8)...(8)
<223> OTHER INFORMATION: m5c

<400> SEQUENCE: 618
tccatgtngg tcctgagtct                                             20

<210> SEQ ID NO 619
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (8)...(8)
<223> OTHER INFORMATION: m5c

<400> SEQUENCE: 619
tccatgtngg tcctgatgct                                             20

<210> SEQ ID NO 620
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (8)...(8)
<223> OTHER INFORMATION: m5c

<400> SEQUENCE: 620
tccatgtngt tcctgatgct                                             20

<210> SEQ ID NO 621
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: modified_base
<222> LOCATION: (8)...(8)
<223> OTHER INFORMATION: m5c
<221> NAME/KEY: modified_base
<222> LOCATION: (17)...(17)
<223> OTHER INFORMATION: m5c

<400> SEQUENCE: 621
tccatgtngt tcctgtngtt                                             20

<210> SEQ ID NO 622
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

```
<400> SEQUENCE: 622
tccattgcgt tccttgcgtt                                              20

<210> SEQ ID NO 623
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 623
tcccgacggt gaagt                                                   15

<210> SEQ ID NO 624
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 624
tcccgccgtt gaagt                                                   15

<210> SEQ ID NO 625
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 625
tcccgcgcgt tccgcgcgtt                                              20

<210> SEQ ID NO 626
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 626
tccctgagac tgccccacct t                                            21

<210> SEQ ID NO 627
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 627 tccgatcg                                                            8

<210> SEQ ID NO 628
<211> LENGTH: 15
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 628
tccggacggt gaagt                                                      15

<210> SEQ ID NO 629
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 629
tccggccgtt gaagt                                                      15

<210> SEQ ID NO 630
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 630 tccgtacg                                                               8

<210> SEQ ID NO 631
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 631
tcctaacgtt gaagt                                                      15

<210> SEQ ID NO 632
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 632
tcctagcgtt gaagt                                                      15

<210> SEQ ID NO 633
<211> LENGTH: 15
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphodiester backbone

<400> SEQUENCE: 633
tcctcacgtt gaagt                                                          15

<210> SEQ ID NO 634
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 634 tcctga                                                                     6

<210> SEQ ID NO 635
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 635
tcctgaaaag gaagt                                                          15

<210> SEQ ID NO 636
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 636
tcctgacgat gaagt                                                          15

<210> SEQ ID NO 637
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 637
tcctgacgct gaagt                                                          15

<210> SEQ ID NO 638
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

```
<400> SEQUENCE: 638
tcctgacggg gaagt                                                    15

<210> SEQ ID NO 639
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 639
tcctgacggg gaagt                                                    15

<210> SEQ ID NO 640
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 640
tcctgacggg gagt                                                     14

<210> SEQ ID NO 641
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 641
tcctgacggt gaagt                                                    15

<210> SEQ ID NO 642
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 642
tcctgacggt gaagt                                                    15

<210> SEQ ID NO 643
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 643
tcctgacgta gaagt                                                    15
```

```
<210> SEQ ID NO 644
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 644
tcctgacgtc gaagt                                                    15

<210> SEQ ID NO 645
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphodiester backbone

<400> SEQUENCE: 645
tcctgacgtg gaagt                                                    15

<210> SEQ ID NO 646
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 646
tcctgacgtg gaagt                                                    15

<210> SEQ ID NO 647
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 647
tcctgacgtt aga                                                      13

<210> SEQ ID NO 648
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 648
tcctgacgtt ccc                                                      13

<210> SEQ ID NO 649
<211> LENGTH: 32
<212> TYPE: DNA
```

```
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 649
tcctgacgtt cccctggcgg tccctgtcg ct                                32

<210> SEQ ID NO 650
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 650
tcctgacgtt cctgacgtt                                              19

<210> SEQ ID NO 651
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 651
tcctgacgtt cctggcggtc ctgtcgct                                    28

<210> SEQ ID NO 652
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 652
tcctgacgtt ccttc                                                  15

<210> SEQ ID NO 653
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 653
tcctgacgtt cggcgcgcgc cc                                          22

<210> SEQ ID NO 654
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphodiester backbone

<400> SEQUENCE: 654
tcctgacgtt gaagt                                                      15

<210> SEQ ID NO 655
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 655
tcctgacgtt gaagt                                                      15

<210> SEQ ID NO 656
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 656
tcctgagctt gaagt                                                      15

<210> SEQ ID NO 657
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 657
tcctgagctt gaagt                                                      15

<210> SEQ ID NO 658
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: m5c

<400> SEQUENCE: 658
tcctgangtt gaagt                                                      15

<210> SEQ ID NO 659
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

<223> OTHER INFORMATION: phosphodiester backbone

<400> SEQUENCE: 659
tcctgccgtt gaagt                                                        15

<210> SEQ ID NO 660
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 660
tcctgccgtt gaagt                                                        15

<210> SEQ ID NO 661
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 661
tcctggaggg gaagt                                                        15

<210> SEQ ID NO 662
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 662
tcctggaggg gaagt                                                        15

<210> SEQ ID NO 663
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 663
tcctggcggg gaagt                                                        15

<210> SEQ ID NO 664
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 664

```
tcctggcggg gaagt                                                    15

<210> SEQ ID NO 665
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 665
tcctggcggt cctggcggtt                                               20

<210> SEQ ID NO 666
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 666
tcctggcggt gaagt                                                    15

<210> SEQ ID NO 667
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 667
tcctggcggt gaagt                                                    15

<210> SEQ ID NO 668
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 668
tcctggcgtg gaagt                                                    15

<210> SEQ ID NO 669
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 669
tcctggcgtt gaagt                                                    15

<210> SEQ ID NO 670
```

```
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 670
tcctggcgtt gaagt                                              15

<210> SEQ ID NO 671
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 671
tcctgggggg gaagt                                              15

<210> SEQ ID NO 672
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 672
tcctggtggg gaagt                                              15

<210> SEQ ID NO 673
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (7)...(7)
<223> OTHER INFORMATION: m5c

<400> SEQUENCE: 673
tcctggnggg gaagt                                              15

<210> SEQ ID NO 674
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 674
tcctgtcgct cctgtcgct                                          19

<210> SEQ ID NO 675
<211> LENGTH: 28
```

<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 675
tcctgtcgct cctgtcgctc ctgtcgct                                        28

<210> SEQ ID NO 676
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 676
tcctgtcgtt cctgtcgtt                                                  19

<210> SEQ ID NO 677
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 677
tcctgtcgtt cctgtcgttg gaacgacagg                                      30

<210> SEQ ID NO 678
<211> LENGTH: 40
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 678
tcctgtcgtt cctgtcgttt caacgtcagg aacgacagga                           40

<210> SEQ ID NO 679
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 679
tcctgtcgtt ccttgtcgtt                                                 20

<210> SEQ ID NO 680
<211> LENGTH: 15
<212> TYPE: DNA
<213> ORGANISM: Artificial Sequence
<220> FEATURE:
<223> OTHER INFORMATION: Synthetic oligonucleotide

```
<221> NAME/KEY: misc_feature
<222> LOCATION: (0)...(0)
<223> OTHER INFORMATION: phosphodiester backbone

<400> SEQUENCE: 680
tcctgtcgtt gaagt                                                    15

<210> SEQ ID NO 681
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 681
tcctgtcgtt gaagttttt                                                20

<210> SEQ ID NO 682
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 682
tcctgtcgtt ttttgtcgtt                                               20

<210> SEQ ID NO 683
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 683
tccttacgtt gaagt                                                    15

<210> SEQ ID NO 684
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 684
tccttgtcgt tcctgtcgtt                                               20

<210> SEQ ID NO 685
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

```
<400> SEQUENCE: 685 tcgacgtc                                                             8

<210> SEQ ID NO 686
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 686
tcgacgttcc cccccccccc                                               20

<210> SEQ ID NO 687
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 687
tcgagacatt gcacaatcat ctg                                           23

<210> SEQ ID NO 688
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 688
tcgccgttcc cccccccccc                                               20

<210> SEQ ID NO 689
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 689
tcgcgtgcgt tttgtcgttt tgacgtt                                       27

<210> SEQ ID NO 690
<211> LENGTH: 5
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 690 tcgga                                                                5
```

```
<210> SEQ ID NO 691
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 691
tcggcgttcc cccccccccc                                              20

<210> SEQ ID NO 692
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_difference
<222> LOCATION: (0)...(0)
<223> OTHER INFORMATION: phosphorothioate backbone

<400> SEQUENCE: 692 tcgtag                                                              6

<210> SEQ ID NO 693
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 693 tcgtca                                                              6

<210> SEQ ID NO 694
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 694
tcgtcattcc cccccccccc                                              20

<210> SEQ ID NO 695
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 695
tcgtcgatcc cccccccccc                                              20

<210> SEQ ID NO 696
<211> LENGTH: 20
<212> TYPE: DNA
```

<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 696
tcgtcgctcc cccccccccc                                               20

<210> SEQ ID NO 697
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 697
tcgtcgctgt ctccg                                                    15

<210> SEQ ID NO 698
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 698
tcgtcgctgt ctccgcttct t                                             21

<210> SEQ ID NO 699
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 3' end

<400> SEQUENCE: 699
tcgtcgctgt ctccgcttct t                                             21

<210> SEQ ID NO 700
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorodithioate/phosphodiester
      backbone with phosphodiester on 3' end

<400> SEQUENCE: 700
tcgtcgctgt ctccgcttct t                                             21

<210> SEQ ID NO 701
<211> LENGTH: 27
<212> TYPE: DNA
<213> ORGANISM: Artificial Sequence
<220> FEATURE:

```
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 701
tcgtcgctgt ctccgcttct tcttgcc                                          27

<210> SEQ ID NO 702
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 702
tcgtcgctgt ctgcccttct t                                                21

<210> SEQ ID NO 703
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 703
tcgtcgctgt tgtcgtttct t                                                21

<210> SEQ ID NO 704
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 704
tcgtcggtcc cccccccccc                                                  20

<210> SEQ ID NO 705
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 705
tcgtcgtcag ttcgctgtcg                                                  20

<210> SEQ ID NO 706
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
```

```
<223> OTHER INFORMATION: chimeric phosphorothioate/phosphodiester
      backbone with phosphorothioate at 5' and 3' ends

<400> SEQUENCE: 706
tcgtcgtcgt cgtcgtcgtc gtt                                            23

<210> SEQ ID NO 707
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 707
tcgtcgtcgt cgtt                                                      14

<210> SEQ ID NO 708
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 708
tcgtcgtcgt cgtt                                                      14

<210> SEQ ID NO 709
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorodithioate/phosphodiester
      backbone with phosphodiester on 3' end

<400> SEQUENCE: 709
tcgtcgtcgt cgtt                                                      14

<210> SEQ ID NO 710
<211> LENGTH: 14
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorodithioate/phosphodiester
      backbone with phosphodiester on 5' end

<400> SEQUENCE: 710
tcgtcgtcgt cgtt                                                      14

<210> SEQ ID NO 711
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
```

```
<400> SEQUENCE: 711
tcgtcgttcc ccccccc                                              17

<210> SEQ ID NO 712
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 712
tcgtcgttcc cccccccccc                                           20

<210> SEQ ID NO 713
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (20)...(20)
<223> OTHER INFORMATION: biotinylated at 3' end

<400> SEQUENCE: 713
tcgtcgttcc cccccccccc                                           20

<210> SEQ ID NO 714
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (16)...(16)
<223> OTHER INFORMATION: m5c

<400> SEQUENCE: 714
tcgtcgttcc cccccncccc                                           20

<210> SEQ ID NO 715
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 715
tcgtcgttgg tgtcgttggt gtcgtt                                    26

<210> SEQ ID NO 716
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
```

<222> LOCATION: (0)...(0)
<223> OTHER INFORMATION: phosphorothioate backbone

<400> SEQUENCE: 716
tcgtcgttgg ttgtcgtttt ggtt                                              24

<210> SEQ ID NO 717
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 717
tcgtcgttgt cgttgtcgtt                                                   20

<210> SEQ ID NO 718
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 718
tcgtcgttgt cgttgtcgtt                                                   20

<210> SEQ ID NO 719
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 719
tcgtcgttgt cgttttgtcg tt                                                22

<210> SEQ ID NO 720
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 720
tcgtcgttgt cgttttgtcg tt                                                22

<210> SEQ ID NO 721
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

```
<400> SEQUENCE: 721
tcgtcgtttc gtcgttttga cgtt                                              24

<210> SEQ ID NO 722
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 722
tcgtcgtttg cgtgcgtttc gtcgtt                                            26

<210> SEQ ID NO 723
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 723
tcgtcgtttg tcgttttgtc gtt                                               23

<210> SEQ ID NO 724
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 724
tcgtcgtttt gacgttttga cgtt                                              24

<210> SEQ ID NO 725
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 725
tcgtcgtttt gacgttttgt cgtt                                              24

<210> SEQ ID NO 726
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 726
tcgtcgtttt gcgtgcgttt                                                   20
```

<210> SEQ ID NO 727
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 727
tcgtcgtttt gtcgttttgg gggg                                           24

<210> SEQ ID NO 728
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 728
tcgtcgtttt gtcgttttgt cgt                                            23

<210> SEQ ID NO 729
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 729
tcgtcgtttt gtcgttttgt cgtt                                           24

<210> SEQ ID NO 730
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
    backbone with phosphorothioate at 5' and 3' ends

<400> SEQUENCE: 730
tcgtcgtttt gtcgttttgt cgtt                                           24

<210> SEQ ID NO 731
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 731
tcgtcgtttt gtcgttttgt cgtt                                           24

<210> SEQ ID NO 732
<211> LENGTH: 24
<212> TYPE: DNA
<213> ORGANISM: Artificial Sequence

```
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 732
tcgtcgtttt gtcgttttgt cgtt                                              24

<210> SEQ ID NO 733
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (24)...(24)
<223> OTHER INFORMATION: biotinylated at 3' end

<400> SEQUENCE: 733
tcgtcgtttt gtcgttttgt cgtt                                              24

<210> SEQ ID NO 734
<211> LENGTH: 32
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 734
tcgtcgtttt gtcgttttgt cgttttgtcg tt                                     32

<210> SEQ ID NO 735
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 735
tcgtcgtttt gtggttttgt ggtt                                              24

<210> SEQ ID NO 736
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 736
tcgtcgtttt ttgtcgtttt ttgtcgtt                                          28

<210> SEQ ID NO 737
<211> LENGTH: 20
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 737
tcgtcgtttt tttttttttt                                            20

<210> SEQ ID NO 738
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 738 tcgtga                                                            6

<210> SEQ ID NO 739
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 739 tcgtga                                                            6

<210> SEQ ID NO 740
<211> LENGTH: 6
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 740 tcgtgg                                                            6

<210> SEQ ID NO 741
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (5)...(5)
<223> OTHER INFORMATION: m5c

<400> SEQUENCE: 741
tcgtngttcc cccccccccc                                            20

<210> SEQ ID NO 742
<211> LENGTH: 24
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (0)...(0)
<223> OTHER INFORMATION: phosphorothioate backbone

<400> SEQUENCE: 742
tcntcgtntt ntcgtnttnt cgtn                                           24

<210> SEQ ID NO 743
<211> LENGTH: 26
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 743
tctaaaaacc atctattctt aaccct                                         26

<210> SEQ ID NO 744
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 744
tctagcgttt ttagcgttcc                                                20

<210> SEQ ID NO 745
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 745
tctatcccag gtggttcctg ttag                                           24

<210> SEQ ID NO 746
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 746
tctatcgacg ttcaagcaag                                                20

<210> SEQ ID NO 747
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
```

<400> SEQUENCE: 747
tctccatcct atggtttat cg                                          22

<210> SEQ ID NO 748
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 748
tctccatgat ggttttatcg                                            20

<210> SEQ ID NO 749
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 749
tctcccagcg agcgagcgcc at                                         22

<210> SEQ ID NO 750
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 750
tctcccagcg agcgccat                                              18

<210> SEQ ID NO 751
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 751
tctcccagcg cgcgccat                                              18

<210> SEQ ID NO 752
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 752
tctcccagcg ggcgcat                                               17

<210> SEQ ID NO 753

```
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 753
tctcccagcg tacgccat                                                   18

<210> SEQ ID NO 754
<211> LENGTH: 17
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 754
tctcccagcg tcgccat                                                    17

<210> SEQ ID NO 755
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 755
tctcccagcg tgcgccat                                                   18

<210> SEQ ID NO 756
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 756
tctcccagcg tgcgccat                                                   18

<210> SEQ ID NO 757
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 757
tctcccagcg tgcgccatat                                                 20

<210> SEQ ID NO 758
<211> LENGTH: 20
<212> TYPE: DNA
<213> ORGANISM: Artificial Sequence
```

```
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 758
tctcccagcg tgcgcctttt                                                 20

<210> SEQ ID NO 759
<211> LENGTH: 22
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 759
tctcccagcg tgcgtgcgcc at                                              22

<210> SEQ ID NO 760
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 760
tctcccagcg tgcgttatat                                                 20

<210> SEQ ID NO 761
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 761
tctcccagcg tgcgtttt                                                   18

<210> SEQ ID NO 762
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 762
tctcccagcg ttgcgccata t                                               21

<210> SEQ ID NO 763
<211> LENGTH: 17
<212> TYPE: DNA
<213> ORGANISM: Artificial Sequence
<220> FEATURE:
```

```
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 763
tctcccatcg tcgccat                                                  17

<210> SEQ ID NO 764
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 764
tctcccgacg tgcgccat                                                 18

<210> SEQ ID NO 765
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 765
tctcccgtcg tgcgccat                                                 18

<210> SEQ ID NO 766
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 766
tctccctgcg tgcgccatat                                               20

<210> SEQ ID NO 767
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 767
tctcctagcg tgcgccatat                                               20

<210> SEQ ID NO 768
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
```

```
<222> LOCATION: (0)...(0)
<223> OTHER INFORMATION: phosphodiester backbone

<400> SEQUENCE: 768
tctgacgtca tctgacgttg gctgacgtct                                     30

<210> SEQ ID NO 769
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 769
tctgcgtgcg tgcgccatat                                                20

<210> SEQ ID NO 770
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 770 tcttcgaa                                                              8

<210> SEQ ID NO 771
<211> LENGTH: 45
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 771
tcttgcgatg ctaaaggacg tcacattgca caatcttaat aaggt                    45

<210> SEQ ID NO 772
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 772
tctttattag tgactcagca cttggca                                        27

<210> SEQ ID NO 773
<211> LENGTH: 15
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
```

```
<222> LOCATION: (3)...(3)
<223> OTHER INFORMATION: m5c

<400> SEQUENCE: 773
tcntgacgtt gaagt                                                     15

<210> SEQ ID NO 774
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 774 tgaacgtt                                                              8

<210> SEQ ID NO 775
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 775
tgcaatgtga cgtcctttag cat                                            23

<210> SEQ ID NO 776
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 776
tgcaggaagt ccgggttttc cccaacccccc c                                  31

<210> SEQ ID NO 777
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 777
tgcatcagct ct                                                        12

<210> SEQ ID NO 778
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends
```

-continued

```
<400> SEQUENCE: 778
tgcatcagct ct                                                         12

<210> SEQ ID NO 779
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 779
tgcatccccc aggccaccat                                                 20

<210> SEQ ID NO 780
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 780
tgcatgccgt acacagctct                                                 20

<210> SEQ ID NO 781
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 781
tgcatgccgt acacagctct                                                 20

<210> SEQ ID NO 782
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 782
tgcatgccgt acacagctct                                                 20

<210> SEQ ID NO 783
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 783
tgcatgccgt gcatccgtac acagctct                                        28
```

```
<210> SEQ ID NO 784
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 784
tgccaagtgc tgagtcacta ataaaga                                27

<210> SEQ ID NO 785
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 785
tgcccaaaga ggaaaatttg tttcatacag                             30

<210> SEQ ID NO 786
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 786 tgcgctct                                                      8

<210> SEQ ID NO 787
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 787
tgctagctgt gcctgtacct                                        20

<210> SEQ ID NO 788
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 788
tgctagctgt gcctgtacct                                        20

<210> SEQ ID NO 789
<211> LENGTH: 20
<212> TYPE: DNA
<213> ORGANISM: Artificial Sequence
<220> FEATURE:
```

<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 789
tgctgcttcc cccccccccc                                            20

<210> SEQ ID NO 790
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 790
tgctgcttcc cccccccccc                                            20

<210> SEQ ID NO 791
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 791
tgctgctttt gtgcttttgt gctt                                       24

<210> SEQ ID NO 792
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 792
tgctgctttt gtgcttttgt gctt                                       24

<210> SEQ ID NO 793
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 793
tggaccttcc at                                                    12

<210> SEQ ID NO 794
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 794
tggaccttct atgtcggtcc                                            20

```
<210> SEQ ID NO 795
<211> LENGTH: 43
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 795
tggagggtga gggtggggcc agagcgggtg gggctgattg gaa                43

<210> SEQ ID NO 796
<211> LENGTH: 23
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 796
tggaggtccc accgagatcg gag                                      23

<210> SEQ ID NO 797
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 797
tggttacggt ctgtcccatg                                          20

<210> SEQ ID NO 798
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 798
tgtatctctc tgaaggact                                           19

<210> SEQ ID NO 799
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 799
tgtccagccg aggggaccat                                          20

<210> SEQ ID NO 800
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 800
tgtcccatgt ttttagaagc                                          20
```

<210> SEQ ID NO 801
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 801
tgtcgttgtc gtt                                                          13

<210> SEQ ID NO 802
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 802
tgtcgttgtc gttgtcgttg tcgtt                                             25

<210> SEQ ID NO 803
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 803
tgtcgtttgt cgtttgtcgt t                                                 21

<210> SEQ ID NO 804
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 804
ttaacggtgg tagcggtatt ggtc                                              24

<210> SEQ ID NO 805
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 805 ttaacgtt                                                                 8

<210> SEQ ID NO 806
<211> LENGTH: 24

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 806
ttaagaccaa taccgctacc accg                                              24

<210> SEQ ID NO 807
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 807
ttaggacaag gtctagggtg                                                   20

<210> SEQ ID NO 808
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorodithioate backbone

<400> SEQUENCE: 808
ttagggttag ggttagggtt                                                   20

<210> SEQ ID NO 809
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 809
ttcagttgtc ttgctgctta gctaa                                             25

<210> SEQ ID NO 810
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 810
ttcatgcctt gcaaaatggc g                                                 21

<210> SEQ ID NO 811
<211> LENGTH: 43
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 811
```

-continued

```
ttccaatcag ccccacccgc tctggcccca ccctcaccct cca                    43
```

<210> SEQ ID NO 812
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 812

```
ttccatgctg ttccggctgg                                              20
```

<210> SEQ ID NO 813
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 813

```
ttccatgtcg gtcctgat                                                18
```

<210> SEQ ID NO 814
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 814

```
ttccgccgaa tggcctcagg atggtac                                      27
```

<210> SEQ ID NO 815
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 815

```
ttccgcttta tctgagaacc atct                                         24
```

<210> SEQ ID NO 816
<211> LENGTH: 19
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 816

```
ttcctctctg caagagact                                               19
```

<210> SEQ ID NO 817
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester backbone with phosphorothioate at 5' and 3' ends

<400> SEQUENCE: 817
ttcgggcgga ctcctccatt                20

<210> SEQ ID NO 818
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 818
ttcgggcgga ctcctccatt                20

<210> SEQ ID NO 819
<211> LENGTH: 25
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 819
ttcgtcgttt tgtcgttttg tcgtt           25

<210> SEQ ID NO 820
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 820
ttctgtgtct gttgctggtt ccgctttatc tgagaac    37

<210> SEQ ID NO 821
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 821
ttgaaactga ggtgggac                  18

<210> SEQ ID NO 822
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 822
ttgccccata ttttagaaac                20

<210> SEQ ID NO 823
<211> LENGTH: 12
<212> TYPE: DNA
<213> ORGANISM: Artificial Sequence
<220> FEATURE:
<223> OTHER INFORMATION: Synthetic oligonucleotide

```
<221> NAME/KEY: misc_feature
<222> LOCATION: (0)...(0)
<223> OTHER INFORMATION: phosphorothioate backbone

<400> SEQUENCE: 823
ttgggggggg tt                                                    12

<210> SEQ ID NO 824
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 824
ttgtactctc catgatggtt                                            20

<210> SEQ ID NO 825
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 825 tttaccttt ataaacataa ctaaaacaaa                                  30

<210> SEQ ID NO 826
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 826
tttgaatcct cagcggtctc cagtggc                                    27

<210> SEQ ID NO 827
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 827
tttgaattca ggactggtga ggttgag                                    27

<210> SEQ ID NO 828
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 828
tttgaattcc gtgtacagaa gcgagaagc                                  29
```

```
<210> SEQ ID NO 829
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphorothioate at 5' and 3' ends

<400> SEQUENCE: 829
tttgagaacg ctggaccttc                                                     20

<210> SEQ ID NO 830
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 830
tttgcggccg ctagacttaa cctgagagat a                                        31

<210> SEQ ID NO 831
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 831
tttgggccca cgagagacag agacacttc                                           29

<210> SEQ ID NO 832
<211> LENGTH: 29
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 832
tttgggcccg cttctcgctt ctgtacacg                                           29

<210> SEQ ID NO 833
<211> LENGTH: 28
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 833
ttttctagag aggtgcacaa tgctctgg                                            28

<210> SEQ ID NO 834
```

```
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 834
tttttggggg ggggtttttt                                              20

<210> SEQ ID NO 835
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: misc_feature
<222> LOCATION: (13)...(13)
<223> OTHER INFORMATION: FITC labeled

<400> SEQUENCE: 835
tttttttttt ttt                                                     13

<210> SEQ ID NO 836
<211> LENGTH: 13
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: chimeric phosphorothioate/phosphodiester
      backbone with phosphodiester on 3' end
<221> NAME/KEY: misc_difference
<222> LOCATION: (13)...(13)
<223> OTHER INFORMATION: FITC labeled

<400> SEQUENCE: 836
tttttttttt ttt                                                     13

<210> SEQ ID NO 837
<211> LENGTH: 18
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 837
tttttttttt tttttttt                                                18

<210> SEQ ID NO 838
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 838
tttttttttt tttttttttt                                              20
```

```
<210> SEQ ID NO 839
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone

<400> SEQUENCE: 839
tttttttttt tttttttttt                                              20

<210> SEQ ID NO 840
<211> LENGTH: 21
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 840
tttttttttt tttttttttt t                                            21

<210> SEQ ID NO 841
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 841
tttttttttt tttttttttt tttt                                         24

<210> SEQ ID NO 842
<211> LENGTH: 27
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone

<400> SEQUENCE: 842
tttttttttt tttttttttt ttttttt                                      27

<210> SEQ ID NO 843
<211> LENGTH: 8
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c

<400> SEQUENCE: 843 tnaacgtt                                                            8
```

<210> SEQ ID NO 844
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c

<400> SEQUENCE: 844
tngtcgttcc cccccccccc                                          20

<210> SEQ ID NO 845
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c

<400> SEQUENCE: 845
tngtcgtttt gtcgttttgt cgtt                                     24

<210> SEQ ID NO 846
<211> LENGTH: 20
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c

<400> SEQUENCE: 846
tngtggttcc cccccccccc                                          20

<210> SEQ ID NO 847
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphodiester backbone
<221> NAME/KEY: modified_base
<222> LOCATION: (2)...(2)
<223> OTHER INFORMATION: m5c
<221> NAME/KEY: modified_base
<222> LOCATION: (5)...(5)
<223> OTHER INFORMATION: m5c
<221> NAME/KEY: modified_base
<222> LOCATION: (13)...(13)
<223> OTHER INFORMATION: m5c
<221> NAME/KEY: modified_base
<222> LOCATION: (21)...(21)
<223> OTHER INFORMATION: m5c

<400> SEQUENCE: 847

```
tngtgntttt gtngttttgt ngtt                                          24

<210> SEQ ID NO 848
<211> LENGTH: 24
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (0)...(0)
<223> OTHER INFORMATION: phosphorothioate backbone
<221> NAME/KEY: modified_base
<222> LOCATION: (2)...(2)
<223> OTHER INFORMATION: m5c
<221> NAME/KEY: modified_base
<222> LOCATION: (5)...(5)
<223> OTHER INFORMATION: m5c
<221> NAME/KEY: modified_base
<222> LOCATION: (13)...(13)
<223> OTHER INFORMATION: m5c
<221> NAME/KEY: modified_base
<222> LOCATION: (21)...(21)
<223> OTHER INFORMATION: m5c

<400> SEQUENCE: 848
tngtngtttt gtngttttgt ngtt                                          24
```